(12) United States Patent
Liang et al.

(10) Patent No.: US 11,912,876 B2
(45) Date of Patent: Feb. 27, 2024

(54) BLUE-EXCITABLE WATER-SOLVATED POLYMERIC DYES

(71) Applicant: Becton, Dickinson and Company, Franklin Lakes, NJ (US)

(72) Inventors: Yongchao Liang, Irvine, CA (US); Haiqing Li, San Diego, CA (US); Brent S. Gaylord, San Diego, CA (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 345 days.

(21) Appl. No.: 17/126,961

(22) Filed: Dec. 18, 2020

(65) Prior Publication Data
US 2021/0108083 A1    Apr. 15, 2021

Related U.S. Application Data

(63) Continuation of application No. 15/642,255, filed on Jul. 5, 2017, now Pat. No. 10,920,082.

(60) Provisional application No. 62/360,882, filed on Jul. 11, 2016.

(51) Int. Cl.
| | |
|---|---|
| *C09K 8/28* | (2006.01) |
| *C09B 69/10* | (2006.01) |
| *C08G 61/12* | (2006.01) |
| *C09B 69/00* | (2006.01) |
| *G01N 33/58* | (2006.01) |

(52) U.S. Cl.
CPC ............ *C09B 69/10* (2013.01); *C08G 61/124* (2013.01); *C08G 61/126* (2013.01); *C09B 69/00* (2013.01); *C08G 2261/148* (2013.01); *C08G 2261/1424* (2013.01); *C08G 2261/1644* (2013.01); *C08G 2261/1646* (2013.01); *C08G 2261/3142* (2013.01); *C08G 2261/3223* (2013.01); *C08G 2261/3241* (2013.01); *C08G 2261/3243* (2013.01); *C08G 2261/3246* (2013.01); *C08G 2261/344* (2013.01); *C08G 2261/41* (2013.01); *C08G 2261/411* (2013.01); *C08G 2261/414* (2013.01); *C08G 2261/522* (2013.01); *C08G 2261/72* (2013.01); *G01N 33/582* (2013.01)

(58) Field of Classification Search
CPC .... C09B 69/10; C08G 61/124; C08G 61/126; C08G 61/1424; C08G 2261/148; C08G 2261/1644; C08G 2261/3142; C08G 2261/3223; C08G 2261/72; G01N 33/582; C09K 8/28; C09K 23/018; C09K 23/24
See application file for complete search history.

(56) References Cited

U.S. PATENT DOCUMENTS

| | | | |
|---|---|---|---|
| 7,144,950 B2 | 12/2006 | Bazan et al. | |
| 7,214,489 B2 | 5/2007 | Bazan et al. | |
| 7,241,513 B2 | 7/2007 | Suzuki et al. | |
| 7,270,956 B2 | 9/2007 | Bazan et al. | |
| 7,629,448 B2 | 12/2009 | Bazan et al. | |
| 7,666,594 B2 | 2/2010 | Bazan et al. | |
| 7,811,755 B2 | 10/2010 | Bazan et al. | |
| 7,897,684 B2 | 3/2011 | Bazan et al. | |
| 7,914,984 B2 | 3/2011 | Bazan et al. | |
| 8,101,416 B2 | 1/2012 | Bazan et al. | |
| 8,110,673 B2 | 2/2012 | Bazan et al. | |
| 8,158,444 B2 | 4/2012 | Gaylord et al. | |
| 8,227,187 B2 | 7/2012 | Bazan et al. | |
| 8,309,672 B2 | 11/2012 | Bazan et al. | |
| 8,338,532 B2 | 12/2012 | Bazan et al. | |
| 8,354,239 B2 | 1/2013 | Gaylord et al. | |
| 8,362,193 B2 | 1/2013 | Gaylord et al. | |
| 8,455,613 B2 | 6/2013 | Gaylord et al. | |
| 8,546,081 B2 | 10/2013 | Bazan et al. | |
| 8,575,303 B2 | 11/2013 | Gaylord et al. | |
| 8,617,814 B2 | 12/2013 | Bazan et al. | |
| 8,669,055 B2 | 3/2014 | Bazan et al. | |
| 8,759,444 B2 | 6/2014 | Bazan et al. | |
| 8,802,450 B2 | 8/2014 | Gaylord et al. | |
| 8,835,113 B2 | 9/2014 | Bazan et al. | |
| 8,841,072 B2 | 9/2014 | Bazan et al. | |

(Continued)

FOREIGN PATENT DOCUMENTS

| | | |
|---|---|---|
| WO | WO 2004/001379 A2 | 12/2003 |
| WO | WO 2004/077014 A2 | 9/2004 |

(Continued)

OTHER PUBLICATIONS

Bu et al. "Photochemically colour-tuneable white fluorescence illuminants consisting of conjugated polymer nanospheres", Nat Commun., 2014, vol. 5, No. 3799, pp. 1-8.

Feng et al. "Water-soluble fluorescent conjugated polymers and their interactions with biomacromolecules for sensitive biosensors," Chem. Soc. Rev., vol. 39, 2010, pp. 2411-2419.

Liu et al. "Blue-Light-Emitting Fluorene-Based Polymers with Tunable Electronic Properties," Chem. Mater. 2001, vol. 13, pp. 1984-1991.

(Continued)

*Primary Examiner* — Kumar R Bhushan
(74) *Attorney, Agent, or Firm* — Michael J. Blessent; Bret E. Field; BOZICEVIC, FIELD & FRANCIS LLP

(57) ABSTRACT

Water solvated polymeric dyes and polymeric tandem dyes having a blue excitation spectrum are provided. The polymeric dyes are conjugated polymers that can include a thiophene-containing co-monomer. The polymeric tandem dyes further include a signaling chromophore covalently linked to the conjugated polymer in energy-receiving proximity therewith. Also provided are labelled specific binding members that include the subject polymeric dyes. Methods of evaluating a sample for the presence of a target analyte and methods of labelling a target molecule in which the subject polymeric dyes find use are also provided. Systems and kits for practicing the subject methods are also provided.

9 Claims, 2 Drawing Sheets

(56) References Cited

U.S. PATENT DOCUMENTS

| | | | |
|---|---|---|---|
| 8,969,509 B2 | 3/2015 | Liu et al. | |
| 8,993,335 B2 | 3/2015 | Bazan et al. | |
| 9,085,799 B2 | 7/2015 | Bazan et al. | |
| 9,139,869 B2 | 9/2015 | Gaylord et al. | |
| 9,159,465 B2 | 10/2015 | Bazan et al. | |
| 9,371,559 B2 | 6/2016 | Bazan et al. | |
| 9,383,353 B2 | 7/2016 | Gaylord et al. | |
| 9,547,008 B2 | 1/2017 | Gaylord et al. | |
| 2004/0142344 A1 | 7/2004 | Bazan et al. | |
| 2005/0031801 A1 | 2/2005 | Shundo et al. | |
| 2005/0191229 A1 | 9/2005 | Chiang et al. | |
| 2008/0064042 A1 | 3/2008 | Bazan et al. | |
| 2008/0293164 A1 | 11/2008 | Gaylord et al. | |
| 2009/0095343 A1 | 4/2009 | Pei et al. | |
| 2009/0214969 A1 | 8/2009 | Coggan et al. | |
| 2009/0230362 A1 | 9/2009 | Bazan et al. | |
| 2010/0136702 A1 | 6/2010 | Bazan et al. | |
| 2011/0211435 A1* | 9/2011 | Kawasaki | G11B 7/127 |
| 2011/0256549 A1* | 10/2011 | Gaylord | H10K 85/151 562/466 |
| 2012/0028828 A1 | 2/2012 | Gaylord et al. | |
| 2012/0252986 A1 | 10/2012 | Liu et al. | |
| 2013/0109029 A1 | 5/2013 | Liu et al. | |
| 2013/0190193 A1 | 7/2013 | Bazan et al. | |
| 2015/0226746 A1 | 8/2015 | Bazan et al. | |
| 2016/0266131 A1 | 9/2016 | Liang et al. | |
| 2016/0266132 A1 | 9/2016 | Gaylord et al. | |
| 2016/0341720 A1 | 11/2016 | Bazan et al. | |
| 2016/0349267 A1 | 12/2016 | Gaylord et al. | |
| 2017/0115298 A1 | 4/2017 | Gaylord et al. | |

FOREIGN PATENT DOCUMENTS

| | | |
|---|---|---|
| WO | WO 2004/092324 A2 | 10/2004 |
| WO | WO 2005/086617 A2 | 9/2005 |
| WO | WO 2006/083932 A2 | 6/2006 |
| WO | WO 2006/074471 A2 | 7/2006 |
| WO | WO 2006/074482 A2 | 7/2006 |
| WO | WO 2008/100344 A2 | 6/2008 |
| WO | WO 2010/151807 A1 | 12/2010 |
| WO | WO 2011/091086 A1 | 7/2011 |
| WO | WO 2016/073052 A1 | 5/2016 |
| WO | WO 2016/144653 A1 | 9/2016 |

OTHER PUBLICATIONS

Liu et al. "Optimization of the Molecular Orbital Energies of Conjugated Polymers for Optical Amplification of Fluorescent Sensors," J. Am. Chem. Soc. 2006, vol. 128, pp. 1188-1196.
Marsitzky et al. "Self-Encapsulation of Poly-2,7-fluorenes in a Dendrimer Matrix," Journal of the American Chemical Society (2001), vol. 123, No. 29, pp. 6965-6972.
Pan et al. "Synthesis and properties of fluorenyl-pyridinyl alternatingcopolymers for light-emitting diodes," Polym. Int. 2014, pp. 1105-1111.
Ritchie et al. "Effect of meta-linkages on the photoluminescence and electroluminescence properties of light-emitting polyfluorene alternating copolymers," J. Mater. Chem. 2006, vol. 16, pp. 1651-1656.
Traina et al. "Design and Synthesis of Monofunctionalized, Water-Soluble Conjugated Polymers for Biosensing and Imaging Applications," J. Am. Chem. Soc. 2011, vol. 133, No. 32, pp. 12600-12607.
Wang et al. "Effect of Transannular π-π Interaction on Emission Spectral Shift and Fluorescence Quenching in Dithia[3.3]paracyclophane-Fluorene Copolymers," Macromolecules 2006, vol. 39, pp. 7277-7285.
Wu et al. "Synthesis and Characterization of Poly(fluorene)-Based Copolymers Containing Various 1,3,4-Oxadiazole Dendritic Pendants," Macromolecules 2006, vol. 39, No. 13, pp. 4298-4305.
Yang et al. "Enhancement of color purity in blue-emitting fluorene-pyridine-based copolymers by controlling the chain rigidity and effective conjugation length," Polymer, 2004, pp. 865-872.
Zalipsky et al. "Functionalized poly(ethylene glycol) for preparation of biologically relevant conjugates," Bioconjugate Chemistry 1995, vol. 6, No. 2, pp. 150-165.
Zhang et al. "Novel fluorene/trifluoromethylphenylene copolymers: Synthesis, spectra stability and electroluminescence," Dyes and Pigments, 2012, pp. 380-385.
Zhu et al. "Water-Soluble Conjugated Polymers for Imaging, Diagnosis, and Therapy", Chem. Rev., 2012, vol. 112, No. 8, pp. 4687-4735.
Gather et al. "An alignable fluorene thienothiophene copolymer with deep-blue electroluminescent emission at 410 nm", Chemical Communications (Cambridge, United Kingdom), 2008 [Epub: Jan. 7, 2008], vol. 9, pp. 1079-1081.
Liu et al. "Tuning HOMO and LUMO energy levels of blue light-emitting polyfluorene derivatives", Polymeric Materials: Science and Engineering, 2001, vol. 84, pp. 1041-1042.
Morin et al. "Syntheses of Conjugated Polymers Derived from N-Alkyl-2,7-carbazoles", Macromolecules, 2001 [Epub: Jun. 6, 2001], vol. 34, No. 14, pp. 4680-4682.
Wu et al. "Synthesis and characterization of new fluorene-acceptor alternating and random copolymers for light-emitting applications", Polymer, 2006 [Epub: Dec. 7, 2005], vol. 47, No. 2, pp. 527-538.
He, et al. "The synthesis of New Water-Soluble Conjugated Polymers for fluorescence sensing", Chinese Master's Theses Full-Text Database, Engineering Science and Technology I, Issue 4, 2016, B014-202.
Fu, et al. "Parameters influencing the molecular weight of 3,6-carbazole-based D-pi-A-type copolymers", Journal of Polymer Science, Part A: Polymer Chemistry, val. 49, No. 20, Jul. 28, 2011 (Jul. 28, 2011), pp. 4368-4378.
Herrero-Carvajal, et al. "EDOT-Based Copolymers with Pendant Anthraquinone Units: Analysis of Their Optoelectronic Properties within the Double-Cable Context", Journal of Physical Chemistry C, vol. 118, No. 19,May 5, 2014 (May 5, 2014).
Meng et al: "Replacing Alkyl with Oligo( ethylene glycol) as Side Chains of Conjugated Polymers for Close &pgr;-&pgr; Stacking", Macromolecules, val. 48, No. 13, Jul. 14, 2015 (Jul. 14, 2015), pp. 4357-4363.
Shano Godana, et al. "Fluorescent conjugated polymer nanoparticles and aggregates based on rapid precipitation and selfassembled [pi]-conjugated systems", Polymer, val. 174, pp. 45-51, Apr. 29, 2019 (Apr. 29, 2019).
Ziegler, et al. "Synthesis and characterization of alternating fluorene-thiophene copolymers bearing ethylene glycol sidechains", Monatshefte for Chemie-Chemical Monthly; an International Journal of Chemistry, Springer-.
Beaupre, S., et al.; Chemical Materials, 2000, vol. 12, p. 1931-1936.
Cassemiro, S.M., et al.; Journal of Luminescence, 2013, vol. 134, p. 670-677.
Burrows, H.D., et al.; Applied Materials & Interfaces, 2009, p. 864-874.
Wang, F., et al.; Scientific Reports, 2015, p. 1-8.
Das, S., et al.; RSC Advances, 2015, p. 20160-20177.
Donabedian, et al."Substituent, Charge, and Size Effects on the Fluorogenic Performance of Amyloid Ligands: a Small-Library Screening Study", ACS Omega, vol. 2, No. 7, Jul. 6, 2017 (Jul. 6, 2017), pp. 3192-3200.
Hirata, et al."Reversible Fluorescent on-off Recording in a Highly Transparent Polymeric Material Utilizing Fluorescent Resonance Energy Transfer (FRET) Induced by Heat Treatment", Advanced Functional Materials, Wiley—V C H Verlag Gmbh & Co. KGAA, DE, vol. 19, No. 18, Oct. 9, 2008 (Oct. 9, 2008), pages.
Malakhov, et al."1-(Phenylethynyl)pyrene 5,10 and 9,10-bis(phenylethynyl) anthracene, useful fluorescent dyes for DNA labeling: excimer formation and energy transfer", European Journal of Organic Chemistry, Wiley-VCH, DE, No. 6, Mar. 3, 2004 (Mar. 3, 2004), pp. 1298-1307.
Nagai, et al "Aromatic Ring-Fused BODIPY-Based Conjugated Polymers Exhibiting Narrow Near-Infrared Emission Bands", Macromolecules, vol. 43, No. 1, Jan. 12, 2010 (2010-91-12), pp. 193-200.
Yin, et al "Oligo(p-phenylene 5,10 ethynylene)-BODIPY Derivatives: Synthesis, Energy Transfer, and Quantum-Chemical Calcu-

(56) References Cited

OTHER PUBLICATIONS lations" Chemistry—a European Journal, vol. 17, No. 47, Oct. 11, 2011 (Oct. 11, 2011), pp. 13247-13257.
Yin, et al The synthesis and spectroscopic characterization of poly(p-phenylene ethynylene) with 3-connected BODIPY end groups 11 , Dyes and Pigments, Elsevier Applied Science Publishers. Barking, GB, vol. 88, No. 3, Mar. 1, 2011 (Mar. 1, 2011), pp. 372-377.
Zhao et al "Novel, yellow-emitting anthracene/fluorene oligomers: synthesis and characterization", Tetrahedron, Elsevier Science Publishers, Amsterdam, NL, vol. 63, No. 33, Jul. 3, 2007 (Jul. 3, 2007), pp. 7809-7815.
Moon, et al. "Live-Cell-Permeable Poly(p-phenylene ethynylene)", Angew Chem Int Ed Engl. 2007;46(43):8223-5.
Zhu, et al. "Water-Soluble Conjugated Polymers for Imaging, Diagnosis, and Therapy", Chem. Rev. 2012, 112, 8, 4687-4735.
Zhu, et a, "A potent fluorescent probe for the detection ofcellapoptosis", hem Commun (Camb) . May 21, 2011;47(19):5524-6.
Raeken, et al. "Synthesis of a multifunctional poly(p-phenylene ethynylene) scaffold12 pages with clickable azide-containing side chains for (bio)sensor applications", Polymer Chemistry, Issue 37, 2015, 12 pages.

\* cited by examiner

BLUE-EXCITABLE WATER-SOLVATED POLYMERIC DYES

CROSS-REFERENCE TO RELATED APPLICATIONS

This application is a continuation of U.S. patent application Ser. No. 15/642,255, filed on Jul. 5, 2017, which claims priority to U.S. Provisional Patent Application Ser. No. 62/360,882, filed Jul. 11, 2016, all of which are incorporated herein by reference.

INTRODUCTION

Fluorescent dyes are compounds which, when irradiated with light of a wavelength which they absorb, emit light of a (usually) different wavelength. Fluorescent dyes find use in a variety of applications in biochemistry, biology and medicine, e.g. in diagnostic kits, in microscopy or in drug screening. Fluorescent dyes are characterized by a number of parameters allowing a user to select a suitable dye depending on the desired purpose. Parameters of interest include the excitation wavelength maximum, the emission wavelength maximum, the Stokes shift, the extinction coefficient, the fluorescence quantum yield and the fluorescence lifetime. Dyes may be selected according to the application of interest in order to, e.g., allow penetration of exciting radiation into biological samples, to minimize background fluorescence and/or to achieve a high signal-to-noise ratio.

Molecular recognition involves the specific binding of two molecules. Molecules which have binding specificity for a target biomolecule find use in a variety of research and diagnostic applications, such as the labelling and separation of analytes, flow cytometry, in situ hybridization, enzyme-linked immunosorbent assays (ELISAs), western blot analysis, magnetic cell separations and chromatography. Target biomolecules may be detected by labelling with a fluorescent dye.

SUMMARY

Water solvated polymeric dyes and polymeric tandem dyes having a blue excitation spectrum are provided. The polymeric dyes are conjugated polymers that can include a thiophene-containing co-monomer. The polymeric tandem dyes further include a signaling chromophore covalently linked to the conjugated polymer in energy-receiving proximity therewith. Also provided are labelled specific binding members that include the subject polymeric dyes. Methods of evaluating a sample for the presence of a target analyte and methods of labelling a target molecule in which the subject polymeric dyes find use are also provided. Systems and kits for practicing the subject methods are also provided.

BRIEF DESCRIPTION OF THE FIGURES

It is understood that the drawings, described below, are for illustration purposes only. The drawings are not intended to limit the scope of the present teachings in any way.

DEFINITIONS

Figure 1:
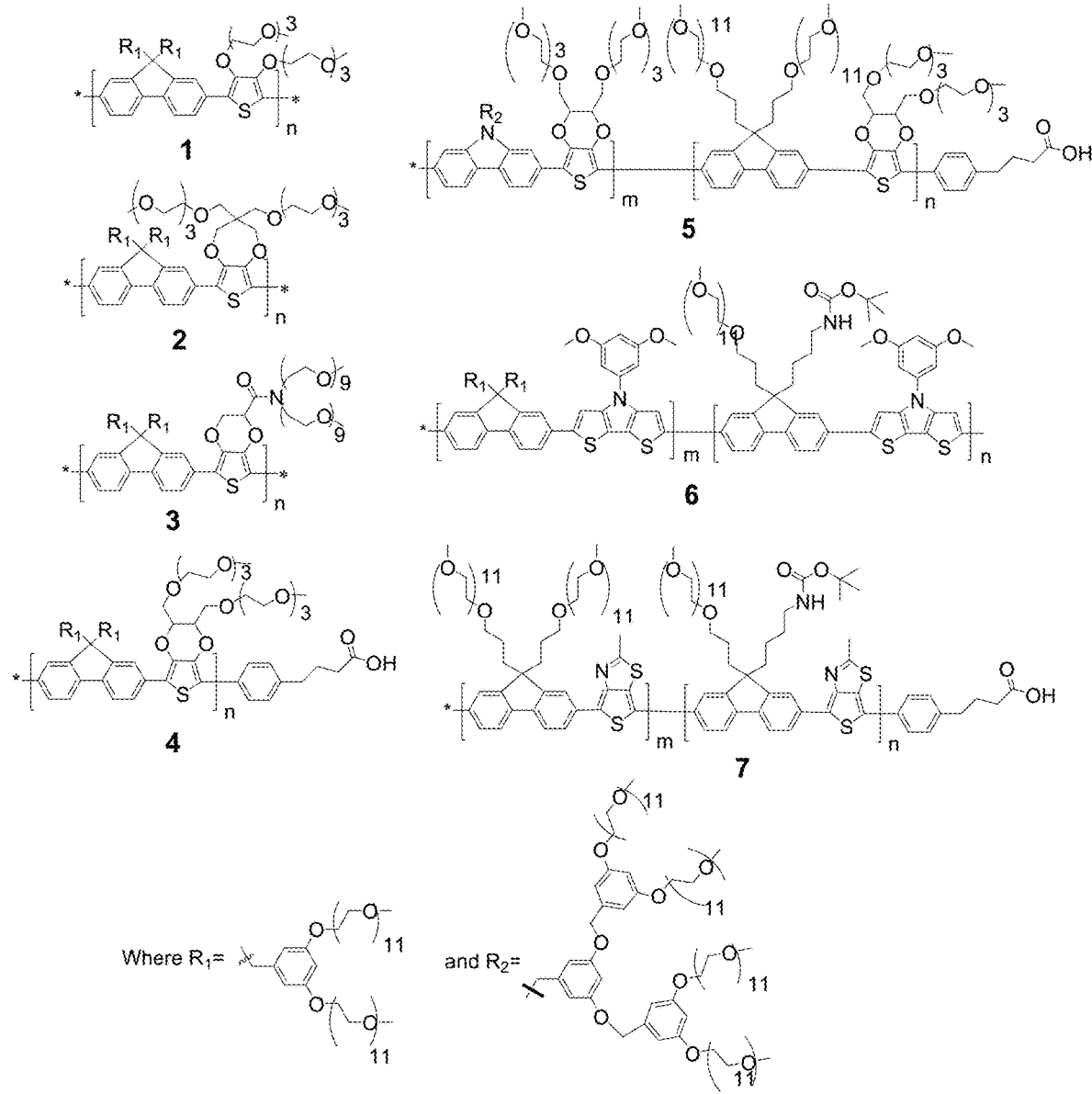
FIG. 1 shows structures of exemplary polymeric dyes 1-7 of the present disclosure.

Before describing exemplary embodiments in greater detail, the following definitions are set forth to illustrate and define the meaning and scope of the terms used in the description.

Unless defined otherwise, all technical and scientific terms used herein have the same meaning as commonly understood by one of ordinary skill in the art to which this invention belongs. Still, certain terms are defined below for the sake of clarity and ease of reference.

It must be noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

As used herein, the term "sample" relates to a material or mixture of materials, in some cases in liquid form, containing one or more analytes of interest. In some embodiments, the term as used in its broadest sense, refers to any plant, animal or bacterial material containing cells or producing cellular metabolites, such as, for example, tissue or fluid isolated from an individual (including without limitation plasma, serum, cerebrospinal fluid, lymph, tears, saliva and tissue sections) or from in vitro cell culture constituents, as well as samples from the environment. The term "sample" may also refer to a "biological sample". As used herein, the term "a biological sample" refers to a whole organism or a subset of its tissues, cells or component parts (e.g. body fluids, including, but not limited to, blood, mucus, lymphatic fluid, synovial fluid, cerebrospinal fluid, saliva, amniotic fluid, amniotic cord blood, urine, vaginal fluid and semen). A "biological sample" can also refer to a homogenate, lysate or extract prepared from a whole organism or a subset of its tissues, cells or component parts, or a fraction or portion thereof, including but not limited to, plasma, serum, spinal fluid, lymph fluid, the external sections of the skin, respiratory, intestinal, and genitourinary tracts, tears, saliva, milk, blood cells, tumors and organs. In certain embodiments, the sample has been removed from an animal or plant. Biological samples may include cells. The term "cells" is used in its conventional sense to refer to the basic structural unit of living organisms, both eukaryotic and prokaryotic, having at least a nucleus and a cell membrane. In certain embodiments, cells include prokaryotic cells, such as from bacteria. In other embodiments, cells include eukaryotic cells, such as cells obtained from biological samples from animals, plants or fungi.

As used herein, the terms "support bound" and "linked to a support" are used interchangeably and refer to a moiety (e.g., a specific binding member) that is linked covalently or non-covalently to a support of interest. Covalent linking may involve the chemical reaction of two compatible functional groups (e.g., two chemoselective functional groups, an electrophile and a nucleophile, etc.) to form a covalent bond between the two moieties of interest (e.g. a support and a specific binding member). In some cases, non-covalent linking may involve specific binding between two moieties of interest (e.g., two affinity moieties such as a hapten and an antibody or a biotin moiety and a streptavidin, etc.). In certain cases, non-covalent linking may involve absorption to a substrate.

As used herein, the term "polypeptide" refers to a polymeric form of amino acids of any length, including peptides that range from 2-50 amino acids in length and polypeptides that are greater than 50 amino acids in length. The terms "polypeptide" and "protein" are used interchangeably herein. The term "polypeptide" includes polymers of coded and non-coded amino acids, chemically or biochemically modified or derivatized amino acids, and polypeptides having modified peptide backbones in which the conventional backbone has been replaced with non-naturally occurring or synthetic backbones. A polypeptide may be of any convenient length, e.g., 2 or more amino acids, such as 4 or more amino acids, 10 or more amino acids, 20 or more amino acids, 50 or more amino acids, 100 or more amino acids, 300 or more amino acids, such as up to 500 or 1000 or more amino acids. "Peptides" may be 2 or more amino acids, such as 4 or more amino acids, 10 or more amino acids, 20 or more amino acids, such as up to 50 amino acids. In some embodiments, peptides are between 5 and 30 amino acids in length.

As used herein the term "isolated," refers to a moiety of interest that is at least 60% free, at least 75% free, at least 90% free, at least 95% free, at least 98% free, and even at least 99% free from other components with which the moiety is associated with prior to purification.

A "plurality" contains at least 2 members. In certain cases, a plurality may have 10 or more, such as 100 or more, 1000 or more, 10,000 or more, 100,000 or more, $10^6$ or more, $10^7$ or more, $10^8$ or more or $10^9$ or more members.

Numeric ranges are inclusive of the numbers defining the range.

As used herein, the term "specific binding" refers to the ability of a capture agent (or a first member of a specific binding pair) to preferentially bind to a particular analyte (or a second member of a specific binding pair) that is present, e.g., in a homogeneous mixture of different analytes. In some instances, a specific binding interaction will discriminate between desirable and undesirable analytes in a sample with a specificity of 10-fold or more for a desirable analyte over an undesirable analytes, such as 100-fold or more, or 1000-fold or more. In some cases, the affinity between a capture agent and analyte when they are specifically bound in a capture agent/analyte complex is at least $10^{-8}$M, at least $10^{-9}$M, such as up to $10^{-10}$M.

As used herein, the terms "affinity" and "avidity" have the same meaning and may be used interchangeably herein. "Affinity" refers to the strength of binding, increased binding affinity being correlated with a lower Kd.

The methods described herein include multiple steps. Each step may be performed after a predetermined amount of time has elapsed between steps, as desired. As such, the time between performing each step may be 1 second or more, 10 seconds or more, 30 seconds or more, 60 seconds or more, 5 minutes or more, 10 minutes or more, 60 minutes or more and including 5 hours or more. In certain embodiments, each subsequent step is performed immediately after completion of the previous step. In other embodiments, a step may be performed after an incubation or waiting time after completion of the previous step, e.g., a few minutes to an overnight waiting time.

As used herein, the terms "evaluating", "determining," "measuring," and "assessing," and "assaying" are used interchangeably and include both quantitative and qualitative determinations.

The term "separating", as used herein, refers to physical separation of two elements (e.g., by size or affinity, etc.) as well as degradation of one element, leaving the other intact.

As used herein, the term "linker" or "linkage" refers to a linking moiety that connects two groups and has a backbone of 100 atoms or less in length. A linker or linkage may be a covalent bond that connects two groups or a chain of between 1 and 100 atoms in length, for example a chain of 1, 2, 3, 4, 5, 6, 8, 10, 12, 14, 16, 18, 20 or more carbon atoms in length, where the linker may be linear, branched, cyclic or a single atom. In some cases, the linker is a branching linker that refers to a linking moiety that connects three or more groups. In certain cases, one, two, three, four or five or more carbon atoms of a linker backbone may be optionally substituted with a sulfur, nitrogen or oxygen heteroatom. In some cases, the linker backbone includes a linking functional group, such as an ether, thioether, amino, amide, sulfonamide, carbamate, thiocarbamate, urea, thiourea, ester, thioester or imine. The bonds between backbone atoms may be saturated or unsaturated, and in some cases not more than one, two, or three unsaturated bonds are present in a linker backbone. The linker may include one or more substituent groups, for example with an alkyl, aryl or alkenyl group. A linker may include, without limitations, polyethylene glycol; ethers, thioethers, tertiary amines, alkyls, which may be straight or branched, e.g., methyl, ethyl, n-propyl, 1-methylethyl (iso-propyl), n-butyl, n-pentyl, 1,1-dimethylethyl (t-butyl), and the like. The linker backbone may include a cyclic group, for example, an aryl, a heterocycle or a cycloalkyl group, where 2 or more atoms, e.g., 2, 3 or 4 atoms, of the cyclic group are included in the backbone. A linker may be cleavable or non-cleavable.

As used herein, the terms "polyethylene oxide", "PEO", "polyethylene glycol" and "PEG" are used interchangeably and refer to a polymeric group including a chain described by the formula $-(CH_2-CH_2-O-)_n-$ or a derivative thereof. In some embodiments, "n" is 5000 or less, such as 1000 or less, 500 or less, 200 or less, 100 or less, 50 or less, 40 or less, 30 or less, 20 or less, 15 or less, such as 3 to 15, or 10 to 15. It is understood that the PEG polymeric group may be of any convenient length and may include a variety of terminal groups and/or further substituent groups, including but not limited to, alkyl, aryl, hydroxyl, amino, acyl, acyloxy, and amido terminal and/or substituent groups. PEG groups that may be adapted for use in the subject multichromophores include those PEGs described by S. Zalipsky in "Functionalized poly(ethylene glycol) for preparation of biologically relevant conjugates", Bioconjugate Chemistry 1995, 6 (2), 150-165; and by Zhu et al in "Water-Soluble Conjugated Polymers for Imaging, Diagnosis, and Therapy", Chem. Rev., 2012, 112 (8), pp 4687-4735.

As used herein, the term "alkyl" by itself or as part of another substituent refers to a saturated branched or straight-chain monovalent hydrocarbon radical derived by the removal of one hydrogen atom from a single carbon atom of a parent alkane. Alkyl groups of interest include, but are not limited to, methyl; ethyl, propyls such as propan-1-yl or propan-2-yl; and butyls such as butan-1-yl, butan-2-yl, 2-methyl-propan-1-yl or 2-methyl-propan-2-yl. In some embodiments, an alkyl group includes from 1 to 20 carbon atoms. In some embodiments, an alkyl group includes from 1 to 10 carbon atoms. In certain embodiments, an alkyl group includes from 1 to 6 carbon atoms, such as from 1 to 4 carbon atoms. This term includes, by way of example, linear and branched hydrocarbyl groups such as methyl ($CH_3-$), ethyl ($CH_3CH_2-$), n-propyl ($CH_3CH_2CH_2-$), isopropyl (($CH_3)_2CH-$), n-butyl ($CH_3CH_2CH_2CH_2-$), isobutyl (($CH_3)_2CHCH_2-$), sec-butyl (($CH_3)(CH_3CH_2)CH-$), t-butyl (($CH_3)_3C-$), n-pentyl ($CH_3CH_2CH_2CH_2CH_2-$), and neopentyl (($CH_3)_3CCH_2-$).

The term "substituted alkyl" refers to an alkyl group as defined herein wherein one or more carbon atoms in the alkyl chain have been optionally replaced with a heteroatom such as $-O-$, $-N-$, $-S-$, $-S(O)_n-$ (where n is 0 to 2), $-NR-$ (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R' and R" may be the same or different and are chosen from hydrogen, optionally substituted alkyl, cycloalkyl, alkenyl, cycloalkenyl, alkynyl, aryl, heteroaryl and heterocyclic.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

"Amino" refers to the group —NH$_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

"Aryl" by itself or as part of another substituent refers to a monovalent aromatic hydrocarbon radical derived by the removal of one hydrogen atom from a single carbon atom of an aromatic ring system. Aryl groups of interest include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In certain embodiments, an aryl group includes from 6 to 20 carbon atoms. In certain embodiments, an aryl group includes from 6 to 12 carbon atoms. Examples of an aryl group are phenyl and naphthyl.

"Heteroaryl" by itself or as part of another substituent, refers to a monovalent heteroaromatic radical derived by the removal of one hydrogen atom from a single atom of a heteroaromatic ring system. Heteroaryl groups of interest include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, triazole, benzotriazole, thiophene, triazole, xanthene, benzodioxole and the like. In certain embodiments, the heteroaryl group is from 5-20 membered heteroaryl. In certain embodiments, the heteroaryl group is from 5-10 membered heteroaryl. In certain embodiments, heteroaryl groups are those derived from thiophene, pyrrole, benzothiophene, benzofuran, indole, pyridine, quinoline, imidazole, oxazole and pyrazine.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 20 ring atoms, including 1 to 10 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$— moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

The term "alkaryl" or "aralkyl" refers to the groups -alkylene-aryl and substituted alkylene-aryl where alkylene, substituted alkylene and aryl are defined herein.

"Alkylene" refers to divalent aliphatic hydrocarbyl groups preferably having from 1 to 6 and more preferably 1 to 3 carbon atoms that are either straight-chained or branched, and which are optionally interrupted with one or more groups selected from —O—, —NR$^{10}$—, —NR$^{10}$C(O)—, —C(O)NR$^{10}$— and the like. This term includes, by way of example, methylene (—CH$_2$—), ethylene (—CH$_2$CH$_2$—), n-propylene (—CH$_2$CH$_2$CH$_2$—), iso-propylene (—CH$_2$CH(CH$_3$)—), (—C(CH$_3$)$_2$CH$_2$CH$_2$—), (—C(CH$_3$)$_2$CH$_2$C(O)—), (—C(CH$_3$)$_2$CH$_2$C(O)NH—), (—CH(CH$_3$)CH$_2$—), and the like. "Substituted alkylene" refers to an alkylene group having from 1 to 3 hydrogens replaced with substituents as described for carbons in the definition of "substituted" below.

"Substituted" refers to a group in which one or more hydrogen atoms are independently replaced with the same or different substituent(s). Substituents of interest include, but are not limited to, alkylenedioxy (such as methylenedioxy), -M, —$R^{60}$, —$O^-$, =O, —$OR^{60}$, —$SR^{60}$, —$S^-$, =S, —$NR^{60}R^{61}$, =$NR^{60}$, —$CF_3$, —CN, —OCN, —SCN, —NO, —$NO_2$, =$N_2$, —$N_3$, —$S(O)_2O^-$, —$S(O)_2OH$, —$S(O)_2R^{60}$, —$OS(O)_2O^-$, —$OS(O)_2R^{60}$, —$P(O)(O^-)_2$, —$P(O)(OR^{60})(O^-)$, —$OP(O)(OR^{60})(OR^{61})$, —$C(O)R^{60}$, —$C(S)R^{60}$, —$C(O)OR^{60}$, —$C(O)NR^{60}R^{61}$, —$C(O)O^-$, —$C(S)OR^{60}$, —$NR^{62}C(O)NR^{60}R^{61}$, —$NR^{62}C(S)NR^{60}R^{61}$, —$NR^{62}C(NR^{63})NR^{60}R^{61}$ and —$C(NR^{62})NR^{60}R^{61}$ where M is halogen; $R^{60}$, $R^{61}$, $R^{62}$ and $R^{63}$ are independently hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl or substituted heteroaryl, or optionally $R^{60}$ and $R^{61}$ together with the nitrogen atom to which they are bonded form a cycloheteroalkyl or substituted cycloheteroalkyl ring; and $R^{64}$ and $R^{65}$ are independently hydrogen, alkyl, substituted alkyl, aryl, cycloalkyl, substituted cycloalkyl, cycloheteroalkyl, substituted cycloheteroalkyl, aryl, substituted aryl, heteroaryl or substituted heteroaryl, or optionally $R^{64}$ and $R^{65}$ together with the nitrogen atom to which they are bonded form a cycloheteroalkyl or substituted cycloheteroalkyl ring. In certain embodiments, substituents include -M, —$R^{60}$, =O, —$OR^{60}$, —$SR^{60}$, —$S^-$, =S, —$NR^{60}R^{61}$, =$NR^{60}$, —$CF_3$, —CN, —OCN, —SCN, —NO, —$NO_2$, =$N_2$, —$N_3$, —$S(O)_2R^{60}$, —$OS(O)_2O^-$, —$OS(O)_2R^{60}$, —$P(O)(O^-)_2$, —$P(O)(OR^{60})(O^-)$, —$OP(O)(OR^{60})(OR^{61})$, —$C(O)R^{60}$, —$C(S)R^{60}$, —$C(O)OR^{60}$, —$C(O)NR^{60}R^{61}$, —$C(O)O^-$, —$NR^{62}C(O)NR^{60}R^{61}$. In certain embodiments, substituents include -M, —$R^{60}$, =O, —$OR^{60}$, —$SR^{60}$, —$NR^{60}R^{61}$, —$CF_3$, —CN, —$NO_2$, —$S(O)_2R^{60}$, —$P(O)(OR^{60})(O^-)$, —$OP(O)(OR^{60})(OR^{61})$, —$C(O)R^{60}$, —$C(O)OR^{60}$, —$C(O)NR^{60}R^{61}$, —$C(O)O^-$. In certain embodiments, substituents include -M, —$R^{60}$, =O, —$OR^{60}$, —$SR^{60}$, —$NR^{60}R^{61}$, —$CF_3$, —CN, —$NO_2$, —$S(O)_2R^{60}$, —$OP(O)(OR^{60})(OR^{61})$, —$C(O)R^{60}$, —$C(O)OR^{60}$, —$C(O)O^-$, where $R^{60}$, $R^{61}$ and $R^{62}$ are as defined above. For example, a substituted group may bear a methylenedioxy substituent or one, two, or three substituents selected from a halogen atom, a (1-4C)alkyl group and a (1-4C)alkoxy group. When the group being substituted is an aryl or heteroaryl group, the substituent(s) (e.g., as described herein) may be referred to as "aryl substituent(s)".

Other definitions of terms may appear throughout the specification.

DETAILED DESCRIPTION

As summarized above, water solvated polymeric dyes and polymeric tandem dyes having a blue excitation spectrum are provided. The polymeric dyes can be conjugated polymers that include a thiophene-containing co-monomer. The polymeric tandem dyes further include a signaling chromophore covalently linked to the multichromophore in energy-receiving proximity therewith. Also provided are labelled specific binding members that include the subject polymeric dyes. Methods of evaluating a sample for the presence of a target analyte and methods of labelling a target molecule in which the subject polymeric dyes find use are also provided. Systems and kits for practicing the subject methods are also provided.

Before the various embodiments are described in greater detail, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

In further describing the subject invention, polymeric dyes including light harvesting multichromophores and related polymeric tandem dyes further including a signaling chromophore are described first in greater detail. Next, labelled specific binding members which include the subject polymeric dyes are described. Then, methods of interest in which the subject polymeric dyes find use are reviewed. Systems and kits that may be used in practicing methods of the present disclosure are also described.

Polymeric Dyes

As summarized above, the present disclosure provides water solvated polymeric dyes having a blue excitation spectrum. The subject polymeric dyes can be pi-conjugated polymers including thiophene-based co-monomers. The polymer can be an alternating co-polymer or a random co-polymer of co-monomers. In some instances, the subject polymeric dyes provide narrow absorption peak width relative to other dyes of interest. In multi-color applications, being able to use multiple excitation sources is critical to achieving multiplicity and a high number of parameters. As peak widths narrow, the amount of excitation by sources other than the wavelength intended decreases. In addition to narrow peak width, minimizing absorption at other common excitation sources is critical for higher parameter experiments. The degree of cross-source excitation can be tuned for the subject polymeric dyes by selection of a particular structure, co-monomers, and mixtures of co-blocks.

The subject polymeric dyes feature termini on the conjugated polymer chains that can include a free chemoselective functional group that provides for bioconjugation. In some cases, such functionality is referred to as an end linker. With these end linkers, a covalent bond can be formed to attach a biomolecule such as an antibody, a polynucleotide, or aptamer. For example, polymeric dye-labeled antibodies find use in flow cytometry as reagents exhibiting high brightness. Additionally, orthogonal chemoselective functional groups can be installed along the conjugated polymer chain that can be used for either bioconjugation or the attachment of acceptor signaling chromophores in donor-acceptor polymeric tandem dyes.

As used herein, the terms "light harvesting multichromophore", "polymeric dye" and "conjugated polymer" are used interchangeably and refer to a conjugated polymer which has a structure capable of harvesting light with a particular absorption maximum wavelength and converting it to emitted light at a longer emission maximum wavelength. In some cases, the light harvesting multichromophore is itself fluorescent. Conjugated polymers (CPs) are characterized by a delocalized electronic structure and may have an effective conjugation length that is substantially shorter than the length of the polymer chain, because the backbone may contain a large number of conjugated segments in close proximity. In some cases, conjugated polymers are efficient for light harvesting and provide for optical amplification via Forster energy transfer to an acceptor.

As used herein the term "unit" refers to a structural subunit of a polymer. The term unit is meant to include monomers, co-monomers, co-blocks, conjugated segments, repeating units, and the like. A "repeating unit" is a subunit of a polymer that is defined by the minimum number of distinct structural features that are required for the unit to be considered monomeric, such that when the unit is repeated n times, the resulting structure describes the polymer or a block thereof. In some cases, the polymer may include two or more different repeating units, e.g., when the polymer is a multiblock polymer or a random arrangement of units, each block may define a distinct repeating unit, e.g., an n-block and a m-block. It is understood that a variety of arrangements of n and/or m repeating units or blocks are possible and that in the depicted formula of the subject multichromophores described herein any convenient linear arrangements of n and m co-blocks of various lengths are included within the structure of the overall polymer. In some cases, a repeating unit of the polymer includes a single monomer group. In certain instances, a repeating unit of the polymer includes two or more monomer groups, i.e., co-monomer groups, such as two, three, four or more co-monomer groups. As used herein, the term "co-monomer" or "co-monomer group" refers to a structural unit of a polymer that may itself be part of a repeating unit of the polymer.

In some embodiments, the conjugated polymer includes a block copolymer that is composed of blocks of polymerized monomers. In such cases, the block copolymer may be described as having distinct repeating units each corresponding to a distinct co-block of the polymer. In some cases, the polymer is a diblock copolymer that contains two different co-blocks. In such cases, the polymer may be described as including co-blocks, where each co-block may be composed of co-monomers, such as one, two, three or more co-monomers.

The multichromophore may have any convenient length. In some cases, the particular number of monomeric repeating units or segments of the multichromophore may fall within the range of 2 to 500,000, such as 2 to 100,000, 2 to 30,000, 2 to 10,000, 2 to 3,000 or 2 to 1,000 units or segments, or such as 5 to 100,000, 10 to 100,000, 100 to 100,000, 200 to 100,000, or 500 to 50,000 units or segments. In some instances, the particular number of monomeric repeating units or segments of the multichromophore may fall within the range of 2 to 1,000, such as 2 to 500, 2 to 100, 3 to 100, 4 to 100, 5 to 100, 6 to 100, 7 to 100, 8 to 100, 9 to 100 or 10 to 100 units or segments.

The multichromophore may be of any convenient molecular weight (MW). In some cases, the MW of the multichromophore may be expressed as an average molecular weight. In some instances, the polymeric dye has an average molecular weight in the range of 500 to 500,000, such as from 1,000 to 100,000, from 2,000 to 100,000, from 10,000 to 100,000 or even an average molecular weight in the range of 50,000 to 100,000.

The subject polymeric dyes can include a certain minimum content of thiophene-containing co-monomers that can provide for a desirable spectroscopic property of interest. The content (e.g., mol % values) of thiophene-containing co-monomers in the polymeric dyes (e.g., as described herein) can be measured and referred to according to a particular thiophene-containing co-monomer or according to the cumulative total of all thiophene-containing co-monomers in the polymeric dyes. In some embodiments, the multichromophore includes a thiophene-containing co-monomer(s) that constitutes 5% or more by molarity (e.g., 5 mol %) of the multichromophore, such as 10% or more, 15% or more, 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, or even more by molarity of the multichromophore. In such cases, the multichromophore may include 5 or more repeating units, such as 10 or more, 20 or more, 30 or more, 40 or more, 50 or more, 60 or more, 70 or more, 80 or more, 90 or more, 100 or more, 200 or more, 500 or more, 1000 or more, 10,000 or more, or even more repeating units. In such cases, the multichromophore may include 5 or more co-monomer units, such as 10 or more, 20 or more, 30 or more, 40 or more, 50 or more, 60 or more, 70 or more, 80 or more, 90 or more, 100 or more, 200 or more, 500 or more, 1000 or more, 10,000 or more, or even more co-monomer units. In certain embodiments, the thiophene-containing co-monomer(s) of interest constitutes 25% or more by molarity of the multichromophore, such as 30% or more, 40% or more, 45% or more, 50% or more, or even more by molarity of the multichromophore, which includes 5 or more repeating units, such as 10 or more, 20 or more, 30 or more, 40 or more, 50 or more, 60 or more, 70 or more, 80 or more, 90 or more, 100 or more repeating units.

In some embodiments, the multichromophore includes a plurality of first optically active units forming a conjugated system, having an absorption wavelength (e.g., as described herein) at which the first optically active units absorb light to form an excited state. In certain instances, the multichromophore includes a conjugated polymer segment or an oligomeric structure including bandgap-lowering n-conjugated repeating units.

The subject multichromophore may have one or more desirable spectroscopic properties, such as a particular absorption maximum wavelength, a particular emission maximum wavelength, extinction coefficient, quantum yield, and the like. The subject polymeric dyes and polymeric tandem dyes provide for a variety of absorption and emission profiles which depend on a variety of factors such as the selected co-monomers, linking groups, substituents and optional linked signaling chromophores of which the polymers are composed.

The subject water solvated polymeric dyes have a blue excitation spectrum. As used herein, a blue excitation spectrum is an excitation spectrum having a full width at half maximum (FWHM) located in the range of 375 nm to 575 nm. Full width at half maximum (FWHM) is an expression of the extent of a function given by the difference between the two extreme values of the independent variable at which the dependent variable is equal to half of its maximum value. In other words, it is the width (a difference or range of two particular wavelengths) of an excitation spectrum curve measured between those points on the y-axis which are half the maximum amplitude. In some instances, the FWHM can be referred to as the difference between the wavelengths. In some instances, the FWHM can be referred to in reference to a particular region of the spectrum within which the wavelengths defining the FWHM are located and measured.

In certain embodiments, the polymeric dye has a blue excitation spectrum having a full width at half maximum (FWHM) located in the range of 375 nm to 550 nm. In certain embodiments, the polymeric dye has a blue excitation spectrum having a full width at half maximum (FWHM) located in the range of 375 nm to 525 nm. In certain embodiments, the polymeric dye has a blue excitation spectrum having a full width at half maximum (FWHM) located in the range of 375 nm to 500 nm. In certain embodiments, the polymeric dye has a blue excitation spectrum having a full width at half maximum (FWHM) located in the range of 375 nm to 475 nm. In certain embodiments, the polymeric dye has a blue excitation spectrum having a full width at half maximum (FWHM) located in the range of 375 nm to 450 nm. In certain embodiments, the polymeric dye has a blue excitation spectrum having a full width at half maximum (FWHM) located in the range of 400 nm to 575 nm. In certain embodiments, the polymeric dye has a blue excitation spectrum having a full width at half maximum (FWHM) located in the range of 410 nm to 575 nm. In certain embodiments, the polymeric dye has a blue excitation spectrum having a full width at half maximum (FWHM) located in the range of 420 nm to 575 nm. In certain embodiments, the polymeric dye has a blue excitation spectrum having a full width at half maximum (FWHM) located in the range of 430 nm to 575 nm. In certain embodiments, the polymeric dye has a blue excitation spectrum having a full width at half maximum (FWHM) located in the range of 440 nm to 575 nm. In certain embodiments, the polymeric dye has a blue excitation spectrum having a full width at half maximum (FWHM) located in the range of 450 nm to 575 nm. In certain embodiments, the polymeric dye has a blue excitation spectrum having a full width at half maximum (FWHM) located in the range of 460 nm to 575 nm. In some instances, the water solvated polymeric dyes have a blue excitation spectrum having a FWHM of 200 nm or less, such as 180 nm or less, 175 nm or less, 170 nm or less, 160 nm or less, 150 nm or less, 140 nm or less, 130 nm or less, 120 nm or less, 110 nm or less, 100 nm or less, or even less.

In some cases, the polymeric dye absorption maximum wavelength is in the range of 375 to 575 nm, such as 400 nm to 550 nm, 410 nm to 550 nm, 420 nm to 540 nm, 430 nm to 540 nm or 440 nm to 530 nm. In certain embodiments, the multichromophore has an absorption maximum wavelength of 550 nm or less, such as 525 nm or less, 500 nm or less, 490 nm or less, 480 nm or less, 470 nm or less, 460 nm or less, 450 nm or less, 425 nm or less, or even less. In certain instances, the multichromophore has an absorption maximum wavelength in the range of 375 nm to 440 nm. In certain instances, the multichromophore has an absorption maximum wavelength in the range of 400 nm to 450 nm. In certain instances, the multichromophore has an absorption maximum wavelength in the range of 450 nm to 500 nm. In certain instances, the multichromophore has an absorption maximum wavelength in the range of 500 nm to 550 nm. In some instances, the polymeric dyes disclosed herein can provide an absorption maximum wavelength in the range from 440 nm to 530 nm. In certain cases, the polymeric dyes provide high extinction coefficients and high quantum yields that yield bright fluorescent reagents. In certain instances, the polymeric dye has no yellow-green absorption. In some instances, the polymeric dye has no absorption at 562 nm or greater, such as 570 nm or greater, 580 nm or greater, 590 nm or greater, 600 nm or greater, 610 nm or greater, or 620 nm or greater.

In certain instances, the multichromophore has an absorption maximum wavelength of 380 nm±5 nm. In certain instances, the multichromophore has an absorption maximum wavelength of 390 nm±5 nm. In certain instances, the multichromophore has an absorption maximum wavelength of 400 nm±5 nm. In certain instances, the multichromophore has an absorption maximum wavelength of 410 nm±5 nm. In certain instances, the multichromophore has an absorption maximum wavelength of 420 nm±5 nm. In certain instances, the multichromophore has an absorption maximum wavelength of 430 nm±5 nm. In certain instances, the multichromophore has an absorption maximum wavelength of 440 nm±5 nm. In certain instances, the multichromophore has an absorption maximum wavelength of 450 nm±5 nm. In certain instances, the multichromophore has an absorption maximum wavelength of 460 nm±5 nm. In certain instances, the multichromophore has an absorption maximum wavelength of 470 nm±5 nm. In certain instances, the multichromophore has an absorption maximum wavelength of 480 nm±20 nm. In certain instances, the multichromophore has an absorption maximum wavelength of 480 nm±10 nm. In certain instances, the multichromophore has an absorption maximum wavelength of 480 nm±5 nm. In certain instances, the multichromophore has an absorption maximum wavelength of 490 nm±5 nm. In certain instances, the multichromophore has an absorption maximum wavelength of 500 nm±5 nm. In certain instances, the multichromophore has an absorption maximum wavelength of 510 nm±5 nm. In certain instances, the multichromophore has an absorption maximum wavelength of 520 nm±5 nm. In certain instances, the multichromophore has an absorption maximum wavelength of 530 nm±5 nm. In certain instances, the multichromophore has an absorption maximum wavelength of 540 nm±5 nm. In certain instances, the multichromophore has an absorption maximum wavelength of 550 nm±5 nm. In certain instances, the multichromophore has an absorption maximum wavelength of 560 nm±5 nm. In certain instances, the multichromophore has an absorption maximum wavelength of 570 nm±5 nm.

In some embodiments, the multichromophore has an emission maximum wavelength in the range of 300 to 900 nm, such as 350 to 850 nm, 350 to 600 nm, 360 to 500 nm, 370 to 500 nm, 380 to 500 nm, 390 to 500 nm or 400 to 500 nm, where specific examples of emission maxima of interest include, but are not limited to: 395 nm±5 nm, 460 nm±5 nm, 490 nm±5 nm, 550 nm±5 nm, 560 nm±5 nm, 605 nm±5 nm, 650 nm±5 nm, 680 nm±5 nm, 700 nm±5 nm, 805 nm±5 nm. In certain instances, the multichromophore has an emission maximum wavelength selected from the group consisting of 395 nm, 460 nm, 490 nm, 550 nm, 560 nm, 605 nm, 650 nm, 680 nm, 700 nm and 805 nm. In certain instances, the multichromophore has an emission maximum wavelength of 395 nm±5 nm. In some instances, the multichromophore itself has an emission maximum wavelength in the range of 375 to 900 nm (such as in the range of 380 nm to 900 nm, 390 nm to 900 nm, or 400 nm to 900 nm).

In some instances, the multichromophore has an extinction coefficient of $5 \times 10^5$ cm$^{-1}$ M$^{-1}$ or more, such as $6 \times 10^5$ cm$^{-1}$ M$^{-1}$ or more, $7 \times 10^5$ cm$^{-1}$ M$^{-1}$ or more, $8 \times 10^5$ cm$^{-1}$M$^{-1}$ or more, $9 \times 10^5$ cm$^{-1}$ M$^{-1}$ or more, such as $1 \times 10^6$ cm$^{-1}$ M$^{-1}$ or more, $1.5 \times 10^6$ cm$^{-1}$ M$^{-1}$ or more, $2 \times 10^6$ cm$^{-1}$ M$^{-1}$ or more, $2.5 \times 10^6$ cm$^{-1}$ M$^{-1}$ or more, $3 \times 10^6$ cm$^{-1}$ M$^{-1}$ or more, $4 \times 10^6$ cm$^{-1}$ M$^{-1}$ or more, $5 \times 10^6$ cm$^{-1}$ M$^{-1}$ or more, $6 \times 10^6$ cm$^{-1}$ M$^{-1}$ or more, $7 \times 10^6$ cm$^{-1}$ M$^{-1}$ or more, or $8 \times 10^6$ cm$^{-1}$ M$^{-1}$ or more. In such cases, the multichromophore may have 5 or more repeating units, such as 6 or more, 7 or more, 8 or more, 9 or more, 10 or more, or even more repeating units. In some embodiments, the multichromophore has a molar extinction coefficient of $5 \times 10^5$ M$^{-1}$ cm$^{-1}$ or more. In certain embodiments, the multichromophore has a molar extinction coefficient of $1 \times 10^6$ M$^{-1}$ cm$^{-1}$ or more.

In some instances, the multichromophore has an extinction coefficient of 40,000 cm$^{-1}$ M$^{-1}$ per repeating unit or more, such as 45,000 cm$^{-1}$ M$^{-1}$ per repeating unit or more, 50,000 cm$^{-1}$ M$^{-1}$ per repeating unit or more, 55,000 cm$^{-1}$ M$^{-1}$ per repeating unit or more, 60,000 cm$^{-1}$ M$^{-1}$ per repeating unit or more, 70,000 cm$^{-1}$ M$^{-1}$ per repeating unit or more, 80,000 cm$^{-1}$ M$^{-1}$ per repeating unit or more, 90,000 cm$^{-1}$ M$^{-1}$ per repeating unit or more, 100,000 cm$^{-1}$ M$^{-1}$ per repeating unit or more, or even more. In some instances, the 40,000 cm$^{-1}$ M$^{-1}$ per repeating unit or more described herein is an average extinction coefficient. In certain instances, the repeat unit of the multichromophore may include a single monomer, two co-monomers, or three or more co-monomers. In some instances, the multichromophore has an extinction coefficient of 40,000 cm$^{-1}$ M$^{-1}$ per co-monomer or more, such as 45,000 cm$^{-1}$ M$^{-1}$ per co-monomer or more, 50,000 cm$^{-1}$ M$^{-1}$ per co-monomer or more, 55,000 cm$^{-1}$ M$^{-1}$ per co-monomer or more, 60,000 cm$^{-1}$ M$^{-1}$ per co-monomer or more, 70,000 cm$^{-1}$ M$^{-1}$ per co-monomer or more, 80,000 cm$^{-1}$ M$^{-1}$ per co-monomer or more, 90,000 cm$^{-1}$ M$^{-1}$ per co-monomer or more, 100,000 cm$^{-1}$ M$^{-1}$ per co-monomer or more, or even more. In some instances, the 40,000 cm$^{-1}$ M$^{-1}$ per co-monomer or more is an average extinction coefficient.

It is understood that in some cases the subject multichromophores may include co-blocks (e.g., n and m co-blocks) or a random arrangement of n and m repeating units. The subject multichromophores may include any convenient linear arrangements of n and m co-blocks of various lengths within the structure of the overall polymer. In addition, the multichromophores may include any convenient arrangements of co-monomers within such n and/or m co-blocks. Unless indicated to the contrary, all possible arrangements of co-monomers are meant to be included in the polymeric dyes described herein. A variety of polymer synthesis methods may be utilized to prepare co-monomers and co-blocks of interest in the preparation of the subject multichromophores.

It is understood that in some cases, the polymerization methods may produce a composition including a population of conjugated polymers that includes some variation with respect to the particular length and/or terminal groups (i.e., end groups) present in each conjugated polymer of the population. The formulae depicted herein may refer to a single compound or to a population or sub-population of polymeric compounds. As used herein, * denotes a site for covalent attachment to the unsaturated backbone of a conjugated polymer.

In some embodiments, the subject polymeric dyes are pi-conjugated polymers including a thiophene-based co-monomer and an aryl or heteroaryl co-monomer. Aryl or heteroaryl co-monomers of interest include but are not limited to, fused tricyclic co-monomers, such as fluorene co-monomers, carbazole co-monomers, silole co-monomers or bridged biphenyl co-monomers. A fused tricyclic co-monomer is a co-monomer including a tricyclic aromatic group having three fused rings in a configuration where two aryl or heteroaryl 6-membered rings are fused to a central 5 or 6-membered carbocyclic or heterocyclic ring. In some cases, the fused tricyclic co-monomer includes two benzo or pyrido rings fused to a central 5 or 6 membered carbocyclic or heterocyclic ring. The fused tricyclic co-monomer can be pi-conjugated to adjacent co-monomers of a polymer backbone via any convenient ring atoms of the fused rings. The central 5- or 6-membered ring may be a carbocycle or a heterocycle, aromatic or partially saturated, and may further include a sidechain substituent, e.g., a WSG and/or a linker to a chemoselective tag. A bridged biphenyl co-monomer is a fused tricyclic co-monomer having a biphenyl group where the two phenyl rings are further linked with each other via a central 6 membered ring. In certain instances, the fused tricyclic co-monomer is described by the following structure:

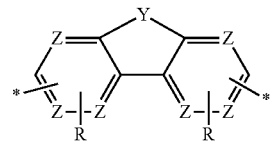

where:

Y is $C(R^3)_2$, —$C(R^3)_2C(R^3)_2$—, $NR^3$, $Si(R^3)_2$ or Se;

Z is CH, CR or N;

each $R^3$ is independently selected from H, alkyl, substituted alkyl, aryl, substituted aryl, heteroaryl, substituted heteroaryl, acyl, substituted acyl, alkoxy, substituted alkoxy, amido, substituted amido, an aralkyl, a substituted aralkyl, a PEG moiety, -$L^1$-$Z^1$, where $L^1$ is a linker and $Z^1$ is a chemoselective tag (e.g., a tag including a chemoselective functional group) and a WSG; and each R is independently H or one or more aryl or heteroaryl substituents. In some cases, each R refers to one or two ring substituents independently selected from halogen, sulfonate, alkoxy, substituted alkoxy, alkyl and substituted alkyl. In certain instances, at least two of Z in each ring is CH or CR. In certain instances, one and only one of Z in each ring is N.

In certain instances, the fused tricyclic co-monomer is described by one of the following structures:

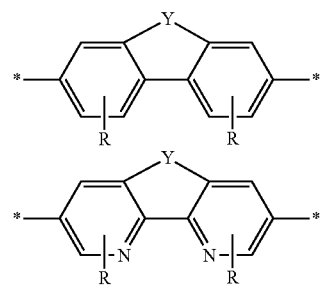

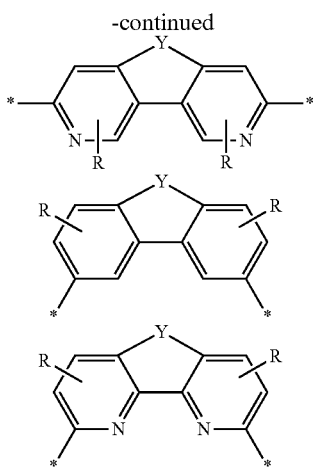

where:
  Y is $C(R^3)_2$, —$C(R^3)_2C(R^3)_2$—, $NR^3$, $Si(R^3)_2$ or Se;
  each $R^3$ is independently selected from H, alkyl, substituted alkyl, aryl, substituted aryl, heteroaryl, substituted heteroaryl, acyl, substituted acyl, alkoxy, substituted alkoxy, amido, substituted amido, an aralkyl, a substituted aralkyl, a PEG moiety, -$L^1$-$Z^1$, where $L^1$ is a linker and $Z^1$ is a chemoslective tag (e.g., a tag including a chemoslective functional group) and a WSG; and each R is independently H, $R^3$ or one or more aryl or heteroaryl substituents. In some cases, each R refers to one or two ring substituents independently selected from halogen, sulfonate, alkoxy, substituted alkoxy, alkyl and substituted alkyl. The symbol "*" denotes a site for covalent attachment to the unsaturated backbone of a conjugated polymer, e.g., a π conjugated segment, a terminal group, a linker and a linked specific binding member. It is understood that for any of the formulae described herein which includes a 2,7-pi-conjugated fused tricyclic co-monomer, an analogous formula including an analogous 3,6-pi-conjugated co-monomer could also be depicted. In certain cases, the fused tricyclic co-monomer is a fluorene co-monomer where Y is $C(R^3)_2$. In some cases, the fused tricyclic co-monomer is a carbazole co-monomer where Y is $NR^3$. In some cases, the fused tricyclic co-monomer is a silole co-monomer where Y is $Si(R^3)_2$.

In some cases, the fused tricyclic co-monomer is a bridged biphenyl co-monomer where Y is —$C(R^3)_2C(R^3)_2$—. In some cases, the fused tricyclic co-monomer is a bridged biphenyl co-monomer where Y is —$CHR^3CHR^3$—. In certain instances of any of the fused tricyclic co-monomers described herein, each R is independently selected from H, halogen, alkoxy, substituted alkoxy, alkyl and substituted alkyl. In certain cases, each R is independently selected from H, fluoro, chloro, methoxy, substituted alkoxy, alkyl and substituted alkyl.

In certain instances, the fused tricyclic co-monomer is described by one of the following structures:

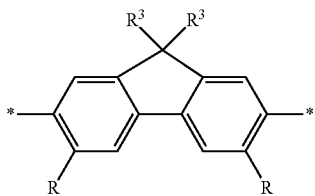

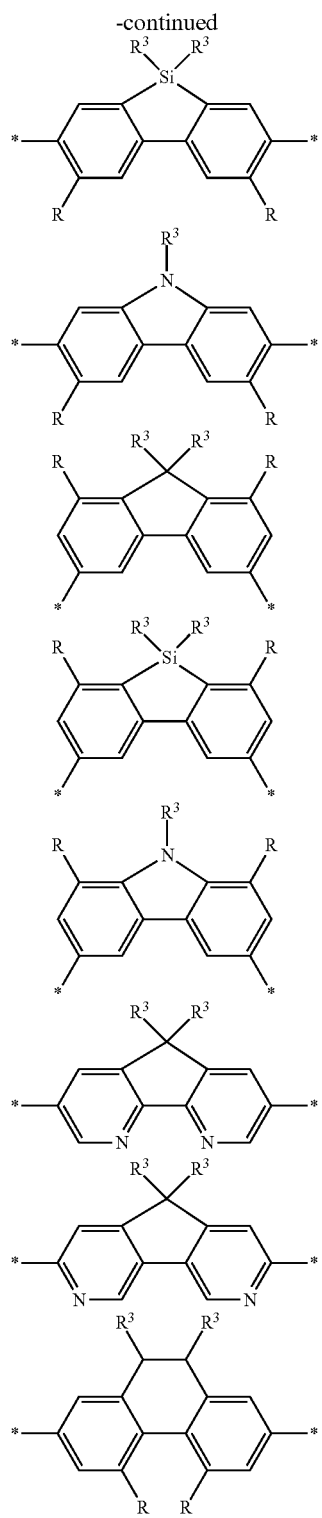

wherein:
  each $R^3$ is independently selected from H, alkyl, substituted alkyl, aryl, substituted aryl, heteroaryl, substituted heteroaryl, acyl, substituted acyl, alkoxy, substituted alkoxy, amido, substituted amido, an aralkyl, a substituted aralkyl, a PEG moiety, -$L^1$-$Z^1$, where $L^1$ is a linker and $Z^1$ is a chemoslective tag (e.g., a tag including a chemoslective functional group) and a WSG; and each R is independently H, R³ or one or more aryl or heteroaryl substituents. In some cases, each R refers to one or two ring substituents independently selected from halogen, sulfonate, alkoxy, substituted alkoxy, alkyl and substituted alkyl. In some cases, each R is fluoro or methoxy. In some cases, at least one R³ is a WSG. In some cases, at least one R³ is -L¹-Z¹.

In some instances, the multichromophore includes a conjugated segment having the structure of formula (I):

of formula (I), Y² is —CHR³CHR³—. In some embodiments of formula (I), Y² is Se. In certain instances of formula (I), Y³ is C(R³)₂ wherein one R³ comprises Z¹. In some cases of formula (I), Y³ is NR³ wherein R³ comprises Z¹. In certain cases of formula (I), Y³ is Si(R³)₂ wherein one R³ comprises Z¹. In certain cases of formula (I), Y³ is —C(R³)₂C(R³)₂—, wherein one R³ comprises Z¹. In some cases of formula (I), Y³ is —CHR³CHR³— wherein one R³ comprises Z¹. In certain embodiments of formula (I), Z¹ is a chemoselective

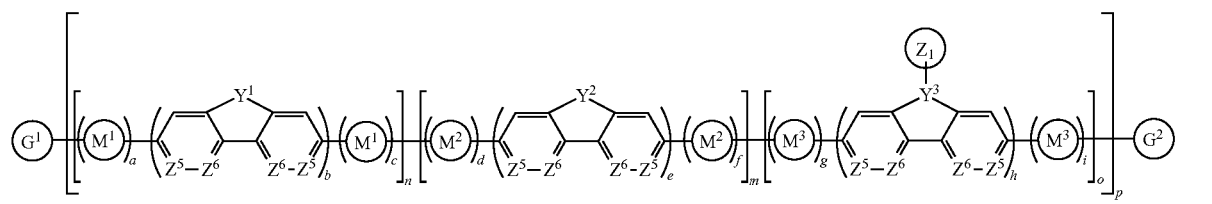

wherein:
M¹, M² and M³ are independently an aryl or heterocyclic co-monomer wherein at least one of M¹, M² and M³ is a thiophene containing co-monomer;
Z¹ is a chemoselective functional group or a linked signaling chromophore;
Z⁵ and Z⁶ are independently CR or N where R is selected from H, halogen, alkoxy, substituted alkoxy, alkyl and substituted alkyl;
G¹ and G² are each independently selected from a terminal group, a n conjugated segment, a linker and a linked specific binding member;
Y¹, Y² and Y³ are independently C(R³)₂, —C(R³)₂C(R³)₂—, NR³, Si(R³)₂ or Se;
each R³ is independently selected from H, alkyl, substituted alkyl, aryl, substituted aryl, heteroaryl, substituted heteroaryl, acyl, substituted acyl, alkoxy, substituted alkoxy, amido, substituted amido and a WSG;
a-i are independently 0 or 1;
each n, m and o are independently 0 or an integer from 1 to 10,000; and
p is an integer from 1 to 100,000. In some instances of formula (I), one of co-monomers M² and M³ includes a linked chemoselective functional group or a linked signaling chromophore.

In certain embodiments of formula (I), Y¹ is C(R³)₂. In some embodiments of formula (I), Y¹ is NR³. In certain instances of formula (I), Y' is Si(R³)₂. In certain cases of formula (I), Y¹ is —C(R³)₂C(R³)₂—. In some cases of formula (I), Y¹ is —CHR³CHR³—. In certain cases of formula (I), Y¹ is Se. In certain embodiments of formula (I), Y² is C(R³)₂. In some instances of formula (I), Y² is NR³. In certain embodiments of formula (I), Y² is Si(R³)₂. In certain cases of formula (I), Y² is —C(R³)₂C(R³)₂—. In some cases functional group. In certain cases of formula (I), Z¹ is a linked signaling chromophore. In certain embodiments of formula (I), at least one of G¹ and G² is a linker. In certain embodiments of formula (I), at least one of G¹ and G² is a linked specific binding member.

In some instances of formula (I), each fused tricyclic co-monomer is of the same core structure, e.g., a fluorene, a carbazole, a silole or a bridged bi-phenyl co-monomer. In some instances of formula (I), each fused tricyclic co-monomer is independently selected from a fluorene, a carbazole, a silole and a bridged bi-phenyl co-monomer. In certain instances of a fused tricyclic co-monomer of formula (I), one of Z⁵ and Z⁶ is CR. In some instances of a fused tricyclic co-monomer of formula (I), both of Z⁵ and Z⁶ are independently CR. In some embodiments of a fused tricyclic co-monomer of formula (I), Z⁵ is CR and Z⁶ is N. In certain cases of a fused tricyclic co-monomer of formula (I), Z⁵ is N and Z⁶ is CR. In certain instances of a fused tricyclic co-monomer of formula (I), one of Z⁵ and Z⁶ is CH. In certain instances of a fused tricyclic co-monomer of formula (I), both of Z⁵ and Z⁶ are CH. In some embodiments of a fused tricyclic co-monomer of formula (I), Z⁵ is CR and Z⁶ is N. In certain cases of a fused tricyclic co-monomer of formula (I), Z⁵ is N and Z⁶ is CR.

In certain instances of formula (I), M¹, M² and M³ are independently a heterocyclic co-monomer wherein at least one of M¹, M² and M³ is a thiophene containing co-monomer.

In some instances of formula (I), the multichromophore includes a conjugated segment having the structure of formula (Ia):

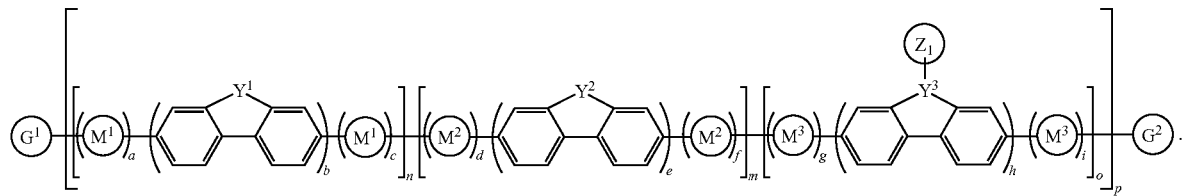

(Ia)

In certain embodiments of formula (I), $M^1$, $M^2$ and $M^3$ are each independently a thiophene containing co-monomer. In certain instances of formula (I), a+c≤1. In certain instances of formula (I), d+f≤1. In certain instances of formula (I), g+i≤1. In certain instances of formula (I), b+e+h≥1. In certain instances of formula (I), n+m+o≥1. In some cases, a+c≤1; d+f≤1; g+i≤1; b+e+h≥1; and n+m+o≥1. In certain instances, n≥1. In certain instances, m=0. In certain instances, o=O. In some cases, a+c=1. In certain cases, b=1 and e=1. In some cases, a+c=1. In certain cases, b+e+h=2. In some cases, d+f=1. In certain cases, b=1, e=1 and h=0. In some cases, g+i=1. In certain cases, b=1, e=0 and h=1.

In some embodiments of formula (I), the polymeric dye has the structure of formula (Ib):

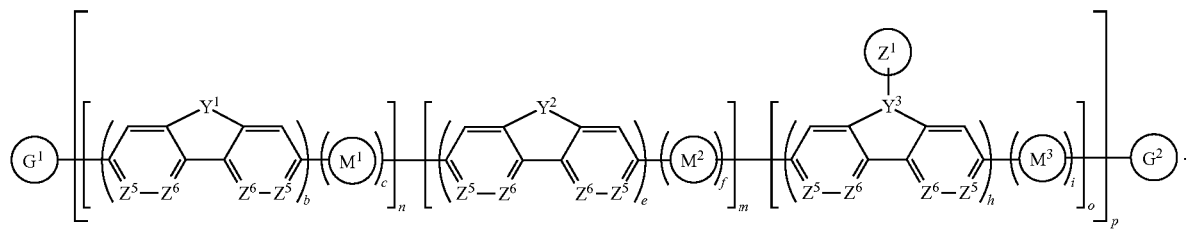

(Ib)

In some instances of formula (Ib), each fused tricyclic co-monomer is of the same core structure, e.g., a fluorene, a carbazole, a silole or a bridged bi-phenyl co-monomer. In some instances of formula (Ib), each fused tricyclic co-monomer is independently selected from a fluorene, a carbazole, a silole and a bridged bi-phenyl co-monomer. In certain instances of a fused tricyclic co-monomer of formula (Ib), one of $Z^5$ and $Z^6$ is CR. In some instances of a fused tricyclic co-monomer of formula (Ib), both of $Z^5$ and $Z^6$ are independently CR. In some embodiments of a fused tricyclic co-monomer of formula (Ib), $Z^5$ is CR and $Z^6$ is N. In certain cases of a fused tricyclic co-monomer of formula (Ib), $Z^5$ is N and $Z^6$ is CR. In certain instances of a fused tricyclic co-monomer of formula (Ib), one of $Z^5$ and $Z^6$ is CH. In certain instances of a fused tricyclic co-monomer of formula (Ib), both of $Z^5$ and $Z^6$ are CH. In some embodiments of a fused tricyclic co-monomer of formula (Ib), $Z^5$ is CR and $Z^6$ is N. In certain cases of a fused tricyclic co-monomer of formula (Ib), $Z^5$ is N and $Z^6$ is CR.

In some embodiments of formula (I) and (Ib), the polymeric dye has the structure of formula (Ic):

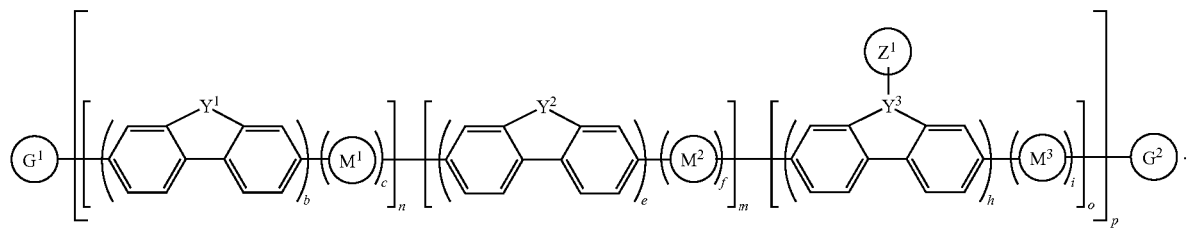

(Ic)

In certain instances of formula (Ib)-(Ic), h, i and o are each 0. In certain instances of formula (Ib)-(Ic), b and c are each 1. In certain instances of formula (Ib)-(Ic), e and f are each 1. In certain instances of formula (Ib)-(Ic), e, f and m are each 0. In certain instances of formula (Ib)-(Ic), h and i are each 1. In certain instances of formula (Ib)-(Ic), h, i and o are each 0; b and c are each 1; and e and f are each 1. In certain cases, $M^2$ is linked to a signaling chromophore or a chemoselective functional group. In certain instances of formula (Ib)-(Ic), e, f and m are each 0; b and c are each 1; and h and i are each 1. In certain cases, $Z^1$ is a linked signaling chromophore. In some cases, $Z^1$ is a linked chemoselective functional group.

In some embodiments of formula (I), the polymeric dye has the structure of formula (II):

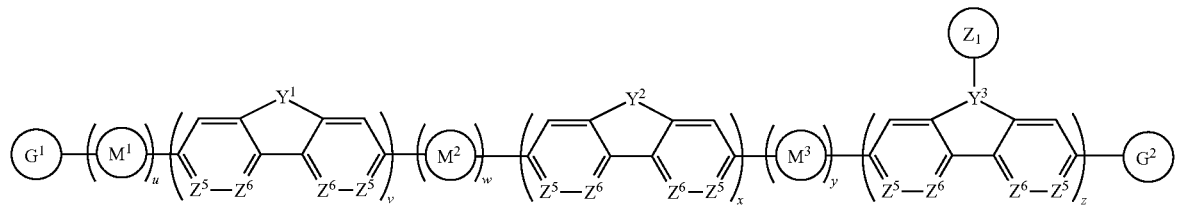

(IIa)

wherein u, v, w, x, y and z represent mol % values for each co-monomer in the multichromophore. In some instances of formula (IIa), each fused tricyclic co-monomer is of the same core structure, e.g., a fluorene, a carbazole, a silole or a bridged bi-phenyl co-monomer. In some instances of formula (IIa), each fused tricyclic co-monomer is independently selected from a fluorene, a carbazole, a silole and a bridged bi-phenyl co-monomer. In certain instances of a fused tricyclic co-monomer of formula (IIa), one of $Z^5$ and $Z^6$ is CR. In some instances of a fused tricyclic co-monomer of formula (IIa), both of $Z^5$ and $Z^6$ are independently CR. In some embodiments of a fused tricyclic co-monomer of formula (IIa), $Z^5$ is CR and $Z^6$ is N. In certain cases of a fused tricyclic co-monomer of formula (IIa), $Z^5$ is N and $Z^6$ is CR. In certain instances of a fused tricyclic co-monomer of formula (IIa), one of $Z^5$ and $Z^6$ is CH. In certain instances of a fused tricyclic co-monomer of formula (IIa), both of $Z^5$ and $Z^6$ are CH. In some embodiments of a fused tricyclic co-monomer of formula (IIa), $Z^5$ is CR and $Z^6$ is N. In certain cases of a fused tricyclic co-monomer of formula (IIa), $Z^5$ is N and $Z^6$ is CR. In certain instances, R is H, halogen, alkoxy, substituted alkoxy, alkyl and substituted alkyl. In some instances, R is fluoro, methoxy lower alkyl or substituted lower alkyl.

In some embodiments, the polymeric dye has the structure of formula (IIb):

(IIb)

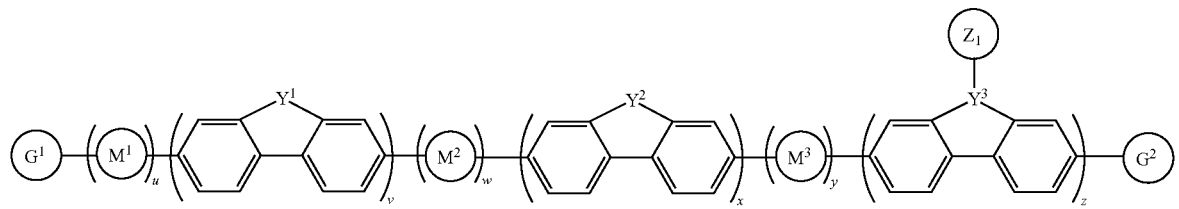

wherein u, v, w, x, y and z represent mol % values for each co-monomer in the multichromophore. It is understood that any of the polymeric dyes described herein can also be described by a formula including mol % values for each of the co-monomers that are present, e.g., a formula corresponding to formula (IIa)-(IIb). It is understood that any of the polymeric dyes of formula (Ia) and (Ic) can be represented by formula (II). In some instances of formula (IIa)-(IIb), u+w+y constitutes 5% or more by molarity (e.g., 5 mol %) of the multichromophore, such as 10% or more, 15% or more, 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, or even more. In certain instances, z is 0. In some instances of formula (IIa)-(IIb), $M^1$, $M^2$ and $M^3$ are each a thiophene-containing co-monomer. In some instances of formula (II), $M^1$ is a thiophene-containing co-monomer. In some instances of formula (IIa)-(IIb), $M^2$ is a thiophene-containing co-monomer. In some instances of formula (IIa)-(IIb), $M^3$ is a thiophene-containing co-monomer. In some instances of formula (IIa)-(IIb), v+x+z constitutes 80% or less by molarity (e.g., 80 mol %) of the multichromophore, such as 75% or less, 70% or less, 65% or less, 60% or less, 55% or less, 50% or less, 45% or less, 40% or less, 35% or less, 30% or less, 25% or less, 20% or less, 15% or less, 10% or less, or even less.

In some instances of formula (IIa)-(IIb), u is 5% or more, such as 10% or more, 15% or more, 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, or even more. In some instances of formula (IIa)-(IIb), w is 5% or more, such as 10% or more, 15% or more, 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, or even more. In some instances of formula (IIa)-(IIb), y is 1% or more, such as 2% or more, 5% or more, 10% or more, 15% or more, 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, or even more. In some instances of formula (IIa)-(IIb), v is 80% or less, such as 75% or less, 70% or less, 65% or less, 60% or less, 55% or less, 50% or less, 45% or less, 40% or less, 35% or less, 30% or less, 25% or less, 20% or less, 15% or less, 10% or less, or even less. In some instances of formula (IIa)-(IIb), x is 80% or less, such as 75% or less, 70% or less, 65% or less, 60% or less, 55% or less, 50% or less, 45% or less, 40% or less, 35% or less, 30% or less, 25% or less, 20% or less, 15% or less, 10% or less, or even less. In some instances of formula (IIa)-(IIb), z is 80% or less, such as 75% or less, 70% or less, 65% or less, 60% or less, 55% or less, 50% or less, 45% or less, 40% or less, 35% or less, 30% or less, 25% or less, 20% or less, 15% or less, 10% or less, or even less.

In some embodiments of formula (I)-(IIb), the polymeric dye has the structure of formula (IIIa):

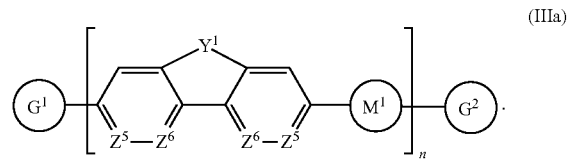

(IIIa)

In some instances of formula (IIIa), the fused tricyclic co-monomer is selected from a fluorene, a carbazole, a silole and a bridged bi-phenyl co-monomer. In certain instances of formula (IIIa), one of $Z^5$ and $Z^6$ is CR. In some instances of formula (IIIa), both of $Z^5$ and $Z^6$ are independently CR. In some embodiments of formula (IIIa), $Z^5$ is CR and $Z^6$ is N. In certain cases of formula (IIIa), $Z^5$ is N and $Z^6$ is CR. In certain instances of formula (IIIa), one of $Z^5$ and $Z^6$ is CH. In certain instances of formula (IIIa), both of $Z^5$ and $Z^6$ are CH. In some embodiments of formula (IIIa), $Z^5$ is CH and $Z^6$ is N. In certain cases of formula (IIIa), $Z^5$ is N and $Z^6$ is CR. In certain instances, R is H, halogen, alkoxy, substituted alkoxy, alkyl and substituted alkyl. In some instances, R is fluoro, methoxy lower alkyl or substituted lower alkyl.

In some embodiments of formula (I)-(IIIa), the polymeric dye has the structure of formula (IIIb):

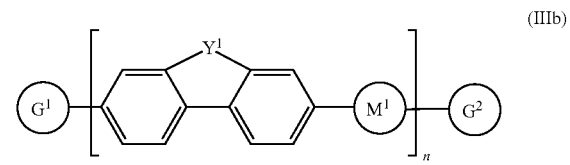

(IIIb)

wherein n is an integer from 1 to 100,000 and $M^1$ is a thiophene-containing co-monomer. In certain embodiments of formula OM-(IIIb), $Y^1$ is $C(R^3)_2$. In certain embodiments of formula OM-(IIb), $Y^1$ is —$C(R^3)_2C(R^3)_2$—. In some cases of formula (IIIa)-(IIIb), $Y^2$ is —$CHR^3CHR^3$—. In certain instances of formula (IIIa)-(IIIb), $Y^1$ is $NR^3$. In certain embodiments of formula (III)-(IIIb), $Y^1$ is $Si(R^3)_2$. In some instances, each $R^3$ is independently selected from H, alkyl, substituted alkyl, aryl, substituted aryl, heteroaryl, substituted heteroaryl, acyl, substituted acyl, alkoxy, substituted alkoxy, amido, substituted amido, substituted sulfonamido and a WSG. In certain instances, at least one $R^3$ is a WSG. In certain cases, both $R^3$ groups are independently a WSG.

In some embodiments of formula (I)-(IIa), the polymeric dye has the structure of formula (IVa):

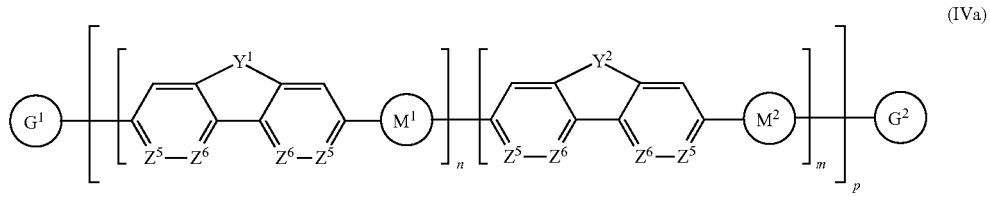

(IVa)

wherein: M¹ and M² are each independently a thiophene containing co-monomer; each n and m are independently an integer from 1 to 10,000; and p is an integer from 1 to 100,000. In some instances of formula (IVa), each fused tricyclic co-monomer is of the same core structure, e.g., a fluorene, a carbazole, a silole or a bridged bi-phenyl co-monomer. In some instances of formula (IVa), each fused tricyclic co-monomer is independently selected from a fluorene, a carbazole, a silole and a bridged bi-phenyl co-monomer. In some instances of formula (IVa), the fused tricyclic co-monomer is selected from a fluorene, a carbazole, a silole and a bridged bi-phenyl co-monomer. In certain instances of formula (IVa), one of $Z^5$ and $Z^6$ is CR. In some instances of formula (IVa), both of $Z^5$ and $Z^6$ are independently CR. In some embodiments of formula (IVa), $Z^5$ is CR and $Z^6$ is N. In certain cases of formula (IVa), $Z^5$ is N and $Z^6$ is CR. In certain instances of formula (IVa), one of $Z^5$ and $Z^6$ is CH. In certain instances of formula (IVa), both of $Z^5$ and $Z^6$ are CH. In some embodiments of formula (IVa), $Z^5$ is CR and $Z^6$ is N. In certain cases of formula (IVa), $Z^5$ is N and $Z^6$ is CR. In certain instances, R is H, halogen, alkoxy, substituted alkoxy, alkyl and substituted alkyl. In some instances, R is fluoro, methoxy lower alkyl or substituted lower alkyl.

In some embodiments of formula (I)-(IVa), the polymeric dye has the structure of formula (IVb):

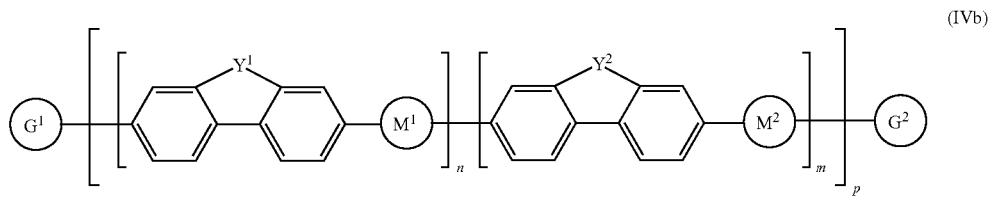

(IVb)

wherein: M¹ and M² are each independently a thiophene containing co-monomer; each n and m are independently an integer from 1 to 10,000; and p is an integer from 1 to 100,000. In certain instances of formula (IVa)-(IVb), Y¹ is NR³; Y² is C(R³)₂; and M¹ and M² are the same thiophene containing co-monomer. In certain instances of formula (IVa)-(IVb), Y¹ is C(R³)₂; Y² is NR³; and M¹ and M² are the same thiophene containing co-monomer. In certain instances of formula (IVa)-(IVb), Y¹ and Y² are each independently C(R³)₂; and M¹ and M² are the same thiophene containing co-monomer. In certain instances of formula (IVa)-(IVb), Y¹ is NR³; Y² is C(R³)₂; and M¹ and M² are different thiophene containing co-monomers. In certain instances of formula (IVa)-(IVb), Y¹ is C(R³)₂; Y² is NR³; and M¹ and M² are different thiophene containing co-monomers. In certain instances of formula (IVa)-(IVb), Y¹ and Y² are each independently C(R³)₂; and M¹ and M² are different thiophene containing co-monomers. In certain instances of formula (IVa)-(IVb), Y¹ and Y² are each independently Si(R³)₂. In certain instances of formula (IVa)-(IVb), Y¹ is Si(R³)₂. In certain instances of formula (IVa)-(IVb), Y² is Si(R³)₂. In some cases of formula (IVa)-(IVb), Y¹ is —C(R³)₂C(R³)₂—. In some cases of formula (IVa)-(IVb), Y¹ is —CHR³CHR³. In some cases of formula (IVa)-(IVb), Y² is —C(R³)₂C(R³)₂—. In some cases of formula (IVa)-(IVb), Y² is —CHR³CHR³. In some instances, each R³ is independently selected from H, alkyl, substituted alkyl, aryl, substituted aryl, heteroaryl, substituted heteroaryl, acyl, substituted acyl, alkoxy, substituted alkoxy, amido, substituted amido and a WSG. In certain instances, at least one R³ is a WSG. In certain cases, both R³ groups are independently a WSG.

In certain embodiments of formula (I)-(IIb), the polymeric dye has the structure of formula (Va):

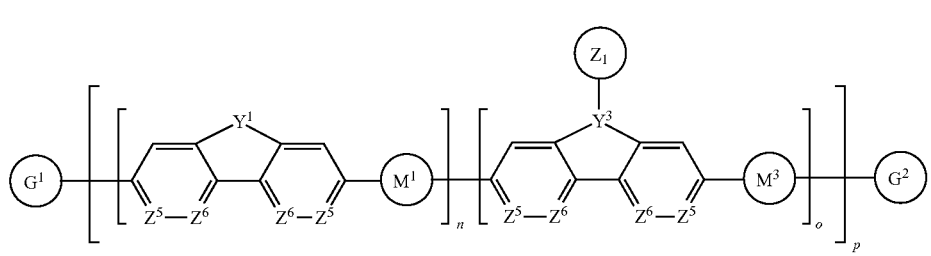
(Va)

wherein: $M^1$ and $M^3$ are each independently a thiophene containing co-monomer; each n and each o are independently an integer from 1 to 10,000; and p is an integer from 1 to 100,000. In some instances of formula (Va), each fused tricyclic co-monomer is of the same core structure, e.g., a fluorene, a carbazole, a silole or a bridged bi-phenyl co-monomer. In some instances of formula (Va), each fused tricyclic co-monomer is independently selected from a fluorene, a carbazole, a silole and a bridged bi-phenyl co-monomer. In some instances of formula (Va), the fused tricyclic co-monomer is selected from a fluorene, a carbazole, a silole and a bridged bi-phenyl co-monomer. In certain instances of formula (Va), one of $Z^5$ and $Z^6$ is CR. In some instances of formula (Va), both of $Z^5$ and $Z^6$ are independently CR. In some embodiments of formula (Va), $Z^5$ is CR and $Z^6$ is N. In certain cases of formula (Va), $Z^5$ is N and $Z^6$ is CR. In certain instances of formula (Va), one of $Z^5$ and $Z^6$ is CH. In certain instances of formula (Va), both of $Z^5$ and $Z^6$ are CH. In some embodiments of formula (Va), $Z^5$ is CR and $Z^6$ is N. In certain cases of formula (Va), $Z^5$ is N and $Z^6$ is CR. In certain instances, R is H, halogen, alkoxy, substituted alkoxy, alkyl and substituted alkyl. In some instances, R is fluoro, methoxy lower alkyl or substituted lower alkyl.

In certain embodiments of formula (I)-(IIb), the polymeric dye has the structure of formula (Vb):

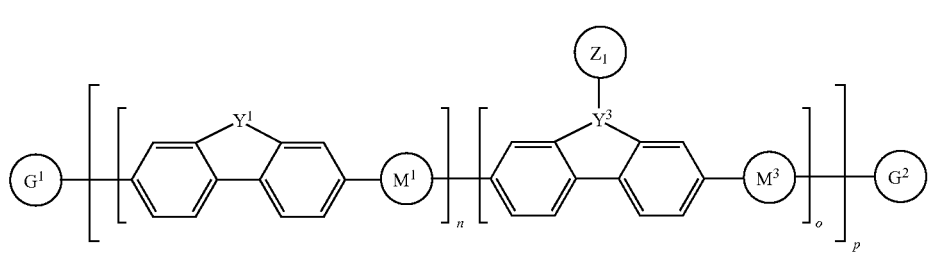
(Vb)

wherein: $M^1$ and $M^3$ are each independently a thiophene containing co-monomer; each n and each o are independently an integer from 1 to 10,000; and p is an integer from 1 to 100,000. In some instances of formula (Va)-(Vb), $Y^3$—$Z^1$ is $C(R^3)(T^1\text{-}Z^1)$, wherein $Z^1$ is a chemoselective functional group or a linked signaling chromophore and $T^1$ is a linker. In some cases of formula (Va)-(Vb), $Y^3$—$Z^1$ is N-$T^1$-$Z^1$, wherein $Z^1$ is a chemoselective functional group or a linked signaling chromophore and $T^1$ is a linker. In some instances of formula (Va)-(Vb), $Y^3$—$Z^1$ is $Si(R^3)(T^1\text{-}Z^1)$, wherein $Z^1$ is a chemoselective functional group or a linked signaling chromophore and $T^1$ is a linker. In certain instances, $Z^1$ is a chemoselective functional group. In some instances, $Z^1$ is a linked signaling chromophore. In some embodiments of formula (Va)-(Vb), $Y^1$ is $NR^3$; and $M^1$ and $M^3$ are the same thiophene containing co-monomer. In some embodiments of formula (Va)-(Vb), $Y^1$ is $C(R^3)_2$; and $M^1$ and $M^3$ are the same thiophene containing co-monomer. In some instances of formula (Va)-(Vb), $Y^1$ is $NR^3$; and $M^1$ and $M^3$ are different thiophene containing co-monomers. In some embodiments of formula (Va)-(Vb), $Y^1$ is $C(R^3)_2$; and $M^1$ and $M^3$ are different thiophene containing co-monomers. In some cases of formula (Va)-(Vb), $Y^1$ is —$C(R^3)_2$ $C(R^3)_2$—. In some cases of formula (Va)-(Vb), $Y^1$ is —$CHR^3CHR^3$—. In some embodiments of formula (Va)-(Vb), $Y^1$ is $Si(R^3)_2$. In some embodiments of formula (Va)-(Vb), $M^1$ and $M^3$ are the same thiophene containing co-monomer. In some embodiments of formula (Va)-(Vb), $M^1$ and $M^3$ are different thiophene containing co-monomers.

In certain embodiments of formula (I)-(II), the polymeric dye has the structure of formula (VIa):

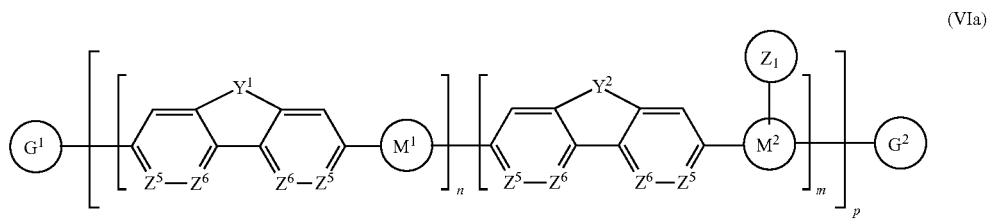

(VIa)

wherein: at least one of $M^1$ and $M^2$ is a thiophene containing co-monomer; each n and each o are independently an integer from 1 to 10,000; $Z^1$ is a linked chemoselective functional group or a linked signaling chromophore; and p is an integer from 1 to 100,000. In some instances of formula (VIa), each fused tricyclic co-monomer is of the same core structure, e.g., a fluorene, a carbazole, a silole or a bridged bi-phenyl co-monomer. In some instances of formula (VIa), each fused tricyclic co-monomer is independently selected from a fluorene, a carbazole, a silole and a bridged bi-phenyl co-monomer. In certain instances of a fused tricyclic co-monomer of formula (VIa), one of $Z^5$ and $Z^6$ is CR. In some instances of a fused tricyclic co-monomer of formula (VIa), both of $Z^5$ and $Z^6$ are independently CR. In some embodiments of a fused tricyclic co-monomer of formula (VIa), $Z^5$ is CR and $Z^6$ is N. In certain cases of a fused tricyclic co-monomer of formula (VIa), $Z^5$ is N and $Z^6$ is CR. In certain instances of a fused tricyclic co-monomer of formula (VIa), one of $Z^5$ and $Z^6$ is CH. In certain instances of a fused tricyclic co-monomer of formula (VIa), both of $Z^5$ and $Z^6$ are CH. In some embodiments of a fused tricyclic co-monomer of formula (VIa), $Z^5$ is CR and $Z^6$ is N. In certain cases of a fused tricyclic co-monomer of formula (VIa), $Z^5$ is N and $Z^6$ is CR. In certain instances, R is H, halogen, alkoxy, substituted alkoxy, alkyl and substituted alkyl. In some instances, R is fluoro, methoxy lower alkyl or substituted lower alkyl.

In certain embodiments of formula (I)-(VIa), the polymeric dye has the structure of formula (VIb):

(VIa)-(VIb), $Y^2$ is $NR^3$. In some embodiments of formula (VIa)-(VIb), $Y^2$ is $C(R^3)_2$. In certain instances of formula (VIa)-(VIb), $Y^1$ and $Y^2$ are each independently $Si(R^3)_2$. In certain instances of formula (VIa)-(VIb), $Y^1$ is $Si(R^3)_2$. In certain instances of formula (VIa)-(VIb), $Y^2$ is $Si(R^3)_2$. In some cases of formula (VIa)-(VIb), $Y^1$ is —$C(R^3)_2C(R^3)_2$—. In some cases of formula (VIa)-(VIb), $Y^1$ is —$CHR^3CHR^3$. In some cases of formula (VIa)-(VIb), $Y^2$ is —$C(R^3)_2C(R^3)_2$—. In some cases of formula (VIa)-(VIb), $Y^2$ is —$CHR^3CHR^3$. In some instances of formula (VIa)-(VIb), $M^1$ and $M^2$ have the same underlying unsubstituted thiophene containing co-monomer, except $M^2$ includes a linked $Z^1$, and $M^1$ is optionally substituted with a $R^3$ group. In some instances of formula (VIa)-(VIb), $M^1$ and $M^2$ are different thiophene containing co-monomers. In some instances, each $R^3$ is independently selected from H, alkyl, substituted alkyl, aryl, substituted aryl, heteroaryl, substituted heteroaryl, acyl, substituted acyl, alkoxy, substituted alkoxy, amido, substituted amido and a WSG. In certain instances, at least one $R^3$ is a WSG. In certain cases, both $R^3$ groups are independently a WSG.

Thiophene-Containing Co-Monomers

Aspects of the present disclosure include water solvated polymeric dyes (e.g., as described herein, such as a polymeric dye of one of formula (I)-(VIb)) including a thiophene-containing co-monomer. The term "thiophene-containing co-monomer" refers to a heterocyclic group or substituted heterocyclic group that includes a thiophene ring and is capable of conjugation with a pi-conjugated polymer

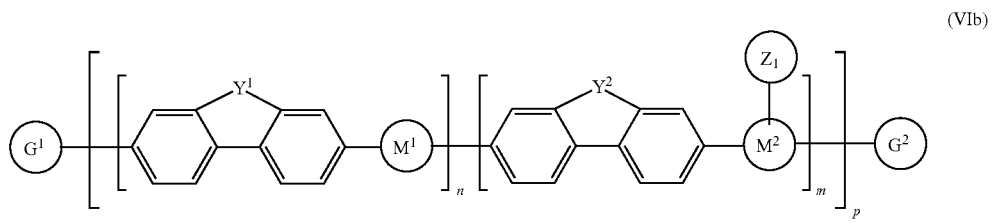

(VIb)

wherein: at least one of $M^1$ and $M^2$ is a thiophene containing co-monomer; each n and each o are independently an integer from 1 to 10,000; $Z^1$ is a linked chemoselective functional group or a linked signaling chromophore; and p is an integer from 1 to 100,000. In some cases of formula (VIa)-(VIb), $M^1$ and $M^2$ are each independently a thiophene containing co-monomer. In some instances of formula (VIa)-(VIb), $Z^1$ is a linked chemoselective functional group. In some instances of formula (VIa)-(VIb), $Z^1$ is a linked signaling chromophore. In some embodiments of formula (VIa)-(VIb), $Y^1$ is $NR^3$. In some embodiments of formula (VIa)-(VIb), $Y^1$ is $C(R^3)_2$. In some embodiments of formula backbone via adjacent co-monomers. A thiophene that is a 5-membered aromatic heterocyclic ring having the formula $C_4H_4S$, which can be substituted with any convenient substituents (e.g., at the 2, 3, 4 and/or 5 positions and/or linked or fused to any convenient aryl or heteroaryl ring systems (e.g., fused to an additional ring at the 2,3-, 3,4- and/or 4,5-positions). The co-monomer is divalent and as such is substituted at two sites of the ring system for covalent attachment to the unsaturated backbone of a conjugated polymer. In some cases, the thiophene ring of the co-monomer is connected to the conjugated polymer backbone via positions 2 and/or 5 of the thiophene ring.

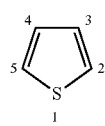

Any convenient thiophene-containing heterocyclic groups can be adapted for use as a thiophene-containing co-monomer in the subject conjugated polymers. Thiophene-containing heterocyclic groups of interest include, but are not limited to, thiophene, 1-benzothiophene, 2-benzothiophene, dibenzothiophene, and polythiophene such as fused dithiophene or fused trithiophene, which groups can be connected to the conjugated polymer via any two convenient positions of the group and can be optionally further substituted, e.g., with a WSG. In some cases, the thiophene-containing co-monomer is monocyclic (e.g., a substituted thiophene). In some cases, the thiophene-containing co-monomer comprises a fused thiophene ring, such as a 1-benzothiophene, 2-benzothiophene and substituted versions thereof. In some cases, the thiophene-containing co-monomer comprises an aryl or heteroaryl ring system as a substituent that is not directly connected to the conjugated polymer backbone.

In some embodiments of formulae (I)-(VIb), the thiophene-containing co-monomer(s) ($M^1$-$M^3$) are selected from formula (VII), (VIII) and (IX):

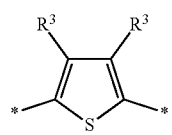

(VII)

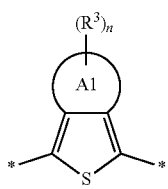

(VIII)

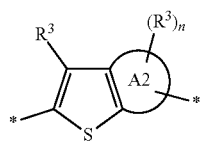

(IX)

wherein:
A1 and A2 are each a fused monocyclic or bicyclic group
each $R^3$ is independently selected from H, amino, substituted amino, halogen, cyano, alkyl, substituted alkyl, aryl, substituted aryl, heteroaryl, substituted heteroaryl, acyl, substituted acyl, amido, substituted amido, sulfonic acid, cyano, alkoxy, substituted alkoxy, WSG and -$T^2$-$Z^2$, wherein $Z^2$ is a chemoselective functional group or a linked acceptor chromophore, and $T^2$ is a linker;
n is 0, 1, 2, 3 or 4; and
each * is a site for covalent attachment to the unsaturated backbone of a conjugated polymer. In some instances of formulae (I)-(VIb), a thiophene-containing co-monomer (e.g., $M^1$, $M^2$ and/or $M^3$) is described by formula (VII). In some instances of formulae (I)-(VIb), a thiophene-containing co-monomer (e.g., $M^1$, $M^2$ and/or $M^3$) is described by formula (VIII). In some instances of formulae (I)-(VIb), the thiophene-containing co-monomer (e.g., $M^1$, $M^2$ and/or $M^3$) is described by formula (IX).

Fused monocyclic or bicyclic groups of interest include fused carbocyclic and heterocyclic groups having one or two 5, 6 and/or 7-membered rings which when fused with the thiophene ring form a fused two or three-ring system. The fused carbocyclic and heterocylic rings can be saturated or unsaturated. In certain instances of formula (VIII)-(IX), A1 and A2 are a fused monocyclic group, such as a fused benzo ring, a fused pyridyl ring, a fused benzothiophene ring system or a fused 7-membered heterocycle. In some instances of formula (VIII)-(IX), A1 and A2 are selected from a fused monocyclic heterocycle, a fused monocyclic heteroaryl and a fused bicyclic heteroaryl.

In some embodiments of formulae (VII)-(IX), the thiophene-containing co-monomer(s) are selected from formulae (X)-(XVII):

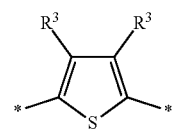

(X)

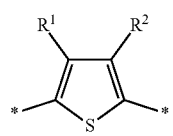

(XI)

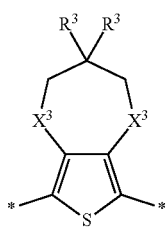

(XII)

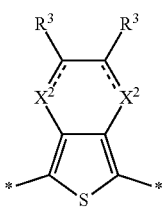

(XIII)

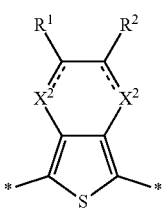

(XIV)

-continued (XV)

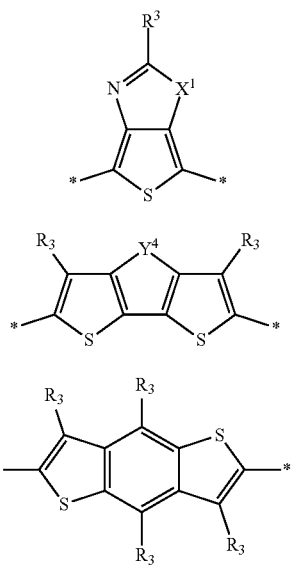

(XVI)

(XVII)

wherein:
X¹ is CR³, NR³, O or S;
each X² is independently N, O or S, wherein when X² is N, the adjacent ==== is a double bond and when X² is O or S, the adjacent ==== is a single bond;
each X³ is independently O, S or CH;
R¹ and R² together form a 5- or 6-membered fused aryl or heteroaryl ring which is optionally substituted with one or more R³ groups; and
Y⁴ is NR³, C(R³)₂ or Si(R³)₂.

In certain embodiments of formula (XV), X¹ is CR³. In certain embodiments of formula (XV), X¹ is CH. In certain cases of formula (XV), X¹ is NR³. In certain instances of formula (XV), X¹ is O. In some embodiments of formula (XV), X¹ is S. In certain instances of formula (XV), R³ is a WSG and X¹ is O or S.

In certain embodiments of formula (XII)-(XIII), each X² is N. In certain embodiments of formula (XIII)-(XIV), each X² is O. In certain embodiments of formula (XIII)-(XIV), each X² is S. In certain embodiments of formula (XII), each X³ is O. In certain embodiments of formula (XII), each X³ is S. In certain embodiments of formula (XII), each X³ is CH.

In some embodiments of the polymeric dye, the thiophene-containing co-monomers (e.g., co-monomers M¹-M³) are independently selected from formulae (XVIII) and (XIX):

(XX)

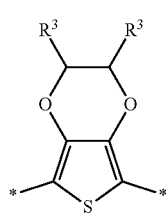

-continued (XXI)

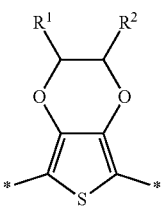

wherein:
R¹ and R² together form a 5- or 6-membered fused aryl or heteroaryl ring which is optionally substituted with one or more R³ groups; and
each R³ is independently selected from H, amino, substituted amino, halogen, cyano, alkyl, substituted alkyl, aryl, substituted aryl, heteroaryl, substituted heteroaryl, acyl, substituted acyl, amido, substituted amido, sulfonic acid, cyano, alkoxy, substituted alkoxy and -T²-Z², wherein Z² is a chemoselective functional group or a linked acceptor chromophore, and T² is a linker.

In some embodiments of formula (I)-(XVII), a thiophene-containing co-monomer (e.g., M¹, M² and/M³) is described by one of the following structures (a) to (q):

(a)

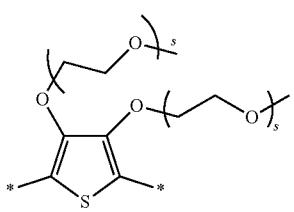

(b)

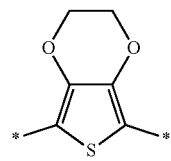

(c)

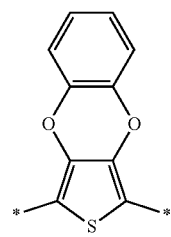

(d)

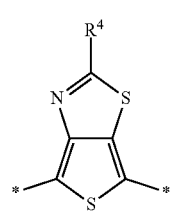

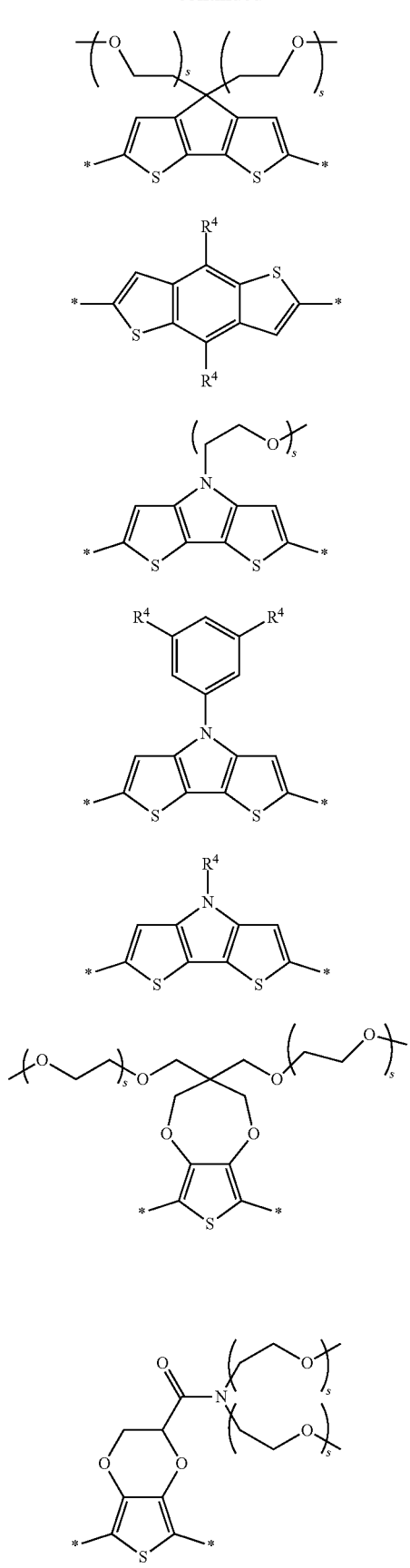

-continued (q)

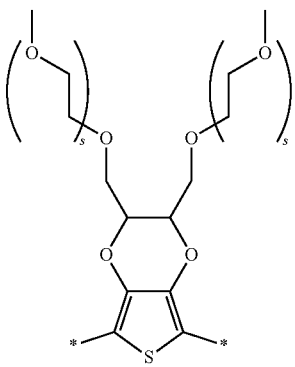

wherein:
each $R^4$ is independently selected from H, amino, substituted amino, halogen, cyano, alkyl, substituted alkyl, aryl, substituted aryl, heteroaryl, substituted heteroaryl, acyl, substituted acyl, amido, substituted amido, sulfonic acid, cyano, alkoxy, substituted alkoxy, WSG and $-T^2-Z^2$, wherein $Z^2$ is a chemoselective functional group or a linked signaling chromophore, and $T^2$ is a linker; and each s is 0 or an integer from 1 to 50. In certain instances, each s is independently 1 to 20, such as 3 to 20, 3 to 15, 3 to 12, or 6 to 12. In certain cases, each s is independently 1, 2, 3, 4, 5, 6, 7, 8, 9, 10, 11 or 12. In some cases, each s is 3. In some cases, each s is 4. In some cases, each s is 5. In some cases, each s is 6. In some cases, each s is 7. In some cases, each s is 8. In some cases, each s is 9. In some cases, each s is 10. In some cases, each s is 11. In some instances, at least one $R^4$ is $-T^2-Z^2$. In some embodiments, $T^2$ is an alkyl linker, such as a C1-C6 alkyl linker. In some embodiments, $T^2$ is a substituted alkyl linker. In some embodiments, $T^2$ is an alkoxy linker (e.g., —O-alkyl-). In some embodiments, $T^2$ is a substituted alkoxy. In some instances, $Z^2$ is a chemoselective functional group. In some instances, $Z^2$ is a linked signaling chromophore. In some instances, each $R^4$ is a WSG. In some instances, each $R^4$ is a substituted alkyl group. In some instances, each $R^4$ is an alkoxy or a substituted alkoxy group.

The thiophene-containing co-monomers (e.g., co-monomers $M^1$-$M^3$) can be any convenient fused tricyclic co-monomer. Tricyclic co-monomers of interest include, but are not limited to, those co-monomers including two thiophene rings connected via a fused central 5- or 6-membered aryl or heteroaryl ring. The fused central ring can be a pyrrole, a benzo or a cyclopentadiene. In some embodiments of the polymeric dye, the thiophene-containing co-monomers (e.g., co-monomers $M^1$-$M^3$) are independently selected from formulae (e)-(i):

(e)

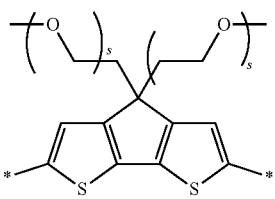

(f)

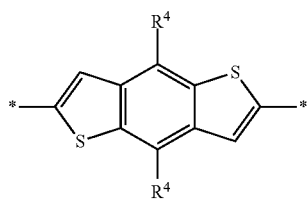

(g)

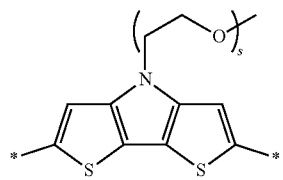

(h)

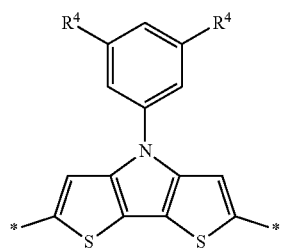

(i)

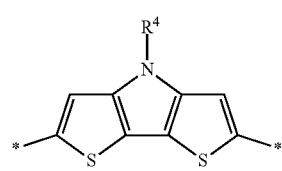

wherein: each $R^4$ is independently selected from H, amino, substituted amino, halogen, cyano, alkyl, substituted alkyl, aryl, substituted aryl, heteroaryl, substituted heteroaryl, acyl, substituted acyl, amido, substituted amido, sulfonic acid, cyano, alkoxy, substituted alkoxy and $-T^2-Z^2$, wherein $Z^2$ is a chemoselective functional group or a linked acceptor chromophore, and $T^2$ is a linker; and each s is 0 or an integer from 1 to 50 (e.g., s is 1 to 20, etc., such as s is 11).

In some embodiments of formula (I)-(XVI), at least one thiophene-containing co-monomer is described by structure (a). In some embodiments of formula (I)-(XVI), at least one thiophene-containing co-monomer is described by structure (b). In some embodiments of formula (I)-(XVI), at least one thiophene-containing co-monomer is described by structure (c). In some embodiments of formula (I)-(XVI), at least one thiophene-containing co-monomer is described by structure (d). In some embodiments of formula (I)-(XVI), at least one thiophene-containing co-monomer is described by structure (e). In some embodiments of formula (I)-(XVI), at least one thiophene-containing co-monomer is described by structure (f). In some embodiments of formula (I)-(XVI), at least one thiophene-containing co-monomer is described by structure (g). In some embodiments of formula (I)-(XVI), at least one thiophene-containing co-monomer is described by structure (h). In some embodiments of formula (I)-(XVI), at least one thiophene-containing co-monomer is described by structure (i). In some embodiments of formula (I)-(XVI), at least one thiophene-containing co-monomer is described by structure (j). In some embodiments of formula (I)-(XVI), at least one thiophene-containing co-monomer is described by structure (k). In some embodiments of formula (I)-(XVI), at least one thiophene-containing co-monomer is described by structure (I). In some embodiments of formula (I)-(XVI), at least one thiophene-containing co-monomer is described by structure (m). In some embodiments of formula (I)-(XVI), at least one thiophene-containing co-monomer is described by structure (n). In some embodiments of formula (I)-(XVI), at least one thiophene-containing co-monomer is described by structure (o). In some embodiments of formula (I)-(XVI), at least one thiophene-containing co-monomer is described by structure (p). In some embodiments of formula (I)-(XVI), at least one thiophene-containing co-monomer is described by structure (q).

In some embodiments of formula (I)-(XVII) and (a)-(q), a thiophene-containing co-monomer (e.g., $M^1$, $M^2$ and/$M^3$) is described by one of the following structures (ba) to (bu):

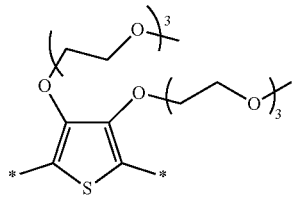
(ba)

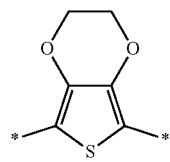
(bb)

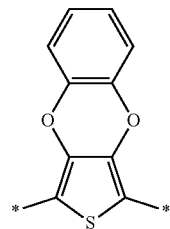
(bc)

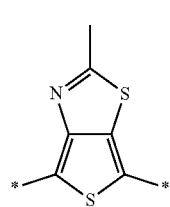
(bd)

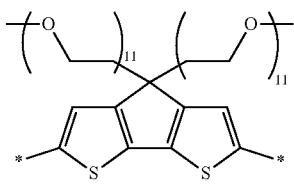
(be)

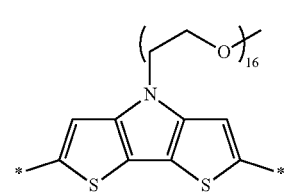
(bf)

-continued

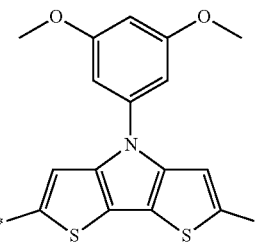
(bg)

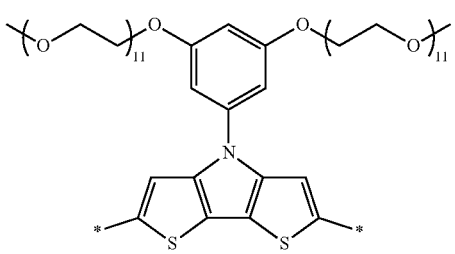
(bh)

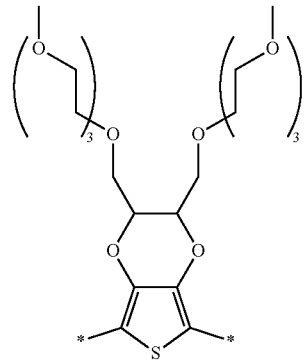
(bi)

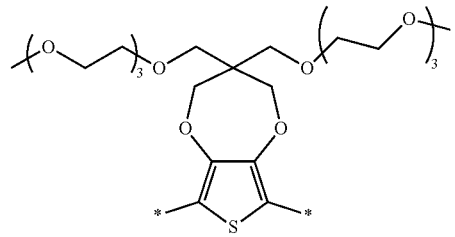
(bj)

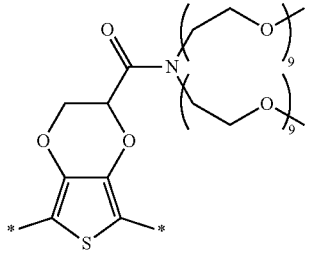
(bk)

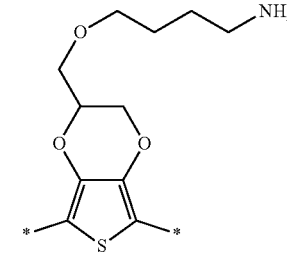
(bl)

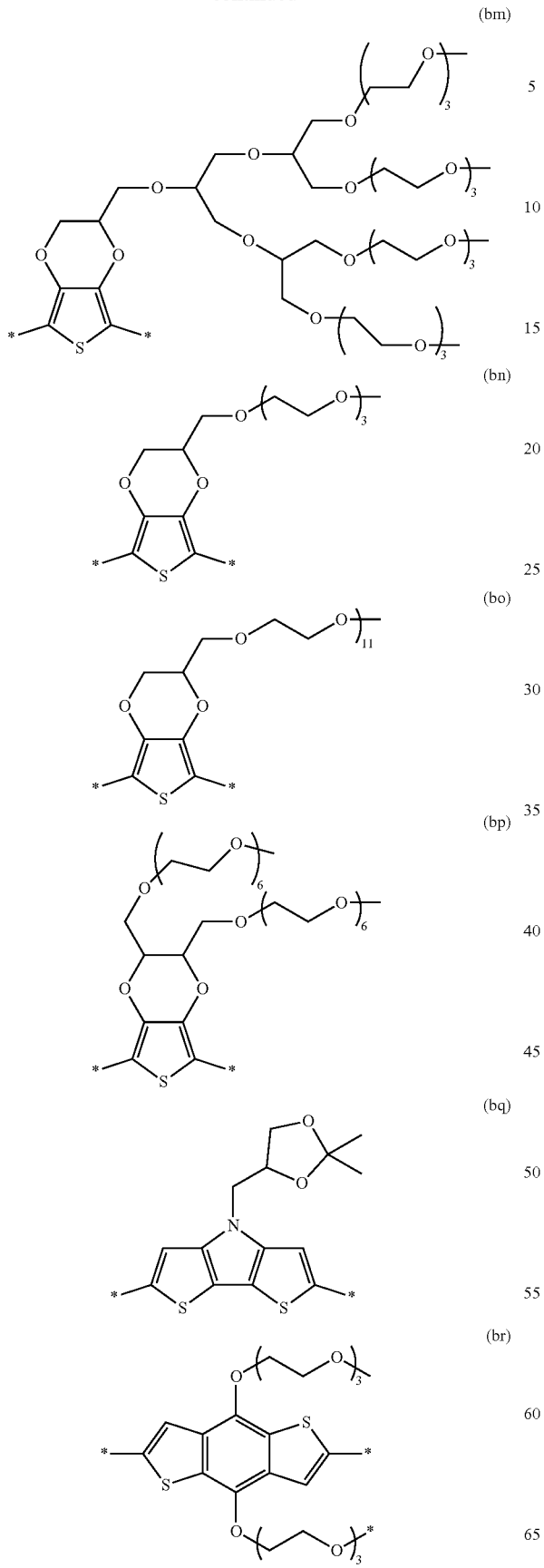
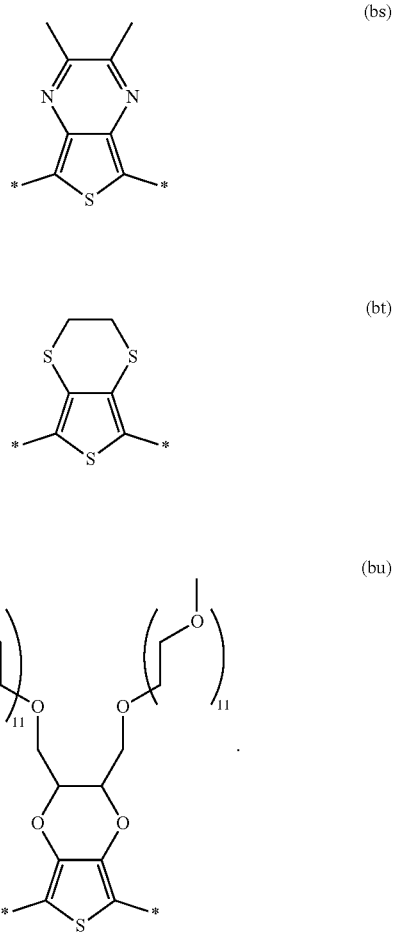

In some instances, at least one thiophene-containing co-monomer (e.g., $M^1$, $M^2$ and/$M^3$) has structure (ba). In some instances, at least one thiophene-containing co-monomer (e.g., $M^1$, $M^2$ and/$M^3$) has structure (bb). In some instances, at least one thiophene-containing co-monomer (e.g., $M^1$, $M^2$ and/$M^3$) has structure (bc). In some instances, at least one thiophene-containing co-monomer (e.g., $M^1$, $M^2$ and/$M^3$) has structure (bd). In some instances, at least one thiophene-containing co-monomer (e.g., $M^1$, $M^2$ and/$M^3$) has structure (be). In some instances, at least one thiophene-containing co-monomer (e.g., $M^1$, $M^2$ and/$M^3$) has structure (bf). In some instances, at least one thiophene-containing co-monomer (e.g., $M^1$, $M^2$ and/$M^3$) has structure (bg). In some instances, at least one thiophene-containing co-monomer (e.g., $M^1$, $M^2$ and/$M^3$) has structure (bh). In some instances, at least one thiophene-containing co-monomer (e.g., $M^1$, $M^2$ and/$M^3$) has structure (bi). In some instances, at least one thiophene-containing co-monomer (e.g., $M^1$, $M^2$ and/$M^3$) has structure (bj). In some instances, at least one thiophene-containing co-monomer (e.g., $M^1$, $M^2$ and/$M^3$) has structure (bk). In some instances, at least one thiophene-containing co-monomer (e.g., $M^1$, $M^2$ and/$M^3$) has structure (bl). In some instances, at least one thiophene-containing co-monomer (e.g., $M^1$, $M^2$ and/$M^3$) has structure (bm). In some instances, at least one thiophene-containing co-monomer (e.g., $M^1$, $M^2$ and/$M^3$) has structure (bn). In some instances, at least one thiophene-containing co-monomer (e.g., $M^1$, $M^2$ and/$M^3$) has structure (bo). In some instances, at least one thiophene-containing co-monomer (e.g., $M^1$, $M^2$ and/$M^3$)

has structure (bp). In some instances, at least one thiophene-containing co-monomer (e.g., $M^1$, $M^2$ and/$M^3$) has structure (bq). In some instances, at least one thiophene-containing co-monomer (e.g., $M^1$, $M^2$ and/$M^3$) has structure (br). In some instances, at least one thiophene-containing co-monomer (e.g., $M^1$, $M^2$ and/$M^3$) has structure (bs). In some instances, at least one thiophene-containing co-monomer (e.g., $M^1$, $M^2$ and/$M^3$) has structure (bt). In some instances, at least one thiophene-containing co-monomer (e.g., $M^1$, $M^2$ and/$M^3$) has structure (bu).

In some embodiments of formulae (I)-(VI), the polymeric dye includes a conjugated segment having one of the following structures:

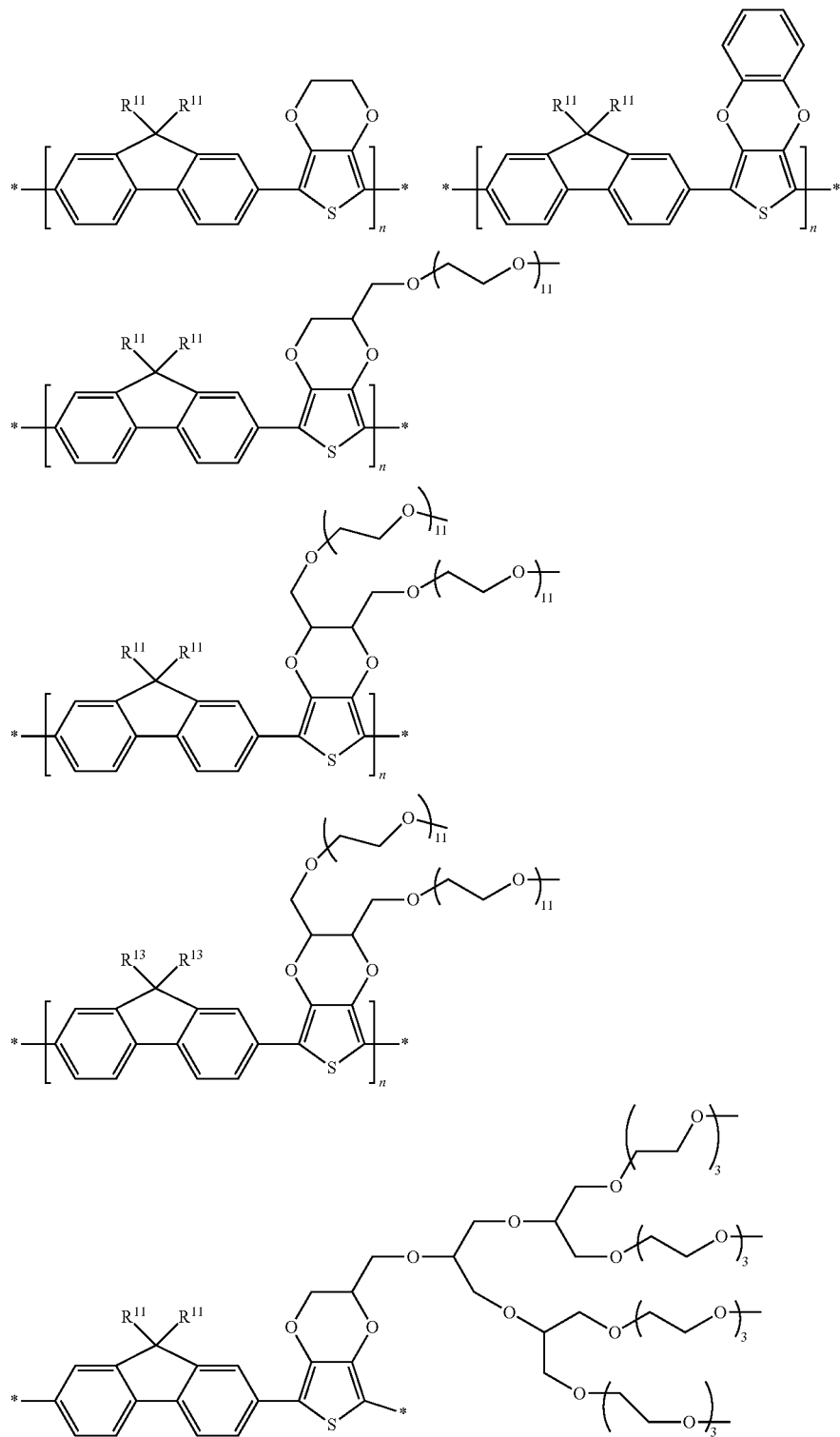

-continued
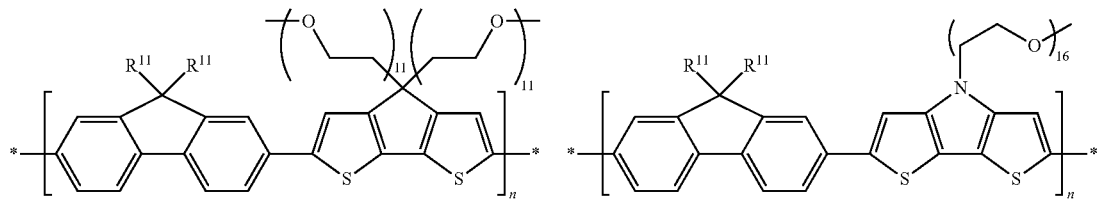
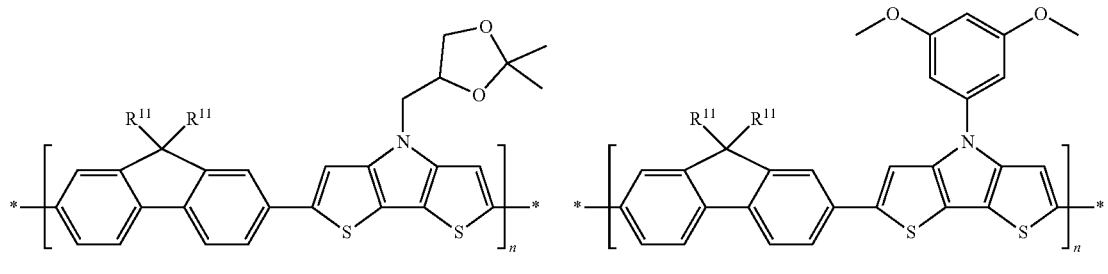
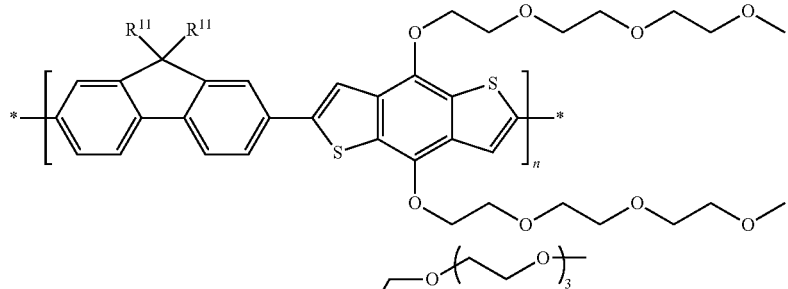
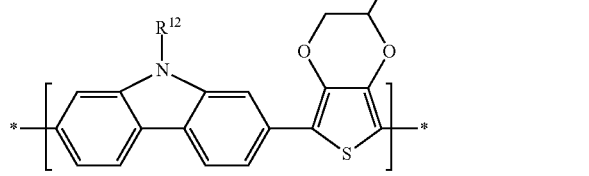
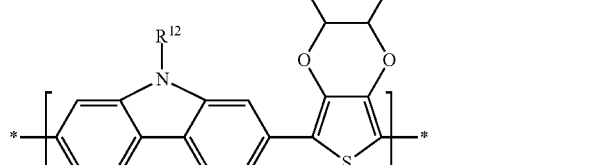
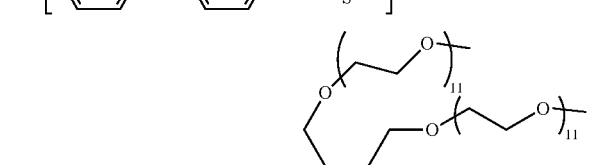
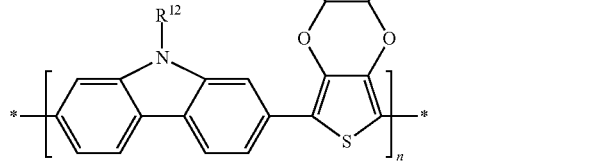
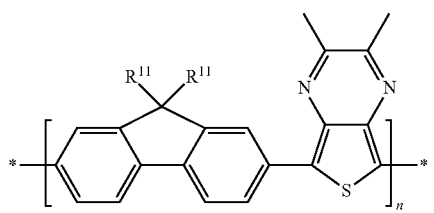

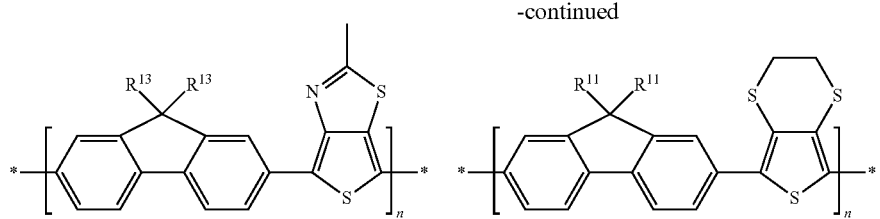
where n is 1 to 100,000 and each $R^{11}$, $R^{12}$ and $R^{13}$ is independently a substituted alkyl, a substituted aralkyl, or a WSG.
In some embodiments of formulae (I), (Ib), (II) and (V), the polymeric dye includes a conjugated segment having one of the following structures:
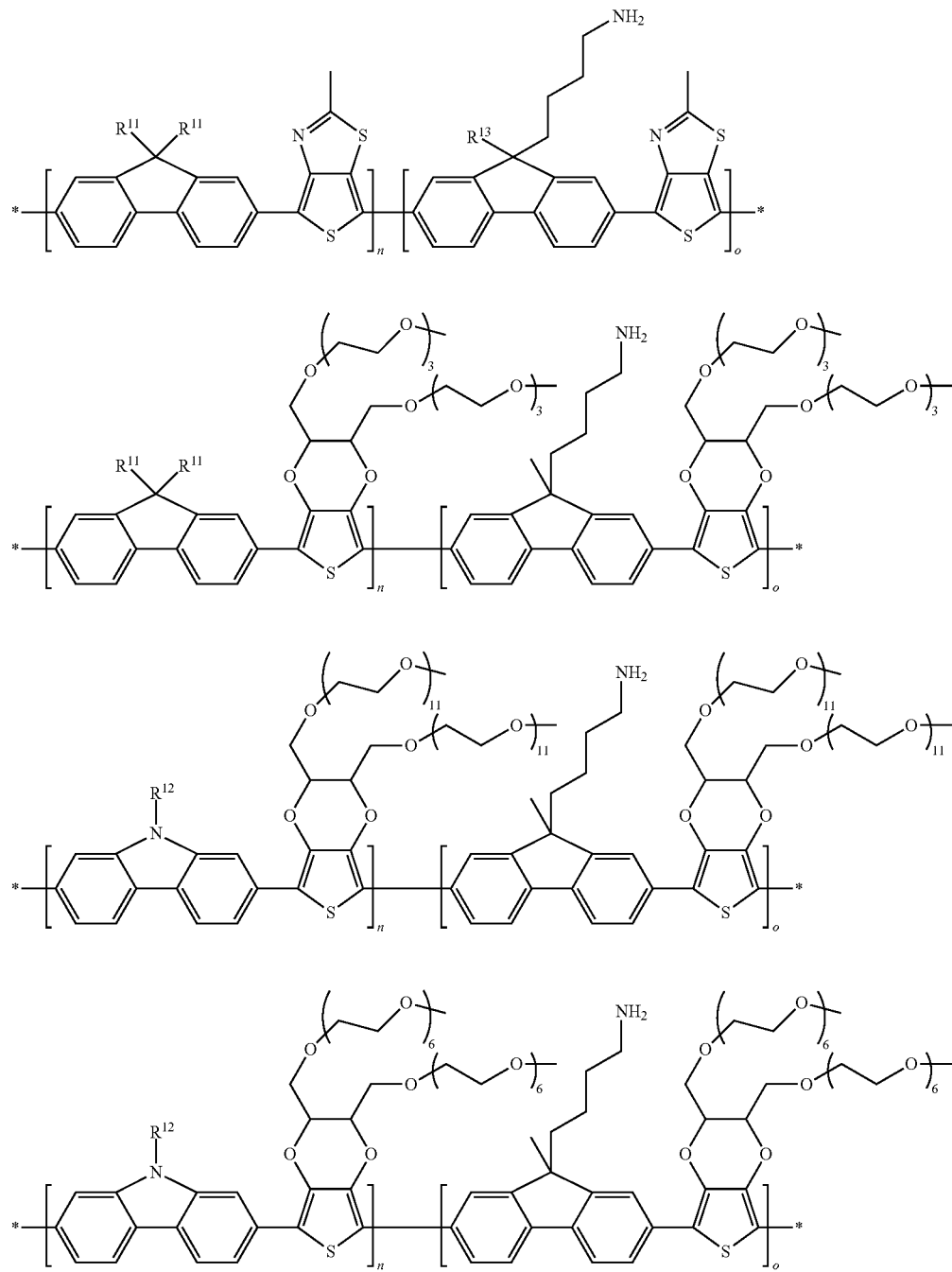

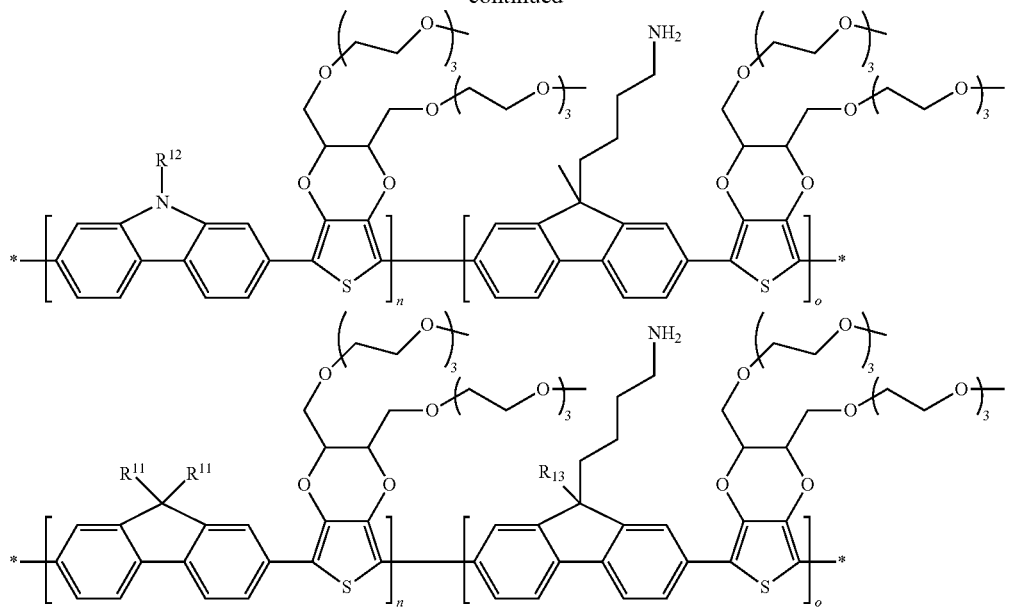

where n and o are independently 1 to 10,000 and each $R^{11}$, $R^{12}$ and $R^{13}$ is independently a substituted alkyl, a substituted aralkyl, or a WSG. In some embodiments of formulae (I), (Ib), (II) and (VI), the polymeric dye includes a conjugated segment having the following structure:

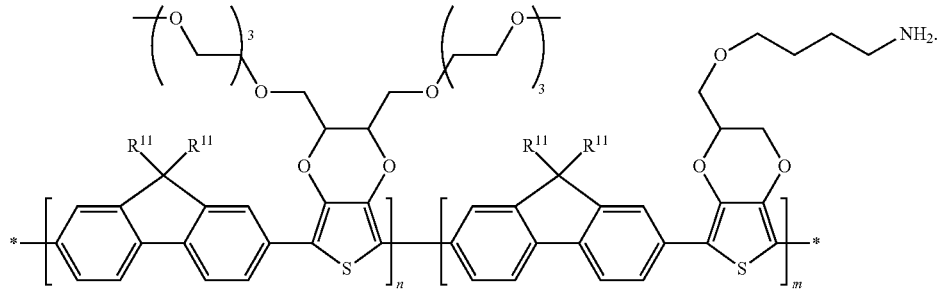

where n and m are independently 1 to 10,000 and each $R^{11}$ is independently a substituted alkyl, a substituted aralkyl, or a WSG. In some embodiments of formulae (I), (Ib), (II) and (VI), the polymeric dye includes a conjugated segment having one of the following structures:

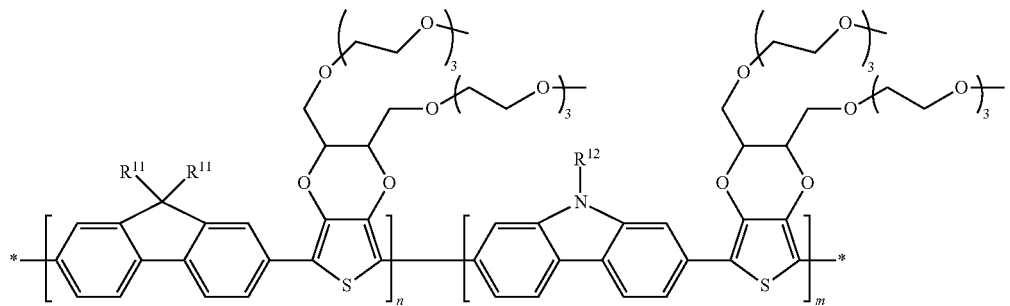

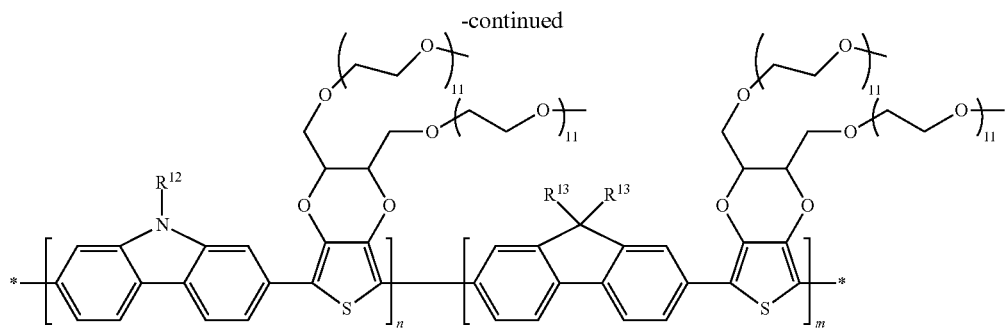

where n and m are independently 1 to 10,000 and each $R^{11}$, $R^{12}$ and $R^{13}$ is independently a substituted alkyl, a substituted aralkyl, or a WSG.

In certain instances, each $R^{11}$, $R^{12}$ and $R^{13}$ of the conjugated segment is independently selected from the following substituents:

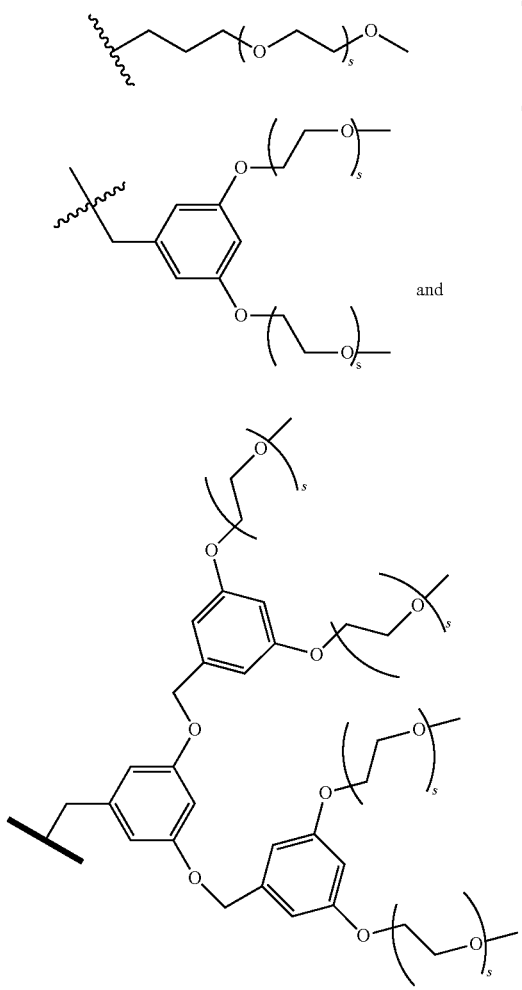

where each s is an integer from 1 to 50. In certain instances, each s is independently 1 to 20, such as 3 to 20, 3 to 15, 3 to 12, or 6 to 12. In certain cases, each s is independently 1, 2, 3, 4, 5, 6, 7, 8, 9, 10, 11 or 12. In some cases, each s is 3. In some cases, each s is 4. In some cases, each s is 5. In some cases, each s is 6. In some cases, each s is 7. In some cases, each s is 8. In some cases, each s is 9. In some cases, each s is 10. In some cases, each s is 11. In certain instances, each $R^{11}$ is substituent (yy), wherein s is 3 to 20 (e.g., 11). In certain instances, each $R^{12}$ is substituent (zz), wherein s is 3 to 20 (e.g., 11). In certain instances, each $R^{13}$ is substituent (xx) wherein s is 3 to 20 (e.g., 11). In certain embodiments of any one of the conjugated segment structures, a terminal of the polymeric dye includes the following linker.

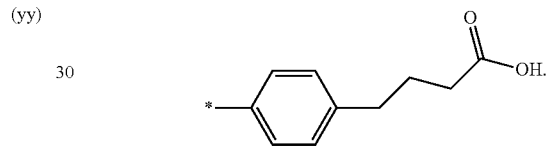

Water Solubilizing Substituents

The subject polymeric dyes may be water solvated. Any convenient water solubilizing groups (WSG's) may be included in the multichromophores described herein (e.g., multichromophores of formulae (I)-(VIb), co-monomers of formulae (VII)-(XVII) and (a)-(q)) to provide for increased water-solubility. While the increase in solubility may vary, in some instances the increase (as compared to the compound without the WSG(s)) is 2 fold or more, e.g., 5 fold, 10 fold, 25 fold, 50 fold, 100 fold or more. As used herein, the terms "water solubilizing group", "water soluble group" and WSG are used interchangeably and refer to a group or substituent that is well solvated in aqueous environments e.g., under physiological conditions, and that imparts improved water solubility upon the molecules to which it is attached. In some embodiments, a WSG increases the solubility of the multichromophore in a predominantly aqueous solution, as compared to a control multichromophore which lacks the WSG. In some instances, the WSGs of the multichromophore are non-ionic side groups capable of imparting solubility in water in excess of 10 mg/mL. The water solubilizing groups may be any convenient hydrophilic group that is well solvated in aqueous environments. In some cases, the hydrophilic water solubilizing group is charged, e.g., positively or negatively charged. In certain cases, the hydrophilic water solubilizing group is a neutral hydrophilic group. In some embodiments, the WSG is a hydrophilic polymer, e.g., a polyethylene glycol, a modified PEG, a peptide sequence, a peptoid, a carbohydrate, an oxazoline, a polyol, a dendron, a dendritic polyglycerol, a cellulose, a chitosan, or a derivative thereof. Water solubilizing groups of interest include, but are not limited to, carboxylate, phosphonate, phosphate, sulfonate, sulfate, sulfinate, sulfonium, ester, polyethylene glycols (PEG) and modified PEGs, hydroxyl, amine, amino acid, ammonium, guanidinium, pyridinium, polyamine and sulfonium, polyalcohols, straight chain or cyclic saccharides, primary, secondary, tertiary, or quaternary amines and polyamines, phosphonate groups, phosphinate groups, ascorbate groups, glycols, including, polyethers, —COOM', —SO$_3$M', —PO$_3$M', —NR$_3^+$, Y', (CH$_2$CH$_2$O)$_p$R and mixtures thereof, where Y' can be any halogen, sulfate, sulfonate, or oxygen containing anion, p can be 1 to 500, each R can be independently H or an alkyl (such as methyl) and M' can be a cationic counterion or hydrogen, —(CH$_2$CH$_2$O)$_{yy}$CH$_2$CH$_2$XR$^{yy}$, —(CH$_2$CH$_2$O)$_{yy}$CH$_2$CH$_2$X—, —X(CH$_2$CH$_2$O)$_{yy}$CH$_2$CH$_2$—, glycol, and polyethylene glycol, wherein yy is selected from 1 to 1000, X is selected from O, S, and NR$^{zz}$, and R$^{zz}$ and R$^{YY}$ are independently selected from H and C$_{1-3}$ alkyl. In some cases, a WSG is (CH$_2$)$_x$(OCH$_2$CH$_2$)$_y$OCH$_3$ where each x is independently an integer from 0-20, each y is independently an integer from 0 to 50. In some cases, the water solubilizing group includes a non-ionic polymer (e.g., a PEG polymer) substituted at the terminal with an ionic group (e.g., a sulfonate). In some embodiments of formulae, the co-monomer includes a substituent selected from (CH$_2$)$_x$(OCH$_2$CH$_2$)$_y$OCH$_3$ where each x is independently an integer from 0-20, each y is independently an integer from 0 to 50; and a benzyl optionally substituted with one or more halogen, hydroxyl, C$_1$-C$_{12}$ alkoxy, or (OCH$_2$CH$_2$)$_z$OCH$_3$ where each z is independently an integer from 0 to 50. In some instances, the substituent is (CH$_2$)$_3$(OCH$_2$CH$_2$)$_{11}$OCH$_3$. In some embodiments, one or more of the substituents is a benzyl substituted with at least one WSG groups (e.g., one or two WSG groups) selected from (CH$_2$)$_x$(OCH$_2$CH$_2$)$_y$OCH$_3$ where each x is independently an integer from 0-20 and each y is independently an integer from 0 to 50.

Multiple WSGs may be included at a single location in the subject multichromophores via a branching linker. In certain embodiments, the branching linker is an aralkyl substituent, further di-substituted with water solubilizing groups. As such, in some cases, the branching linker group is a substituent of the multichromophore that connects the multichromophore to two or more water solubilizing groups. In certain embodiments, the branching linker is an amino acid, e.g., a lysine amino acid that is connected to three groups via the amino and carboxylic acid groups. In some cases, the incorporation of multiple WSGs via branching linkers imparts a desirable solubility on the multichromophore. In some instances, the WSG is a non-ionic sidechain group capable of imparting solubility in water in excess of 10 mg/mL.

In some embodiments, the multichromophore includes substituent(s) selected from the group consisting of, an alkyl, an aralkyl and a heterocyclic group, each group further substituted with a include water solubilizing groups hydrophilic polymer group, such as a polyethylglycol (PEG) (e.g., a PEG group of 2-20 units).

In certain instances of any one of formulae (I)-(XVII) and (a)-(q), one or more of the co-monomers may be substituted with a group (e.g., R$^3$ and R$^4$ substituent groups of the depicted formulae) that is independently selected from H, substituted aryl, alkyl and one of the following structures:

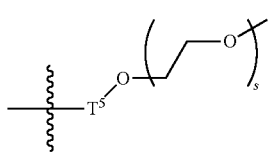

-continued

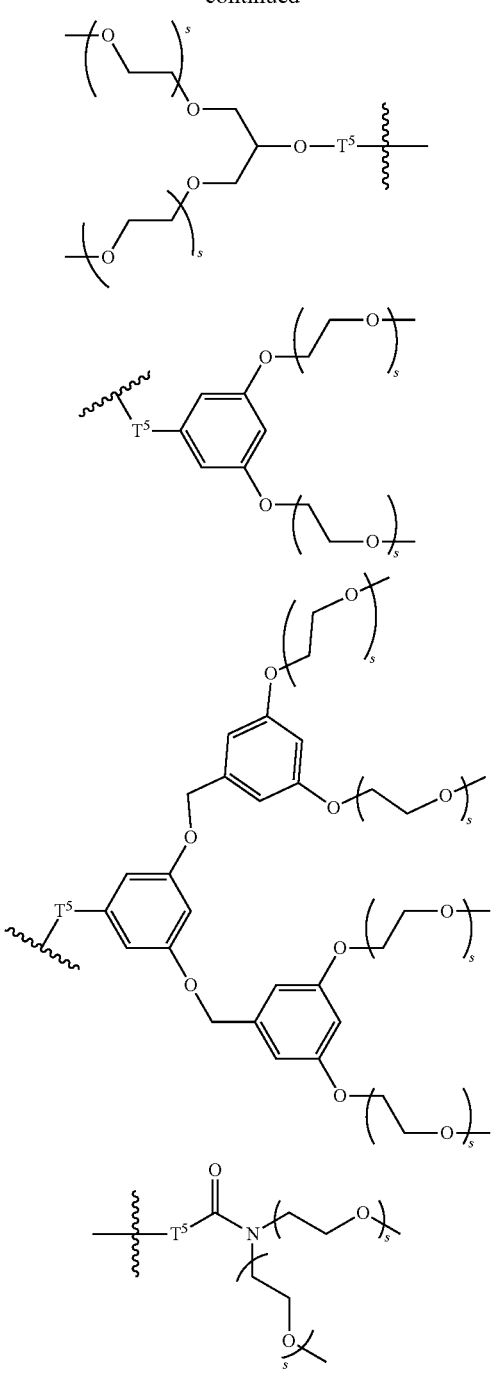

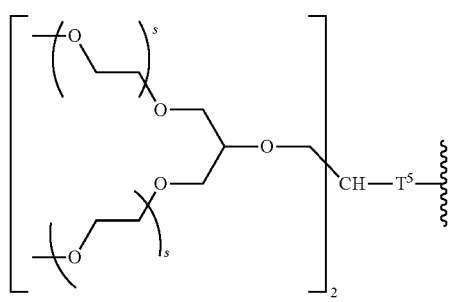

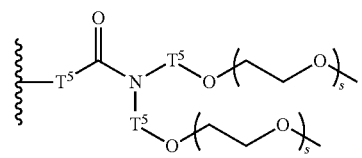

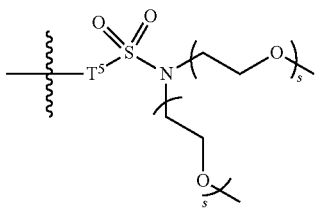

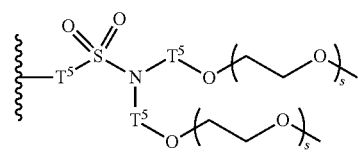

wherein: each $T^5$ is independently an optional linker; and each s is an integer from 1 to 50. In certain instances, each s is independently 1 to 20, such as 3 to 20, 3 to 15, 3 to 12, or 6 to 12. In certain cases, each s is independently 1, 2, 3, 4, 5, 6, 7, 8, 9, 10, 11 or 12. In some cases, each s is 3. In some cases, each s is 4. In some cases, each s is 5. In some cases, each s is 6. In some cases, each s is 7. In some cases, each s is 8. In some cases, each s is 9. In some cases, each s is 10. In some cases, each s is 11. In some cases, each s is 12. In some cases, each s is 14. In some cases, each s is 16. In some embodiments, $T^5$ is an alkyl linker, such as a C1-C6 alkyl linker. In some embodiments, $T^5$ is a substituted alkyl linker. In some embodiments, $T^5$ is an alkoxy linker (e.g., —O-alkyl-). In some embodiments, $T^5$ is a substituted alkoxy. It is understood that hydroxy-terminated PEG chains instead of methoxy-terminated PEG chains may be utilized in any of the WSG groups described herein.

In some cases, a WSG is a dendron selected from one of the following structures:

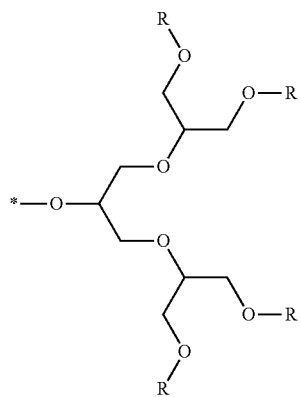

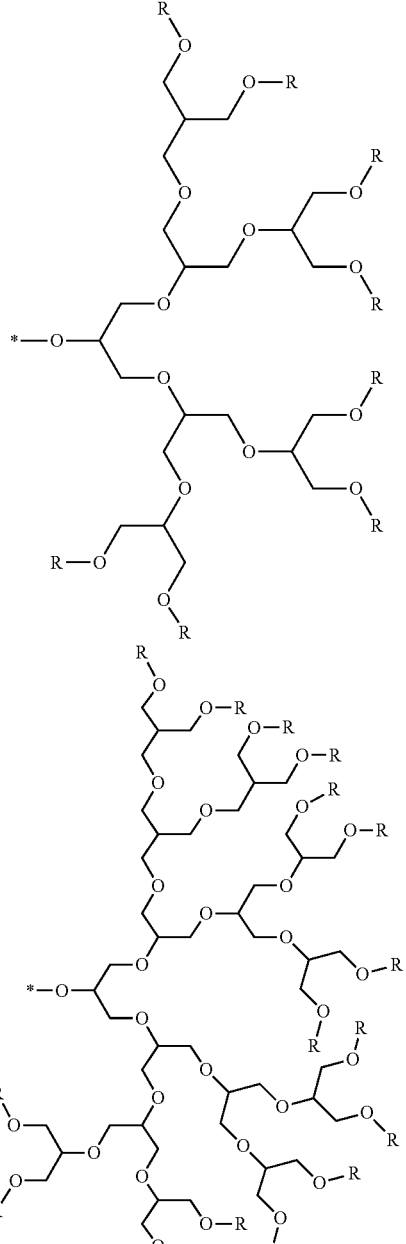

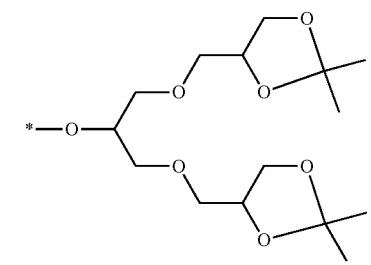

(and higher generations)

where R = H, CH₃    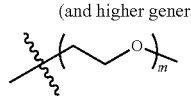

m = 1-16

In some cases, a WSG is a polyol selected from one of the following structures:

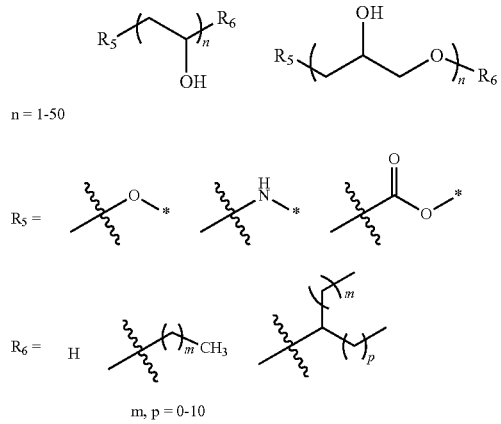

n = 1-50

In some cases, a WSG is an oxazoline of the following structure:

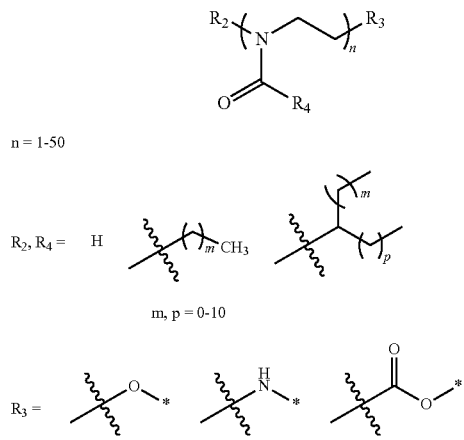

n = 1-50

In some cases, a WSG is a peptiod selected from one of the following structures:

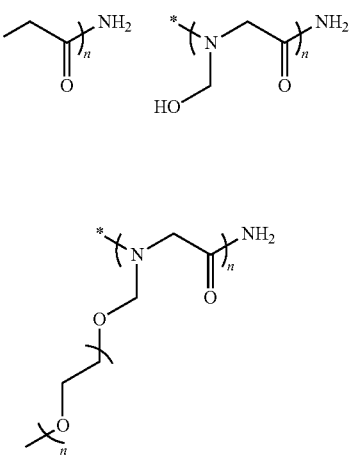

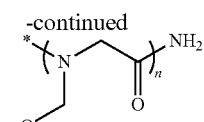
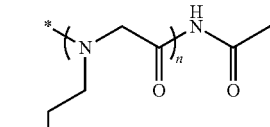
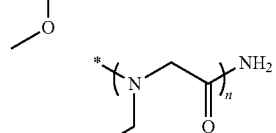
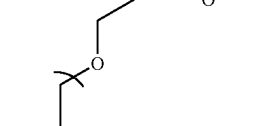
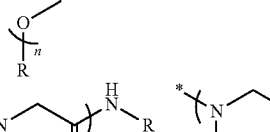

R, H, Me, Ac,

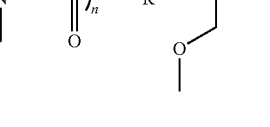
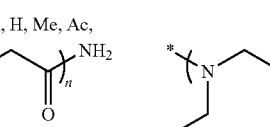
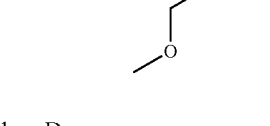

Polymeric Tandem Dyes

The water soluble light harvesting multichromophore can itself be fluorescent and capable of transferring energy to a linked acceptor signaling chromophore. As such, the subject polymeric tandem dyes further include a covalently linked acceptor signaling chromophore in energy-receiving proximity to the donor water solvated light harvesting multichromophore. As such, excitation of the multichromophore donor leads to energy transfer to and emission from the covalently attached acceptor signaling chromophore. The number of signaling chromophore acceptor units that are linked to the donor water solvated light harvesting multichromophore may vary, where in some instances the number ranges from 1 mol % to 50 mol %, such as from 5 mol % to 25 mol % or from 10 mol % to 25 mol %.

Mechanisms for energy transfer from the fluorescent water solvated light harvesting multichromophore donor to the linked acceptor signaling chromophore include, for example, resonant energy transfer (e.g., Förster (or fluorescence) resonance energy transfer, FRET), quantum charge exchange (Dexter energy transfer) and the like. In some instances, these energy transfer mechanisms are relatively short range; that is, close proximity of the light harvesting multichromophore system to the acceptor provides for efficient energy transfer. In some instances, under conditions for efficient energy transfer, amplification of the emission from the acceptor occurs where the emission from the luminescent signaling chromophore is more intense when the incident light (the "pump light") is at a wavelength which is absorbed by the light harvesting multichromophore than when the luminescent signaling chromophore is directly excited by the pump light.

By "efficient" energy transfer is meant 10% or more, such as 20% or more or 30% or more, of the energy harvested by the donor is transferred to the acceptor. By "amplification" is meant that the signal from the signaling chromophore is 1.5× or greater when excited by energy transfer from the donor light harvesting multichromophore as compared to direct excitation with incident light of an equivalent intensity. The signal may be measured using any convenient method. In some cases, the 1.5× or greater signal refers to an intensity of emitted light. In certain cases, the 1.5× or greater signal refers to an increased signal to noise ratio. In certain embodiments of the polymeric tandem dye, the signaling chromophore emission is 1.5 fold greater or more when excited by the multichromophore as compared to direct excitation of the signaling chromophore with incident light, such as 2-fold or greater, 3-fold or greater, 4-fold or greater, 5-fold or greater, 6-fold or greater, 8-fold or greater, 10-fold or greater, 20-fold or greater, 50-fold or greater, 100-fold or greater, or even greater as compared to direct excitation of the signaling chromophore with incident light.

The linked luminescent signaling chromophore emission of the polymeric tandem dye can have a quantum yield of 0.03 or more, such as a quantum yield of 0.04 or more, 0.05 or more, 0.06 or more, 0.07 or more, 0.08 or more, 0.09 or more, 0.1 or more, 0.15 or more, 0.2 or more, 0.3 or more or even more. In some instances, the polymeric tandem dye has an extinction coefficient of $5 \times 10^5$ cm$^{-1}$ M$^{-1}$ or more, such as $6 \times 10^5$ cm$^{-1}$ M$^{-1}$ or more, $7 \times 10^5$ cm$^{-1}$ M$^{-1}$ or more, $8 \times 10^5$ cm$^{-1}$ M$^{-1}$ or more, $9 \times 10^5$ cm$^{-1}$ M$^{-1}$ or more, such as $1 \times 10^6$ cm$^{-1}$ M$^{-1}$ or more, $1.5 \times 10^6$ cm$^{-1}$ M$^{-1}$ or more, $2 \times 10^6$ cm$^{-1}$ M$^{-1}$ or more, $2.5 \times 10^6$ cm$^{-1}$ M$^{-1}$ or more, $3 \times 10^6$ cm$^{-1}$ M$^{-1}$ or more, $4 \times 10^6$ cm$^{-1}$ M$^{-1}$ or more, $5 \times 10^6$ cm$^{-1}$ M$^{-1}$ or more, $6 \times 10^6$ cm$^{-1}$ M$^{-1}$ or more, $7 \times 10^6$ cm$^{-1}$ M$^{-1}$ or more, or $8 \times 10^6$ cm$^{-1}$ M$^{-1}$ or more. In some embodiments, the polymeric tandem dye has a molar extinction coefficient of $5 \times 10^5$ M$^{-1}$ cm$^{-1}$ or more. In certain embodiments, the polymeric tandem dye has a molar extinction coefficient of $1 \times 10^6$ M$^{-1}$ cm$^{-1}$ or more.

The subject polymeric tandem dyes provide for fluorescence emissions from luminescent signaling chromophore dyes that are brighter than the emissions which are possible from such luminescent dyes in isolation. The linked luminescent signaling chromophore emission of the polymeric tandem dye can have a brightness of 50 mM$^{-1}$ cm$^{-1}$ or more, such as 60 mM$^{-1}$ cm$^{-1}$ or more, 70 mM$^{-1}$ cm$^{-1}$ or more, 80 mM$^{-1}$ cm$^{-1}$ or more, 90 mM$^{-1}$ cm$^{-1}$ or more, 100 mM$^{-1}$ cm$^{-1}$ or more, 150 mM$^{-1}$ cm$^{-1}$ or more, 200 mM$^{-1}$ cm$^{-1}$ or more, 250 mM$^{-1}$ cm$^{-1}$ or more, 300 mM$^{-1}$ cm$^{-1}$ or more, or even more. In certain instances, the linked signaling chromophore emission of the polymeric tandem dye has a brightness that is at least 5-fold greater than the brightness of a directly excited luminescent dye, such as at least 10-fold greater, at least 20-fold greater, at least 30-fold greater, at least 50-fold greater, at least 100-fold greater, at least 300-fold greater, or even greater than the brightness of a directly excited luminescent dye.

In some embodiments, a polymeric tandem dye is of one of formula (I)-(VI), where a linked signaling chromophore (e.g., as described herein) is included as a substituent of a co-monomer. In some instances of formula (I)-(VI), the polymeric tandem dye includes one or more co-monomers as described by formula (VII)-(XVII), (a)-(q) and (ba)-(bu). Any convenient signaling chromophore can be attached to any convenient polymer dye described herein via coupling of compatible chemoselective functional groups. The signaling chromophore can be selected to provide for a desirable emission spectra and emission maximum wavelength.

The subject polymeric dyes can include a sidechain chemoselective functional group to which any convenient moiety of interest can be conjugated. Co-monomers which include such a sidechain group can be referred to herein as linking co-monomers.

The polymeric dye can be conjugated to a signaling chromophore to produce a polymeric tandem dye having a desirable spectroscopic properties. In some instances, the multichromophore (e.g., of formulae (I), (II) or (VI)), includes a thiophene-containing co-monomer (e.g., M$^2$ or M$^3$) having a linked chemoselective functional group or a linked acceptor chromophore. In some instances, the multichromophore (e.g., of formulae (I), (II) and (V)), includes a co-monomer having the structure of one of formulae (XVIII)-(XIX):

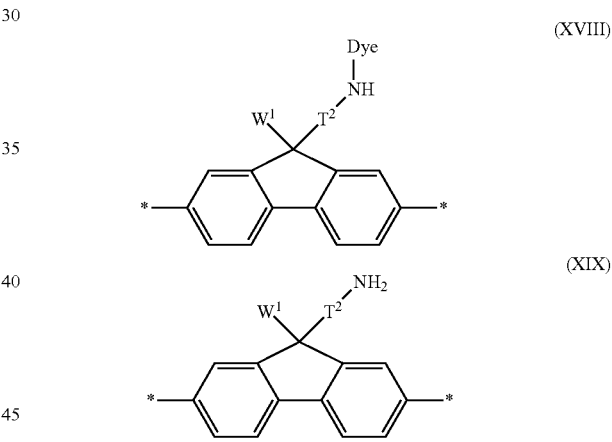

wherein: W$^1$ is an alkyl, a substituted alkyl or a WSG (e.g., as described herein); and Dye is a signaling chromophore. In certain embodiments, the co-monomer is linked to a signaling chromophore and has one of the following structures:

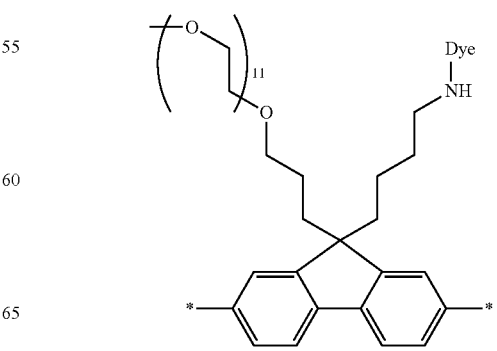

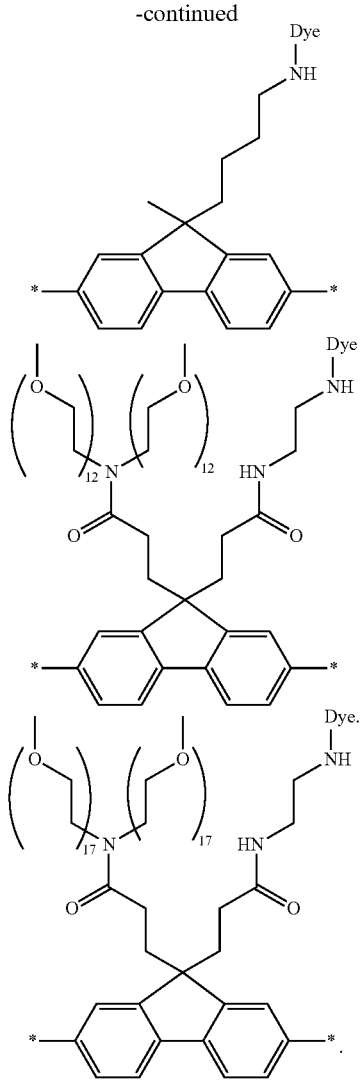

As used herein, the terms "chemoselective functional group" and "chemoselective tag" are used interchangeably and refer to a functional group that can selectively react with another compatible functional group to form a covalent bond, in some cases, after optional activation of one of the functional groups. Any convenient chemoselective tag and conjugation chemistries can be adapted for use in the subject multichromophores. Chemoselective functional groups of interest include, but are not limited to, thiols and thiol-reactive groups such as maleimide, iodoacetamide or vinyl sulfone, amines and carboxylic acids or active esters thereof, as well as groups that can react with one another via Click chemistry, e.g., azide and alkyne groups (e.g., cyclooctyne groups), sulfur(VI) fluoride exchange chemistry (SuFEX), sulfonyl fluoride, tetrazine, alkyne, as well as aldehyde, hydroxyl, hydrazido, hydrazino, aldehyde, ketone, alkoxylamine, phosphine, epoxide, and the like.

Any convenient linking co-monomers may be incorporated into the subject multichromophores to provide for a linking group to which may be attached any convenient moieties of interest (e.g., a linked signaling chromophore). Linking co-monomers of interest include, but are not limited to, those co-monomers described in the formula herein (e.g., formula (XVIII)-(XIX)), a fluorene co-monomer, a phenylenevinylene co-monomer, a phenyleneethynylene co-monomer, a carbazole co-monomer, a $C_2$-$C_{12}$ alkyne co-monomer, an arylene-ethynylene co-monomer, a heteroarylene-ethynylene co-monomer, an arylene co-monomer and a heteroarylene co-monomer. As used herein, the terms aryl or heteroaryl co-monomer and arylene or heteroarylene co-monomer are used interchangeably. In certain cases, the linking co-monomer is a thiophene-containing co-monomer (e.g., as described herein). In certain cases, the linking co-monomer is a substituted aryl or heteroaryl co-monomer, such as a fluorene co-monomer (e.g., as described herein).

In some instances of any of the formula described herein, the signaling chromophore is linked to a co-monomer comprising 1% to 50% by molarity of the multichromophore, such as 1% to 20%, 1% to 10%, or 11 to 20% by molarity. In certain cases, the multichromophore is a conjugated polymer comprising 5 or more repeat units.

Any convenient chemoselective functional groups may be included in the subject multichromophores (e.g., at the —$Z^1$, —$Z^2$ and/or in the $G^1$ or $G^2$ terminal groups, including, but are not limited to, carboxylic acid, active ester (e.g., NHS or sulfo-NHS ester), amino, hydroxyl, thiol, maleimide, iodoacetyl, hydrazido, hydrazino, aldehyde, ketone, azido, alkyne, phosphine and epoxide. In some cases, the chemoselective functional group or linker can be connected directed to a terminal co-monomer. It is understood that in the polymeric tandem dye structures described herein, in some cases, the groups $Z^1$ and $Z^2$ appear at a equivalent position in the structure where these groups can be used interchangeably to refer to either a linked signaling chromophore or a chemoselective functional group that is capable of subsequent conjugation to a convenient chromophore precursor to produce the linked signaling chromophore.

In some cases, the signaling chromophore is a fluorophore. In certain cases, the signaling chromophore is a quencher. Any convenient fluorescent dyes may be utilized in the polymeric tandem dyes as an acceptor chromophore. The terms "fluorescent dye" and "fluorophore" are used interchangeably herein. The signaling chromophore ($Z^1$) can be a dye molecule selected from a rhodamine, a coumarin, a xanthene, a cyanine, a polymethine, a pyrene, a dipyrromethene borondifluoride, a napthalimide, a phycobiliprotein, a peridinum chlorophyll protein, conjugates thereof, and combinations thereof. In certain embodiments, the signaling chromophore ($Z^1$) is a cyanine dye, a xanthene dye, a coumarin dye, a thiazine dye and an acridine dye. In some instances, the signaling chromophore ($Z^1$) is selected from DY 431, DY 485XL, DY 500XL, DY 610, DY 640, DY 654, DY 682, DY 700, DY 701, DY 704, DY 730, DY 731, DY 732, DY 734, DY 752, DY 778, DY 782, DY 800, DY 831, Biotium CF 555, Cy 3.5 and diethylamino coumarin. In some embodiments, the acceptor chromophore is a cyanine dye, a xanthene dye, a coumarin dye, a thiazine dye or an acridine dye. Fluorescent dyes of interest include, but are not limited to, fluorescein, 6-FAM, rhodamine, Texas Red, tetramethylrhodamine, carboxyrhodamine, carboxyrhodamine 6G, carboxyrhodol, carboxyrhodamine 110, Cascade Blue, Cascade Yellow, coumarin, Cy2, Cy3, Cy3.5, Cy5, Cy5.5, Cy-Chrome, phycoerythrin, PerCP (peridinin chlorophyll-a Protein), PerCP-Cy5.5, JOE (6-carboxy-4',5'-dichloro-2',7'-dimethoxyfluorescein), NED, ROX (5-(and-6)-carboxy-X-rhodamine), HEX, Lucifer Yellow, Marina Blue, Oregon Green 488, Oregon Green 500, Oregon Green 514, Alexa Fluor 350, Alexa Fluor 430, Alexa Fluor 488, Alexa Fluor 532, Alexa Fluor 546, Alexa Fluor 568, Alexa Fluor 594, Alexa Fluor 633, Alexa Fluor 647, Alexa Fluor 660, Alexa Fluor 680, Alexa Fluor 700, 7-amino-4-methylcoumarin-3-acetic acid, BODIPY FL, BODIPY FL-Br.sub.2, BODIPY 530/550, BODIPY 558/568, BODIPY 564/570, BODIPY 576/589, BODIPY 581/591, BODIPY 630/650, BODIPY 650/665, BODIPY R6G, BODIPY TMR, BODIPY TR, conjugates thereof, and combinations thereof. Lanthanide chelates of interest include, but are not limited to, europium chelates, terbium chelates and samarium chelates. In some embodiments, the polymeric tandem dye includes a polymeric dye linked to an acceptor fluorophore selected from Cy3, Cy3.5, Cy5, Cy5.5, Cy7, Alexa488, Alexa 647 and Alexa700. In certain embodiments, the polymeric tandem dye includes a polymeric dye linked to an acceptor fluorophore selected from Dyomics dyes (such as DY 431, DY 485XL, DY 500XL, DY 530, DY 610, DY 633, DY 640, DY 651, DY 654, DY 682, DY 700, DY 701, DY 704, DY 730, DY 731, DY 732, DY 734, DY 752, DY 754, DY 778, DY 782, DY 800 or DY 831), Biotium CF 555, Cy 3.5, and diethylamino coumarin.

In some embodiments, the signaling chromophore that is selected has an emission maximum wavelength in the range of 300 to 900 nm, such as 350 to 850 nm, 350 to 600 nm, 360 to 500 nm, 370 to 500 nm, 380 to 500 nm, 390 to 500 nm or 400 to 500 nm, where specific examples of emission maxima of signaling chromophore of interest include, but are not limited to: 395 nm±5 nm, 420 nm±5 nm, 430 nm±5 nm, 440 nm±5 nm, 450 nm±5 nm, 460 nm±5 nm, 470 nm±5 nm, 480 nm±5 nm, 490 nm±5 nm, 500 nm±5 nm, 510 nm±5 nm, 520 nm±5 nm, 530 nm±5 nm, 540 nm±5 nm, 550 nm±5 nm, 560 nm±5 nm, 570 nm±5 nm, 580 nm±5 nm, 590 nm±5 nm, 605 nm±5 nm, 650 nm±5 nm, 680 nm±5 nm, 700 nm±5 nm, 805 nm±5 nm.

End Groups

Any convenient end groups (e.g., $G^1$ and $G^2$) may be utilized at the terminals of the subject multichromophores. As used herein, the terms "end group" and "terminal group" are used interchangeably to refer to the groups located at the terminals of the polymeric structure of the multichromophore, e.g., as described herein. $G^1$ and $G^2$ groups of interest include, but are not limited to a terminal capping group, a π conjugated segment, a linker and a linked specific binding member. In some embodiments, a terminal capping groups is a monovalent group which is conjugated to the backbone of the multichromophore after polymerization. In certain instances, the terminal capping group is an aryl, a substituted aryl, a heteroaryl, a substituted heteroaryl, an alkyl or a substituted alkyl. In certain cases, the terminal capping group is derived from a monomer used in the method of polymerization, e.g., a terminal group such as a halogen (e.g., Br), a boronic acid or a boronic ester, which is capable of undergoing further conjugation. In some instances, $G^1$ and/or $G^2$ is a π conjugated segment. As used herein, a π conjugated segment refers to any convenient segment of a conjugated polymer to which the multichromophore may be conjugated, i.e., allowing delocalization of pi electron across adjacent units. In certain embodiments, $G^1$ and/or $G^2$ is a linker, such as a linker including a functional group suitable for conjugation to a specific binding moiety. It is understood that linkers located at the $G^1$ and/or $G^2$ positions of the multichromophore may be selected so as to be orthogonal to any other linkers including chemoselective tags that may be present at a sidechain of the multichromophore (e.g., at $Z^2$). In certain embodiments, an amino functional group or derivative thereof is included at $G^1$ and/or $G^2$ and a carboxylic acid functional group or derivative thereof is included at $Z^2$. In some embodiments, a carboxylic acid functional group or derivative thereof is included at $G^1$ and/or $G^2$ and an amino functional group or derivative thereof is included at $Z^2$.

In some embodiments of the formulae described herein, at least one of $G^1$ and $G^2$ is $-L^3-Z^4$ where $L^3$ is a linker (e.g., as described herein) and $Z^4$ is a specific binding member (e.g., as described herein). In some embodiments of formulae described herein, at least one of $G^1$ and $G^2$ is $-L^3-Z^3$ where $L^3$ is a linker (e.g., as described herein) and $Z^3$ is a chemoselective tag (e.g., as described herein). In some instances, $Z^3$ is selected from carboxylic acid, active ester (e.g., N-hydroxy succinimidyl ester (NHS) or sulfo-NHS), amino, maleimide, iodoacetyl and thiol. In some instances, $Z^3$ is a chemoselective functional group that finds us in a bioorthogonal conjugation chemistry, such as an azide or an alkyne (e.g., a cyclooctyne), sulfur(VI) fluoride exchange chemistry (SuFEX), sulfonyl fluoride or a tetrazine. In certain embodiments of formulae described herein, at least one of $G^1$ and $G^2$ is described by the following structure:

*—Ar-L-Z where Ar is a π-conjugated aryl group, L is a linker and Z is a chemoselective tag or a specific binding member. In some cases, the L-Z group can be connected directed to a terminal co-monomer. In certain embodiments of formulae described herein, at least one of $G^1$ and $G^2$ is described by the following structure:

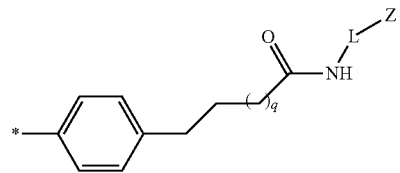

wherein:
q is 0 or an integer from 1-12;
L is an optional linker; and
Z is a chemoselective tag or a specific binding member. In certain embodiments, Z is a biomolecule. Biomolecules of interest include, but are not limited to, polypeptides, polynucleotides, carbohydrates, fatty acids, steroids, purines, pyrimidines, derivatives, structural analogs thereof and combinations thereof. In certain instances, Z is an antibody. In some instances, Z is an antibody fragment or binding derivative thereof. In some cases, the antibody fragment or binding derivative thereof is selected from the group consisting of a Fab fragment, a F(ab')$_2$ fragment, a scFv, a diabody and a triabody. Z can be any convenient chemoselective tag. In some instances, Z is a chemoselective functional group that finds use in a bioorthogonal Click chemistry, such as an azide or an alkyne (e.g., a cyclooctyne), a tetrazine or an alkyne, or a sulfonyl fluoride. In some cases, Z is selected from carboxylic acid, active ester (e.g., N-hydroxy succinimidyl ester (NHS) or sulfo-NHS), amino, hydroxyl, hydrazido, hydrazino, aldehyde, ketone, alkoxylamine, azido, alkyne, phosphine, epoxide maleimide, iodoacetyl and thiol.

It is understood that for any of the structures and formula depicted herein that in some cases of the subject multichromophore the end groups depicted may be located at the opposite ends to those shown, e.g., the end groups $G^1$ and -Ph-L-Z may be switched. In some embodiments of the multichromophores described herein (e.g., formulae (I)-(VIb), at least one of $G^1$ and $G^2$ is selected from one of the following structures 1-33:

| | |
|---|---|
| 1 | 2 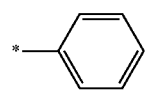 |
| *—H | |
| *—Br | 3 *—Cl | 4 |
| *—I | 5 *—SH | 6 |
| 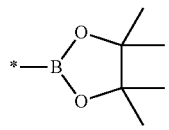 | 7 *—B(OH)$_2$ | 8 |
| 9 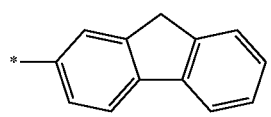 | 10 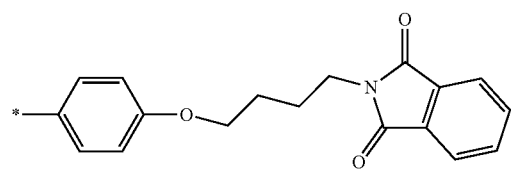 |
| 11 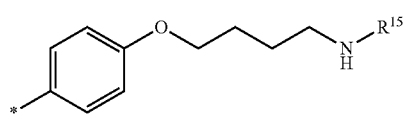 | 12 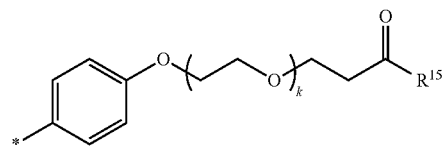 |
| 13 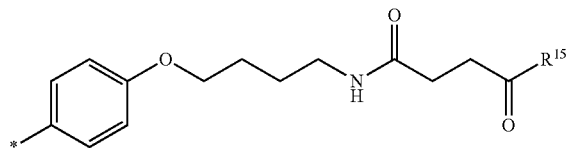 | 14 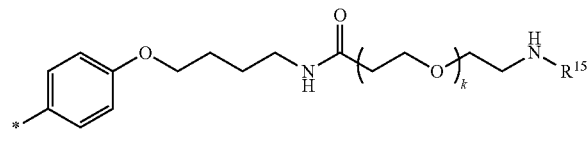 |
| 15 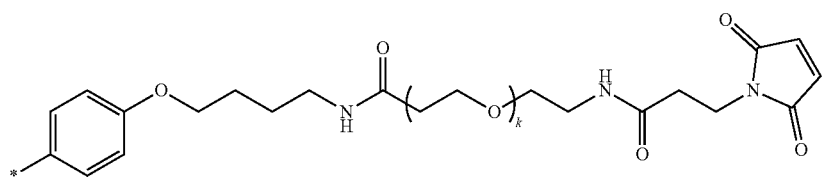 | |
| 16 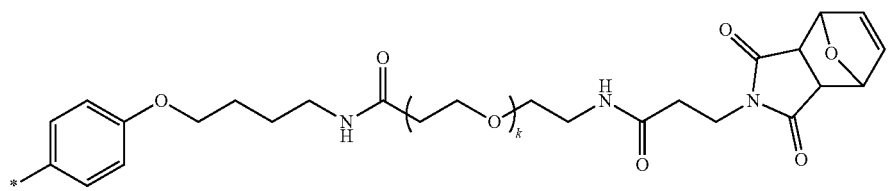 | |
| 17 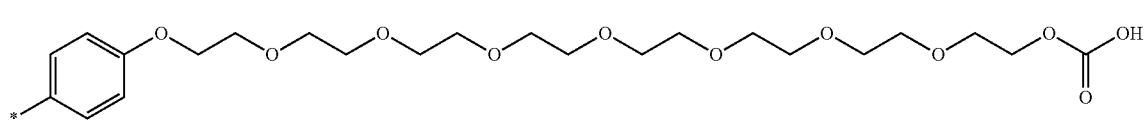 | |
| 18 * | 19 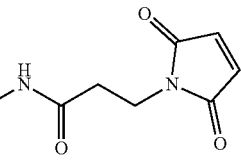 |
| 20 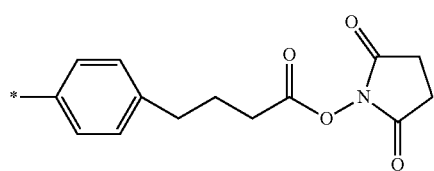 | 21 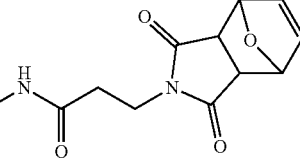 |

-continued

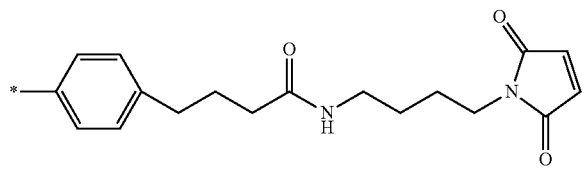
22

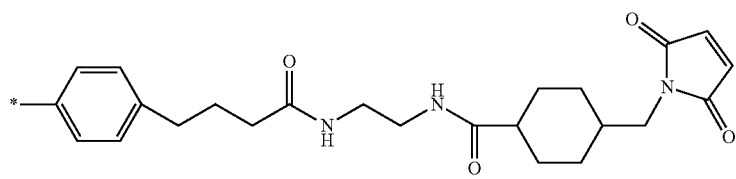
23

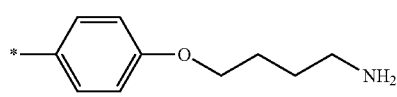
24

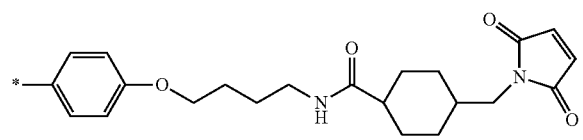
25

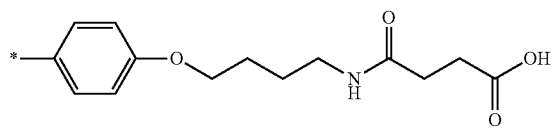
26

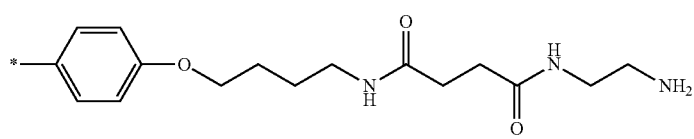
27

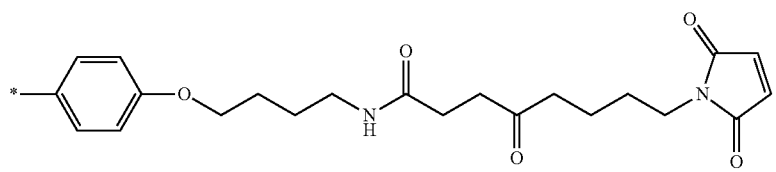
28

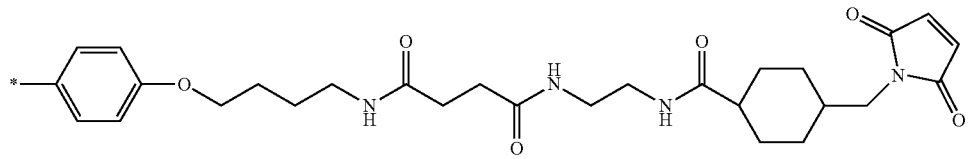
29

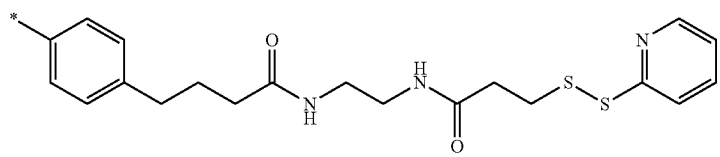
30

31

*=site for covalent attachment to unsaturated backbone; wherein R' is independently H, halogen, $C_1$-$C_{12}$ alkyl, ($C_1$-$C_{12}$ alkyl)$NH_2$, $C_2$-$C_{12}$ alkene, $C_2$-$C_{12}$ alkyne, $C_3$-$C_{12}$cycloalkyl, $C_1$-$C_{12}$ haloalkyl, $C_2$-$C_{18}$(hetero)aryl, $C_2$-$C_{18}$(hetero)arylamino, —[$CH_2$—$CH_2$]$_r$—$Z^1$, or ($C_1$-$C_{12}$)alkoxy-$X^1$; and wherein $Z^1$ is —OH or —COOH; $X^1$ is —$NH_2$, —NHCOOH, —NHCOOC($CH_3$)$_3$, —NHCO(C3-C12)cycloalkyl(C1-C4)alkyl-N-maleimide; or —NHCO

[CH$_2$—CH$_2$—O]$_{s'}$(CH$_2$)$_{s'}$—NH$_2$; r' is an integer from 1 to 20; and each s' is independently an integer from 1 to 20, (CH$_2$)$_3$(OCH$_2$CH$_2$)$_{x''}$OCH$_3$ where x" is independently an integer from 0 to 50, or a benzyl optionally substituted with one or more halogen, hydroxyl, C$_1$-C$_{12}$ alkoxy, or (OCH$_2$CH$_2$)$_{y''}$CH$_3$ where each y" is independently an integer from 0 to 50 and R' is different from R;
wherein k is 2, 4, 8, 12 or 24;
wherein R$^{15}$ is selected from the group consisting of I-u having the structure:

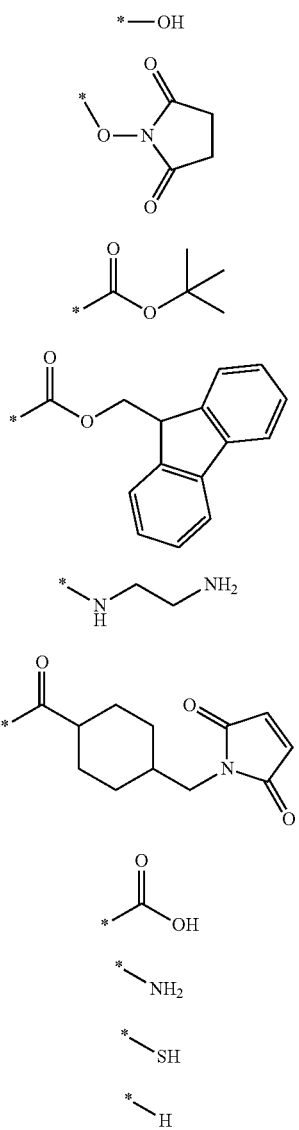

l
m
n
o
p
q
r
s
t
u

*=site for covalent attachment to backbone.

In some embodiments of the multichromophores described herein (e.g., formulae formulae (I)-(VIb), at least one end group (e.g., T$^2$-Z$^2$, G$^1$, G$^2$, -L-Z, -L$^3$-Z), or side-chain group, is selected from one of the following structures:

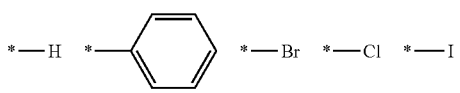

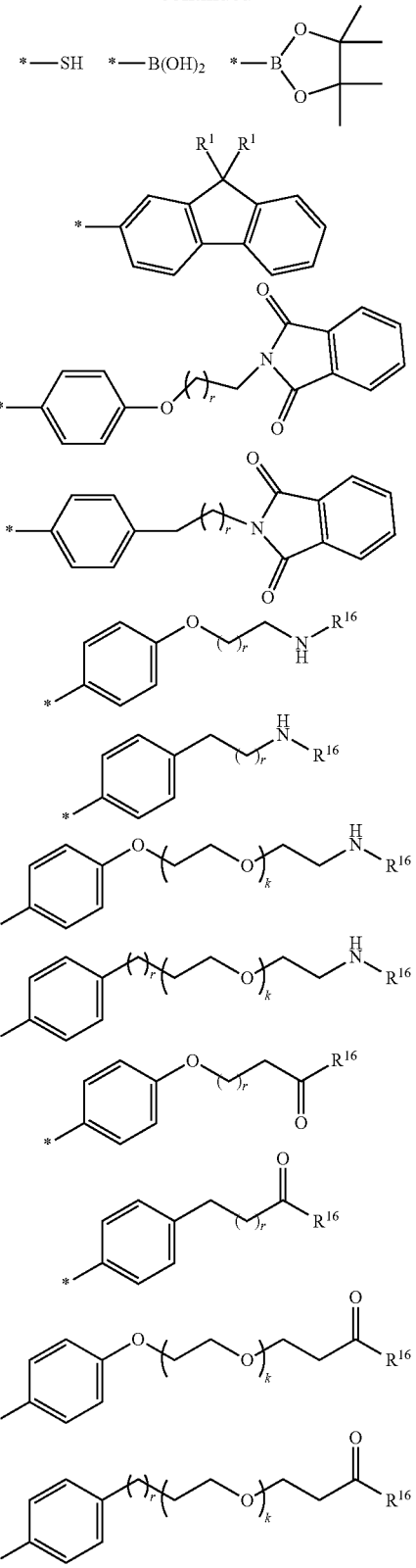

wherein r is 0 or an integer from 1-50; k is 0 or an integer from 1-50 (e.g., 1-20); R$^1$ is as defined for any of the fluorene co-monomers described herein; and R$^{16}$ is selected from H, OH, NH$_2$, —NH(CH$_2$)r-NH$_2$, and —NH(CH$_2$)$_1$COOH. In certain instances, r is 1 to 20, such as 3 to 20, 3 to 15, 3 to 12, or 6 to 12. In certain cases, r is 1, 2, 3, 4, 5, 6, 7, 8, 9, 10, 11 or 12. In some cases, r is 3. In some cases, r is 4. In some cases, r is 5. In some cases, r is 6. In some cases, r is 7. In some cases, r is 8. In some cases, r is 9. In some cases, r is 10. In some cases, r is 11. In some embodiments of the multichromophores described herein (e.g., formulae (I)-(VIb), at least one end group (e.g., T$^2$-Z$^2$, G$^1$, G$^2$, -L-Z, -L$^3$-Z) is

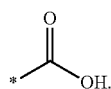

Labelled Specific Binding Members

Aspects of the present disclosure include labelled specific binding members. A labelled specific binding member is a conjugate of a subject polymeric dye (e.g., as described herein) and a specific binding member. Any of the polymeric dyes and polymeric tandem dyes described herein may be conjugated to a specific binding member. The specific binding member and the polymeric dye can be conjugated (e.g., covalently linked) to each other at any convenient locations of the two molecules, via an optional linker. In certain instances, at least one of the terminal groups of the polymeric dye (e.g., G$^1$ or G$^2$) includes a linked specific binding member.

As used herein, the term "specific binding member" refers to one member of a pair of molecules which have binding specificity for one another. One member of the pair of molecules may have an area on its surface, or a cavity, which specifically binds to an area on the surface of, or a cavity in, the other member of the pair of molecules. Thus the members of the pair have the property of binding specifically to each other to produce a binding complex. In some embodiments, the affinity between specific binding members in a binding complex is characterized by a K$_d$ (dissociation constant) of 10$^{-6}$ M or less, such as 10$^{-7}$ M or less, including 10$^{-8}$ M or less, e.g., 10$^{-9}$ M or less, 10$^{-10}$ M or less, 10$^{-11}$ M or less, 10$^{-12}$ M or less, 10$^{-13}$ M or less, 10$^{-14}$ M or less, including 10$^{-15}$ M or less. In some embodiments, the specific binding members specifically bind with high avidity. By high avidity is meant that the binding member specifically binds with an apparent affinity characterized by an apparent K$_d$ of 10×10$^{-9}$ M or less, such as 1×10$^{-9}$ M or less, 3×10$^{-10}$ M or less, 1×10$^{-10}$ M or less, 3×10$^{-11}$ M or less, 1×10$^{-11}$ M or less, 3×10$^{-12}$ M or less or 1×10$^{-12}$ M or less.

The specific binding member can be proteinaceous. As used herein, the term "proteinaceous" refers to a moiety that is composed of amino acid residues. A proteinaceous moiety can be a polypeptide. In certain cases, the proteinaceous specific binding member is an antibody. In certain embodiments, the proteinaceous specific binding member is an antibody fragment, e.g., a binding fragment of an antibody that specific binds to a polymeric dye. As used herein, the terms "antibody" and "antibody molecule" are used interchangeably and refer to a protein consisting of one or more polypeptides substantially encoded by all or part of the recognized immunoglobulin genes. The recognized immunoglobulin genes, for example in humans, include the kappa (k), lambda (l), and heavy chain genetic loci, which together comprise the myriad variable region genes, and the constant region genes mu (u), delta (d), gamma (g), sigma (e), and alpha (a) which encode the IgM, IgD, IgG, IgE, and IgA isotypes respectively. An immunoglobulin light or heavy chain variable region consists of a "framework" region (FR) interrupted by three hypervariable regions, also called "complementarity determining regions" or "CDRs". The extent of the framework region and CDRs have been precisely defined (see, "Sequences of Proteins of Immunological Interest," E. Kabat et al., U.S. Department of Health and Human Services, (1991)). The numbering of all antibody amino acid sequences discussed herein conforms to the Kabat system. The sequences of the framework regions of different light or heavy chains are relatively conserved within a species. The framework region of an antibody, that is the combined framework regions of the constituent light and heavy chains, serves to position and align the CDRs. The CDRs are primarily responsible for binding to an epitope of an antigen. The term antibody is meant to include full length antibodies and may refer to a natural antibody from any organism, an engineered antibody, or an antibody generated recombinantly for experimental, therapeutic, or other purposes as further defined below.

Antibody fragments of interest include, but are not limited to, Fab, Fab', F(ab')2, Fv, scFv, or other antigen-binding subsequences of antibodies, either produced by the modification of whole antibodies or those synthesized de novo using recombinant DNA technologies. Antibodies may be monoclonal or polyclonal and may have other specific activities on cells (e.g., antagonists, agonists, neutralizing, inhibitory, or stimulatory antibodies). It is understood that the antibodies may have additional conservative amino acid substitutions which have substantially no effect on antigen binding or other antibody functions.

In certain embodiments, the specific binding member is a Fab fragment, a F(ab')$_2$ fragment, a scFv, a diabody or a triabody. In certain embodiments, the specific binding member is an antibody. In some cases, the specific binding member is a murine antibody or binding fragment thereof. In certain instances, the specific binding member is a recombinant antibody or binding fragment thereof.

In some embodiments, the labelled specific binding member includes: a water solvated light harvesting multichromophore (e.g., as described herein); and a signaling chromophore covalently linked to the multichromophore in energy-receiving proximity therewith (e.g., as described herein); and a specific binding member covalently linked to the multichromophore. In some instances of the labelled specific binding member, the multichromophore of any of the formula described herein (e.g., formulae (V) and (VII)-(VIII)), wherein: G$^1$ and G$^2$ are each independently selected from a terminal group (e.g., end group), a π conjugated segment, a linker and a linked specific binding member, wherein at least one of G$^1$ and G$^2$ is a linked specific binding member.

Methods

As summarized above, aspects of the invention include methods of evaluating a sample for the presence of a target analyte. Aspects of the method include contacting the sample with a polymeric dye conjugate that specifically binds the target analyte to produce a labelling composition contacted sample. As used herein, the terms "polymeric dye conjugate" and "labelled specific binding member" are used interchangeably. As such, the polymeric dye conjugate can include: (i) a water solvated polymeric dye (e.g., as described herein); and (ii) a specific binding member (e.g., as described herein). In some instances, the polymeric dye conjugate further comprises a signaling chromophore covalently linked to a multichromophore of the polymeric dye in energy-receiving proximity therewith.

Any convenient method may be used to contact the sample with a polymeric dye conjugate that specifically binds to the target analyte to produce the labelling composition contacted sample. In some instances, the sample is contacted with the polymeric dye conjugate under conditions in which the specific binding member specifically binds to the target analyte, if present. For specific binding of the specific binding member of the conjugate with the target analyte, an appropriate solution may be used that maintains the biological activity of the components of the sample and the specific binding member. The solution may be a balanced salt solution, e.g., normal saline, PBS, Hank's balanced salt solution, etc., conveniently supplemented with fetal calf serum, human platelet lysate or other factors, in conjunction with an acceptable buffer at low concentration, such as from 5-25 mM. Convenient buffers include HEPES, phosphate buffers, lactate buffers, etc. Various media are commercially available and may be used according to the nature of the target analyte, including dMEM, HBSS, dPBS, RPMI, Iscove's medium, etc., in some cases supplemented with fetal calf serum or human platelet lysate. The final components of the solution may be selected depending on the components of the sample which are included.

The temperature at which specific binding of the specific binding member of the conjugate to the target analyte takes place may vary, and in some instances may range from 5° C. to 50° C., such as from 10° C. to 40° C., 15° C. to 40° C., 20° C. to 40° C., e.g., 20° C., 25° C., 30° C., 35° C. or 37° C. (e.g., as described above). In some instances, the temperature at which specific binding takes place is selected to be compatible with the biological activity of the specific binding member and/or the target analyte. In certain instances, the temperature is 25° C., 30° C., 35° C. or 37° C. In certain cases, the specific binding member is an antibody or fragment thereof and the temperature at which specific binding takes place is room temperature (e.g., 25° C.), 30° C., 35° C. or 37° C. Any convenient incubation time for specific binding may be selected to allow for the formation of a desirable amount of binding complex, and in some instances, may be 1 minute (min) or more, such as 2 min or more, 10 min or more, 30 min or more, 1 hour or more, 2 hours or more, or even 6 hours or more.

Any convenient specific binding members may be utilized in the conjugate. Specific binding members of interest include, but are not limited to, those agents that specifically bind cell surface proteins of a variety of cell types, including but not limited to, stem cells, e.g., pluripotent stem cells, hematopoietic stem cells, T cells, T regulator cells, dendritic cells, B Cells, e.g., memory B cells, antigen specific B cells, granulocytes, leukemia cells, lymphoma cells, virus cells (e.g., HIV cells) NK cells, macrophages, monocytes, fibroblasts, epithelial cells, endothelial cells, and erythroid cells. Target cells of interest include cells that have a convenient cell surface marker or antigen that may be captured by a convenient specific binding member conjugate. In some embodiments, the target cell is selected from HIV containing cell, a Treg cell, an antigen-specific T-cell populations, tumor cells or hematopoetic progenitor cells (CD34+) from whole blood, bone marrow or cord blood. Any convenient cell surface proteins or cell markers may be targeted for specific binding to polymeric dye conjugates in the subject methods. In some embodiments, the target cell includes a cell surface marker selected from a cell receptor and a cell surface antigen. In some cases, the target cell may include a cell surface antigen such as CD11b, CD123, CD14, CD15, CD16, CD19, CD193, CD2, CD25, CD27, CD3, CD335, CD36, CD4, CD43, CD45RO, CD56, CD61, CD7, CD8, CD34, CD1c, CD23, CD304, CD235a, T cell receptor alpha/beta, T cell receptor gamma/delta, CD253, CD95, CD20, CD105, CD117, CD120b, Notch4, Lgr5 (N-Terminal), SSEA-3, TRA-1-60 Antigen, Disialoganglioside GD2 and CD71.

Any convenient targets may be selected for evaluation utilizing the subject methods. Targets of interest include, but are not limited to, a nucleic acid, such as an RNA, DNA, PNA, CNA, HNA, LNA or ANA molecule, a protein, such as a fusion protein, a modified protein, such as a phosphorylated, glycosylated, ubiquitinated, SUMOylated, or acetylated protein, or an antibody, a peptide, an aggregated biomolecule, a cell, a small molecule, a vitamin and a drug molecule. As used herein, the term "a target protein" refers to all members of the target family, and fragments thereof. The target protein may be any protein of interest, such as a therapeutic or diagnostic target, including but not limited to: hormones, growth factors, receptors, enzymes, cytokines, osteoinductive factors, colony stimulating factors and immunoglobulins. The term "target protein" is intended to include recombinant and synthetic molecules, which can be prepared using any convenient recombinant expression methods or using any convenient synthetic methods, or purchased commercially. In some embodiments, the polymeric dye conjugates include an antibody or antibody fragment. Any convenient target analyte that specifically binds an antibody or antibody fragment of interest may be targeted in the subject methods.

In some embodiments, the target analyte is associated with a cell. In certain instances, the target analyte is a cell surface marker of the cell. In certain cases, the cell surface marker is selected from the group consisting of a cell receptor and a cell surface antigen. In some instances, the target analyte is an intracellular target, and the method further includes lysing the cell.

In some embodiments, the sample may include a heterogeneous cell population from which target cells are isolated. In some instances, the sample includes peripheral whole blood, peripheral whole blood in which erythrocytes have been lysed prior to cell isolation, cord blood, bone marrow, density gradient-purified peripheral blood mononuclear cells or homogenized tissue. In some cases, the sample includes hematopoetic progenitor cells (e.g., CD34+ cells) in whole blood, bone marrow or cord blood. In certain embodiments, the sample includes tumor cells in peripheral blood. In certain instances, the sample is a sample including (or suspected of including) viral cells (e.g., HIV).

The labelled specific binding members find use in the subject methods, e.g., for labeling a target cell, particle, target or analyte with a polymeric dye or polymeric tandem dye. For example, labelled specific binding members find use in labeling cells to be processed (e.g., detected, analyzed, and/or sorted) in a flow cytometer. The labelled specific binding members may include antibodies that specifically bind to, e.g., cell surface proteins of a variety of cell types (e.g., as described herein). The labelled specific binding members may be used to investigate a variety of biological (e.g., cellular) properties or processes such as cell cycle, cell proliferation, cell differentiation, DNA repair, T cell signaling, apoptosis, cell surface protein expression and/or presentation, and so forth. Labelled specific binding members may be used in any application that includes (or may include) antibody-mediated labeling of a cell, particle or analyte.

In some instances of the method, the labelled specific binding member includes a multichromophore according to any one of formulae (I)-(VI) (e.g., as described herein). In certain cases, $G^1$ and $G^2$ are each independently selected from the group consisting of a terminal group, a π conjugated segment, a linker and a linked specific binding member, wherein at least one of $G^1$ and $G^2$ is a linked specific binding member.

Aspects of the method include assaying the labelling composition contacted sample for the presence of a polymeric dye conjugate-target analyte binding complex to evaluate whether the target analyte is present in the sample. Once the sample has been contacted with the polymeric dye conjugate, any convenient methods may be utilized in assaying the labelling composition contacted sample that is produced for the presence of a polymeric dye conjugate-target analyte binding complex. The polymeric dye conjugate-target analyte binding complex is the binding complex that is produced upon specific binding of the specific binding member of the conjugate to the target analyte, if present. Assaying the labelling composition contacted sample can include detecting a fluorescent signal from the binding complex, if present. In some cases, the assaying includes a separating step where the target analyte, if present, is separated from the sample. A variety of methods can be utilized to separate a target analyte from a sample, e.g., via immobilization on a support. Assay methods of interest include, but are not limited to, any convenient methods and assay formats where pairs of specific binding members such as avidin-biotin or hapten-anti-hapten antibodies find use, are of interest. Methods and assay formats of interest that may be adapted for use with the subject compositions include, but are not limited to, flow cytometry methods, in-situ hybridization methods, enzyme-linked immunosorbent assays (ELISAs), western blot analysis, magnetic cell separation assays and fluorochrome purification chromatography.

In certain embodiments, the method further includes contacting the sample with a second specific binding member that specifically binds the target analyte. In certain instances, the second specific binding member is support bound. Any convenient supports may be utilized to immobilize a component of the subject methods (e.g., a second specific binding member). In certain instances, the support is a particle, such as a magnetic particle. In some instances, the second specific binding member and the polymeric dye conjugate produce a sandwich complex that may be isolated and detected, if present, using any convenient methods. In some embodiments, the method further includes flow cytometrically analyzing the polymeric dye conjugate-target analyte binding complex, i.e., a fluorescently labelled target analyte. Assaying for the presence of a polymeric dye conjugate-target analyte binding complex may provide assay results (e.g., qualitative or quantitative assay data) which can be used to evaluate whether the target analyte is present in the sample.

Any convenient supports may be utilized in the subject methods to immobilize any convenient component of the methods, e.g., labelled specific binding member, target, secondary specific binding member, etc. Supports of interest include, but are not limited to: solid substrates, where the substrate can have a variety of configurations, e.g., a sheet, bead, or other structure, such as a plate with wells; beads, polymers, particle, a fibrous mesh, hydrogels, porous matrix, a pin, a microarray surface, a chromatography support, and the like. In some instances, the support is selected from the group consisting of a particle, a planar solid substrate, a fibrous mesh, a hydrogel, a porous matrix, a pin, a microarray surface and a chromatography support. The support may be incorporated into a system that it provides for cell isolation assisted by any convenient methods, such as a manually-operated syringe, a centrifuge or an automated liquid handling system. In some cases, the support finds use in an automated liquid handling system for the high throughput isolation of cells, such as a flow cytometer.

In some embodiments of the method, the separating step includes applying an external magnetic field to immobilize a magnetic particle. Any convenient magnet may be used as a source of the external magnetic field (e.g., magnetic field gradient). In some cases, the external magnetic field is generated by a magnetic source, e.g. by a permanent magnet or electromagnet. In some cases, immobilizing the magnetic particles means the magnetic particles accumulate near the surface closest to the magnetic field gradient source, i.e. the magnet.

The separating may further include one or more optional washing steps to remove unbound material of the sample from the support. Any convenient washing methods may be used, e.g., washing the immobilized support with a biocompatible buffer which preserves the specific binding interaction of the polymeric dye and the specific binding member. Separation and optional washing of unbound material of the sample from the support provides for an enriched population of target cells where undesired cells and material may be removed.

In certain embodiments, the method further includes detecting the labelled target. Detecting the labelled target may include exciting the multichromophore with one or more lasers and subsequently detecting fluorescence emission from the polymeric tandem dye using one or more optical detectors. Detection of the labelled target can be performed using any convenient instruments and methods, including but not limited to, flow cytometry, FACS systems, fluorescence microscopy; fluorescence, luminescence, ultraviolet, and/or visible light detection using a plate reader; high performance liquid chromatography (HPLC); and mass spectrometry. When using fluorescently labeled components in the methods and compositions of the present disclosure, it is recognized that different types of fluorescence detection systems can be used to practice the subject methods. In some cases, high throughput screening can be performed, e.g., systems that use 96 well or greater microtiter plates. A variety of methods of performing assays on fluorescent materials can be utilized, such as those methods described in, e.g., Lakowicz, J. R., Principles of Fluorescence Spectroscopy, New York: Plenum Press (1983); Herman, B., Resonance energy transfer microscopy, in: Fluorescence Microscopy of Living Cells in Culture, Part B, Methods in Cell Biology, vol. 30, ed. Taylor, D. L. & Wang, Y.-L., San Diego: Academic Press (1989), pp. 219-243; Turro, N.J., Modern Molecular Photochemistry, Menlo Park: Benjamin/Cummings Publishing Col, Inc. (1978), pp. 296-361.

Fluorescence in a sample can be measured using a fluorimeter. In some cases, excitation radiation, from an excitation source having a first wavelength, passes through excitation optics. The excitation optics cause the excitation radiation to excite the sample. In response, fluorescently labelled targets in the sample emit radiation which has a wavelength that is different from the excitation wavelength. Collection optics then collect the emission from the sample. The device can include a temperature controller to maintain the sample at a specific temperature while it is being scanned. In certain instances, a multi-axis translation stage moves a microtiter plate holding a plurality of samples in order to position different wells to be exposed. The multi-axis translation stage, temperature controller, auto-focusing feature, and electronics associated with imaging and data collection can be managed by an appropriately programmed digital computer. The computer also can transform the data collected during the assay into another format for presentation.

In some embodiments, the method of evaluating a sample for the presence of a target analyte further includes detecting fluorescence in a flow cytometer. In some embodiments, the method of evaluating a sample for the presence of a target analyte further includes imaging the labelling composition contacted sample using fluorescence microscopy. Fluorescence microscopy imaging can be used to identify a polymeric dye conjugate-target analyte binding complex in the contacted sample to evaluate whether the target analyte is present. Microscopy methods of interest that find use in the subject methods include laser scanning confocal microscopy.

Also provided are methods of labelled a target molecule. The subject polymeric dyes, find use in a variety of methods of labelling, separation, detection and/or analysis. In some embodiments, the method includes: contacting the target molecule with a polymeric dye (e.g., as described herein) to produce a labelled target molecule, wherein the polymeric dye includes a conjugation tag that covalently links to the target molecule. In some cases, the polymeric dye further includes a signaling chromophore covalently linked to the multichromophore of the polymeric dye in energy-receiving proximity therewith. In some instances of the method, the polymeric dye member includes a multichromophore according to any one of formulae (I)-(VI) (e.g., as described herein), where one of $G^1$ and $G^2$ is a terminal group and the other of $G^1$ and $G^2$ is the conjugation tag.

As used herein the term "conjugation tag" refers to a group that includes a chemoselective functional group (e.g., as described herein) that can covalently link with a compatible functional group of a target molecule, after optional activation and/or deprotection. Any convenient conjugation tags may be utilized in the subject polymeric dyes in order to conjugate the dye to a target molecule of interest. In some embodiments, the conjugation tag includes a terminal functional group selected from an amino, a carboxylic acid or a derivative thereof, a thiol, a hydroxyl, a hydrazine, a hydrazide, a azide, an alkyne and a protein reactive group (e.g. amino-reactive, thiol-reactive, hydroxyl-reactive, imidazolyl-reactive or guanidinyl-reactive).

Any convenient methods and reagent may be adapted for use in the subject labelling methods in order to covalently link the conjugation tag to the target molecule. Methods of interest for labelling a target, include but are not limited to, those methods and reagents described by Hermanson, Bioconjugate Techniques, Third edition, Academic Press, 2013. The contacting step may be performed in an aqueous solution. In some instances, the conjugation tag includes an amino functional group and the target molecule includes an activated ester functional group, such as a NHS ester or sulfo-NHS ester, or vice versa. In certain instances, the conjugation tag includes a maleimide functional group and the target molecule includes a thiol functional group, or vice versa. In certain instances, the conjugation tag includes an alkyne (e.g., a cyclooctyne group) functional group and the target molecule includes an azide functional group, or vice versa, which can be conjugated via Click chemistry.

Any convenient target molecules may be selected for labelling utilizing the subject methods. Target molecules of interest include, but are not limited to, a nucleic acid, such as an RNA, DNA, PNA, CNA, HNA, LNA or ANA molecule, a protein, such as a fusion protein, a modified protein, such as a phosphorylated, glycosylated, ubiquitinated, SUMOylated, or acetylated protein, or an antibody, a peptide, an aggregated biomolecule, a cell, a small molecule, a vitamin and a drug molecule. As used herein, the term "a target protein" refers to all members of the target family, and fragments thereof. The target protein may be any protein of interest, such as a therapeutic or diagnostic target, including but not limited to: hormones, growth factors, receptors, enzymes, cytokines, osteoinductive factors, colony stimulating factors and immunoglobulins. The term "target protein" is intended to include recombinant and synthetic molecules, which can be prepared using any convenient recombinant expression methods or using any convenient synthetic methods, or purchased commercially. In some embodiments, the target molecule is a specific binding member (e.g., as described herein). In certain instances, the specific binding member is an antibody. In some instances, the specific binding member is an antibody fragment or binding derivative thereof. In some case, the antibody fragment or binding derivative thereof is selected from the group consisting of a Fab fragment, a F(ab')$_2$ fragment, a scFv, a diabody and a triabody.

In some cases, the method includes a separating step where the labelled target molecule is separated from the reaction mixture, e.g., excess reagents or unlabeled target. A variety of methods may be utilized to separate a target from a sample, e.g., via immobilization on a support, precipitation, chromatography, and the like.

In some instances, the method further includes detecting and/or analyzing the labelled target molecule. In some instances, the method further includes fluorescently detecting the labelled target molecule. Any convenient methods may be utilized to detect and/or analyze the labelled target molecule in conjunction with the subject methods and compositions. Methods of analyzing a target of interest that find use in the subject methods, include but are not limited to, flow cytometry, fluorescence microscopy, in-situ hybridization, enzyme-linked immunosorbent assays (ELISAs), western blot analysis, magnetic cell separation assays and fluorochrome purification chromatography. Detection methods of interest include but are not limited to fluorescence spectroscopy, fluorescence microscopy, nucleic acid sequencing, fluorescence in-situ hybridization (FISH), protein mass spectroscopy, flow cytometry, and the like.

Detection may be achieved directly via the polymeric dye or polymeric tandem dye, or indirectly by a secondary detection system. The latter may be based on any one or a combination of several different principles including, but not limited to, antibody labelled anti-species antibody and other forms of immunological or non-immunological bridging and signal amplification systems (e.g., biotin-streptavidin technology, protein-A and protein-G mediated technology, or nucleic acid probe/anti-nucleic acid probes, and the like). Suitable reporter molecules may be those known in the field of immunocytochemistry, molecular biology, light, fluorescence, and electron microscopy, cell immunophenotyping, cell sorting, flow cytometry, cell visualization, detection, enumeration, and/or signal output quantification. More than one antibody of specific and/or non-specific nature might be labelled and used simultaneously or sequentially to enhance target detection, identification, and/or analysis.

Systems

Aspects of the invention further include systems for use in practicing the subject methods and compositions. A sample analysis system can include sample field of view or a flow channel loaded with a sample and a labelled specific binding member. In some embodiments, the system is a flow cytometric system including: a flow cytometer including a flow path; a composition in the flow path, wherein the composition includes: a sample; and a labelled specific binding member (e.g., as described herein). In some embodiments, the system for analyzing a sample is a fluorescence microscopy system, including: a fluorescence microscope comprising a sample field of view; and a composition disposed in the sample field of view, wherein the composition comprises a sample; and a labelled specific binding member (e.g., as described herein).

In some instances of the systems, the labelled specific binding member includes: a water solvated light harvesting multichromophore (e.g., as described herein) and a specific binding member that specifically binds a target analyte covalently linked to the multichromophore. In some cases, the labelled specific binding member further comprises a signaling chromophore covalently linked to the multichromophore of the polymeric dye in energy-receiving proximity therewith. In some instances of the subject systems, the labelled specific binding member, the multichromophore is described by any one of formulae (I)-(VI) (e.g., as described herein), wherein: $G^1$ and $G^2$ are each independently selected from the group consisting of a terminal group, a π conjugated segment, a linker and a linked specific binding member, wherein at least one of $G^1$ and $G^2$ is a linked specific binding member.

In certain embodiments of the systems, the composition further includes a second specific binding member that is support bound and specifically binds the target analyte. In some cases, the support includes a magnetic particle. As such, in certain instances, the system may also include a controllable external paramagnetic field configured for application to an assay region of the flow channel.

The sample may include a cell. In some instances, the sample is a cell-containing biological sample. In some instances, the sample includes a labelled specific binding member specifically bound to a target cell. In certain instances, the target analyte that is specifically bound by the specific binding member is a cell surface marker of the cell. In certain cases, the cell surface marker is selected from the group consisting of a cell receptor and a cell surface antigen.

In certain aspects, the system may also include a light source configured to direct light to an assay region of the flow channel or sample field of view. The system may include a detector configured to receive a signal from an assay region of the flow channel or a sample field of view, wherein the signal is provided by the fluorescent composition. Optionally further, the sample analysis system may include one or more additional detectors and/or light sources for the detection of one or more additional signals.

In certain aspects, the system may further include computer-based systems configured to detect the presence of the fluorescent signal. A "computer-based system" refers to the hardware means, software means, and data storage means used to analyze the information of the present invention. The minimum hardware of the computer-based systems of the present invention includes a central processing unit (CPU), input means, output means, and data storage means. A skilled artisan can readily appreciate that any one of the currently available computer-based system are suitable for use in the subject systems. The data storage means may include any manufacture including a recording of the present information as described above, or a memory access means that can access such a manufacture.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g., word processing text file, database format, etc.

A "processor" references any hardware and/or software combination that will perform the functions required of it. For example, any processor herein may be a programmable digital microprocessor such as available in the form of an electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

In addition to the sensor device and signal processing module, e.g., as described above, systems of the invention may include a number of additional components, such as data output devices, e.g., monitors and/or speakers, data input devices, e.g., interface ports, keyboards, etc., fluid handling components, power sources, etc.

In certain aspects, the system includes a flow cytometer. Flow cytometers of interest include, but are not limited to, those devices described in U.S. Pat. Nos. 4,704,891; 4,727,029; 4,745,285; 4,867,908; 5,342,790; 5,620,842; 5,627,037; 5,701,012; 5,895,922; and 6,287,791; the disclosures of which are herein incorporated by reference.

Other systems may find use in practicing the subject methods. In certain aspects, the system may be a fluorimeter or microscope loaded with a sample having a fluorescent composition of any of the embodiments discussed herein. The fluorimeter or microscope may include a light source configured to direct light to the assay region of the flow channel or sample field of view. The fluorimeter or microscope may also include a detector configured to receive a signal from an assay region of the flow channel or field of view, wherein the signal is provided by the fluorescent composition.

Kits

Aspects of the invention further include kits for use in practicing the subject methods and compositions. The compositions of the invention can be included as reagents in kits either as starting materials or provided for use in, for example, the methodologies described above.

A kit can include a polymeric dye including a water solvated light harvesting multichromophore (e.g., as described herein) and a container. Any convenient containers can be utilized, such as tubes, bottles, or wells in a multi-well strip or plate, a box, a bag, an insulated container, and the like. The subject kits can further include one or more components selected from a polymeric tandem dye, a fluorophore, a specific binding member, a specific binding member conjugate, a support bound specific binding member, a cell, a support, a biocompatible aqueous elution buffer, and instructions for use. In some embodiments of the kit, the multichromophore is covalently linked to a specific binding member. In some instances, the specific binding member is an antibody. In certain instances, the specific binding member is an antibody fragment or binding derivative thereof. In certain cases, the antibody fragment or binding derivative thereof is selected from the group consisting of a Fab fragment, a F(ab')2 fragment, a scFv, a diabody and a triabody.

In certain embodiments, the kit finds use in evaluating a sample for the presence of a target analyte, such as an intracellular target. As such, in some instances, the kit includes one or more components suitable for lysing cells. The one or more additional components of the kit may be provided in separate containers (e.g., separate tubes, bottles, or wells in a multi-well strip or plate).

In certain aspects, the kit further includes reagents for performing a flow cytometric assay. Reagents of interest include, but are not limited to, buffers for reconstitution and dilution, buffers for contacting a cell sample the multichromophore, wash buffers, control cells, control beads, fluorescent beads for flow cytometer calibration and combinations thereof. The kit may also include one or more cell fixing reagents such as paraformaldehyde, glutaraldehyde, methanol, acetone, formalin, or any combinations or buffers thereof. Further, the kit may include a cell permeabilizing reagent, such as methanol, acetone or a detergent (e.g., triton, NP-40, saponin, tween 20, digitonin, leucoperm, or any combinations or buffers thereof. Other protein transport inhibitors, cell fixing reagents and cell permeabilizing reagents familiar to the skilled artisan are within the scope of the subject kits.

The compositions of the kit may be provided in a liquid composition, such as any suitable buffer. Alternatively, the compositions of the kit may be provided in a dry composition (e.g., may be lyophilized), and the kit may optionally include one or more buffers for reconstituting the dry composition. In certain aspects, the kit may include aliquots of the compositions provided in separate containers (e.g., separate tubes, bottles, or wells in a multi-well strip or plate).

In addition, one or more components may be combined into a single container, e.g., a glass or plastic vial, tube or bottle. In certain instances, the kit may further include a container (e.g., such as a box, a bag, an insulated container, a bottle, tube, etc.) in which all of the components (and their separate containers) are present. The kit may further include packaging that is separate from or attached to the kit container and upon which is printed information about the kit, the components of the and/or instructions for use of the kit.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, DVD, portable flash drive, etc., on which the information has been recorded. Yet another means that may be present is a website address which may be used via the Internet to access the information at a removed site.

Any convenient means may be present in the kits.

Utility

The polymeric dyes, compositions, methods and systems as described herein may find use in a variety of applications, including diagnostic and research applications, in which the labelling, detection and/or analysis of a target of interest is desirable. The subject polymeric dyes can be used as fluorescent labels in a variety of applications to be utilized with excitation sources from 430 nm to 530 nm. A key laser source used in a variety of biodetection techniques is the Argon (Ar) ion laser used as a continuous wave source of 488 nm light. Because of the early availability of such laser sources, virtually all flow cytometers have a 488 nm source. Thus subject polymeric dyes that excite at 488 nm are of interest and can find use in flow cytometry instrumentation and experimental setups. Additionally, Ar ion lasers have several lines close to 488 nm with significant intensity. Coupled with the availability of a wide range of wavelengths for modern diode lasers and the central location of this range within the UV-visible spectrum, the region from 440 nm to 530 nm is of interest for excitation of the subject polymeric dyes.

Applications of interest include, but are not limited to, methodologies such as cytometry, microscopy, immunoassays (e.g. competitive or non-competitive), assessment of a free analyte, assessment of receptor bound ligand, and so forth. The compositions, system and methods described herein may be useful in analysis of any of a number of samples, including but not limited to, biological fluids, cell culture samples, and tissue samples. In certain aspects, the compositions, system and methods described herein may find use in methods where analytes are detected in a sample, if present, using fluorescent labels, such as in fluorescent activated cell sorting or analysis, immunoassays, immunostaining, and the like. In certain instances, the compositions and methods find use in applications where the evaluation of a sample for the presence of a target analyte is of interest.

In some cases, the methods and compositions find use in any assay format where the detection and/or analysis of a target from a sample is of interest, including but not limited to, flow cytometry, fluorescence microscopy, in-situ hybridization, enzyme-linked immunosorbent assays (ELISAs), western blot analysis, magnetic cell separation assays and fluorochrome purification chromatography. In certain instances, the methods and compositions find use in any application where the fluorescent labelling of a target molecule is of interest. The subject compositions may be adapted for use in any convenient applications where pairs of specific binding members find use, such as biotin-streptavidin and hapten-anti-hapten antibody.

EXAMPLES

Example 1: Synthesis of Conjugated Polymer Via C—H Bond Arylation

Figure 2:
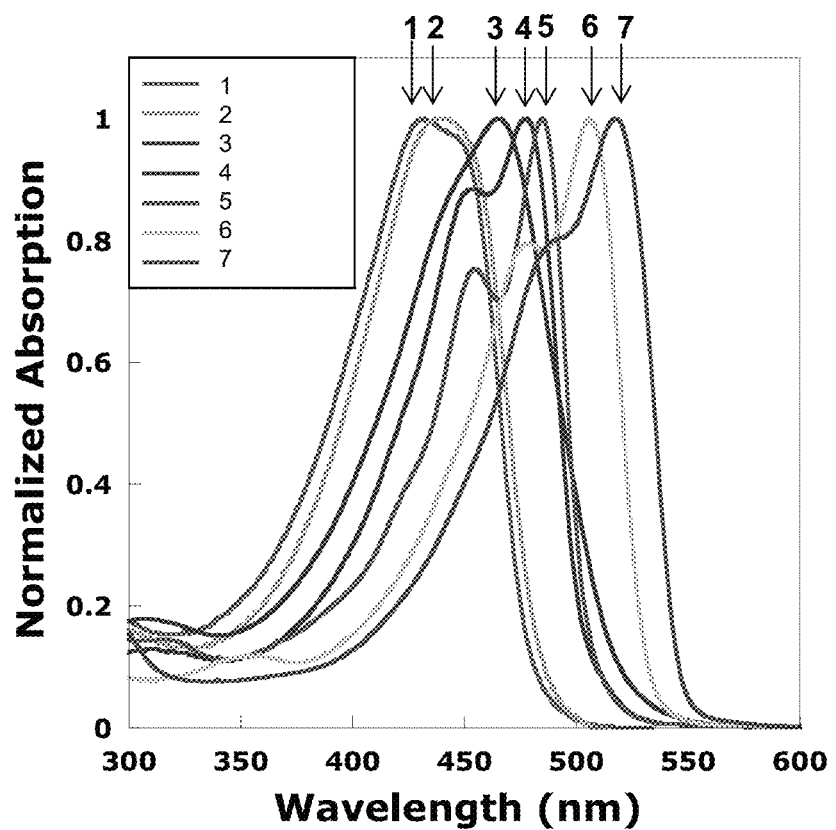
FIG. 2 illustrates the normalized absorption spectra of exemplary dyes 1-7.

The synthesis of the subject dyes can be achieved by a technique called C—H bond arylation (Scheme 1). Other methods such as a Suzuki coupling method (Scheme 2) or a Stille coupling method (Scheme 3) can also be utilized. Unlike Suzuki coupling with involves synthesis of boronic ester/acid monomers, or Stille coupling which involves toxic tin reagents, this method uses simpler monomers and achieves high molecular weights relative to other coupling reactions that can be employed. The absorption profiles of several exemplary dyes (see FIG. 1) that were prepared according to the methods described herein are shown in FIG. 2.

Scheme 1: C-H Bond Arylation method

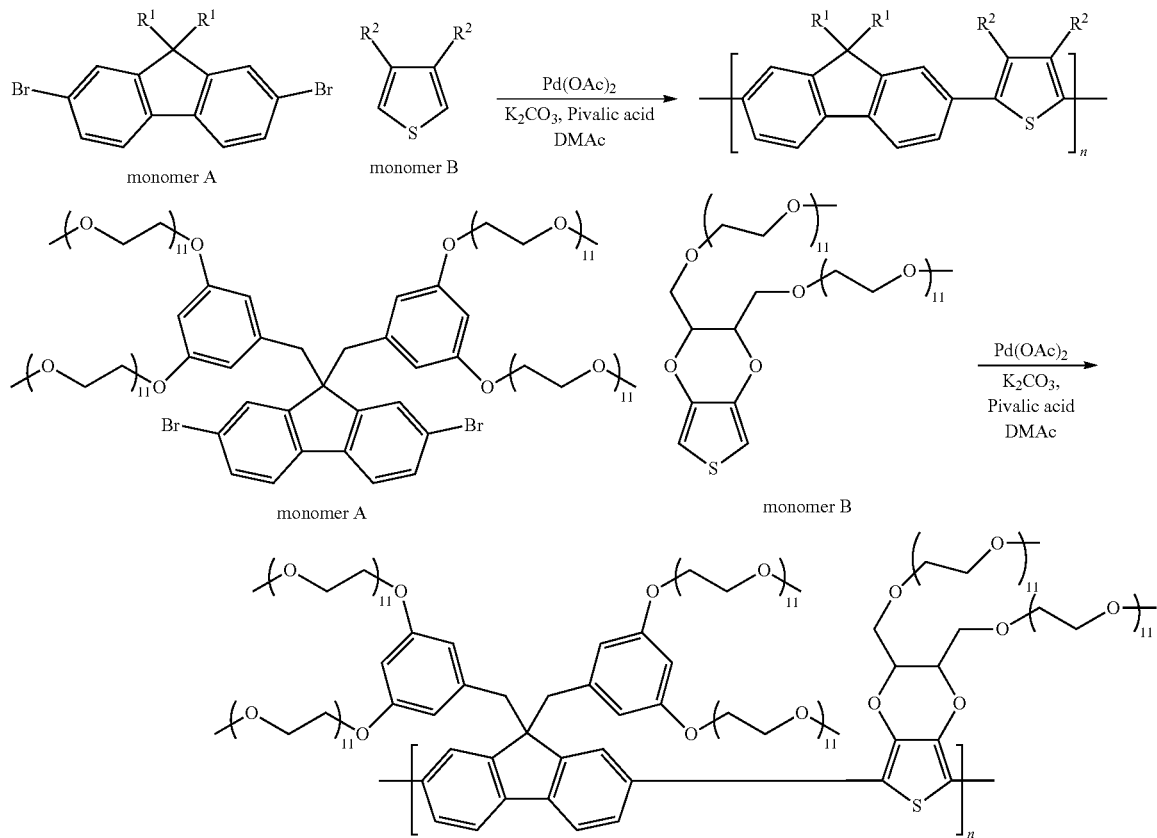

Polymer Synthesis Procedure:

To a single-neck round bottom flask (with a side arm) charged with a Teflon coated stir bar, was added monomer A (446.2 mg, 0.1775 mmol), monomer B (212.9 mg, 0.1775 mmol), potassium carbonate (61.3 mg, 0.444 mmol), Pd(OAc)$_2$ (2.0 mg), pivalic acid (5.4 mg), and dimethylacetamide solvent (1.25 mL). The flask was equipped with a condenser and connected to a Schenk line. The solution was degassed by nitrogen flushing and three freeze-pump-thaw cycles. The mixture was then stirred at 80° C. overnight under to nitrogen protection.

The resulting polymer solution was cooled to room temperature, diluted with 20% EtOH/H$_2$O, and stirred with EDTA (60 mg) at 23° C. for 1 h. The mixture was spin filtered and rinsed with 20% EtOH/H$_2$O. Polymer was collected after vacuum drying (550 mg). Mn=105 kDa; Mw=191 kDa; Absorption $\lambda_{max}$=471 nm; Fluorescence $\lambda_{max}$=516 nm.

Scheme 2: Suzuki Coupling method

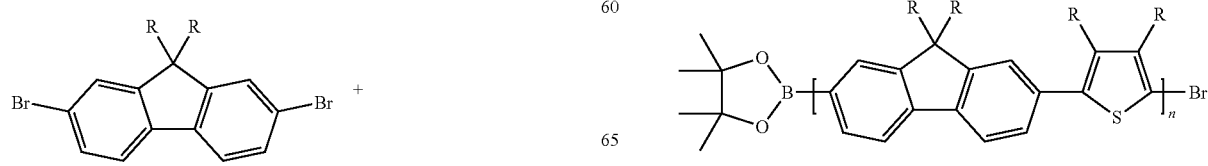

-continued

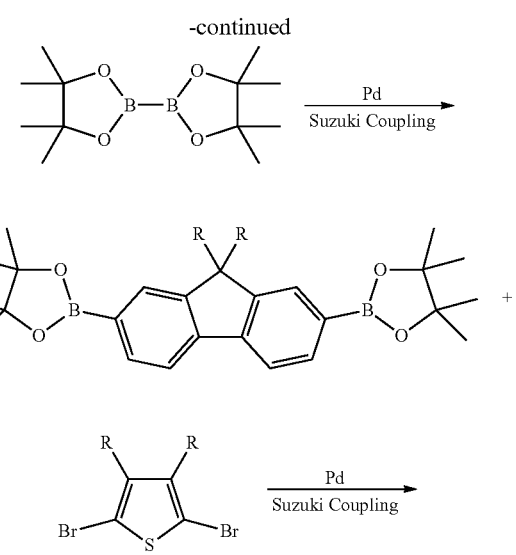

Scheme 3: Stille Coupling method

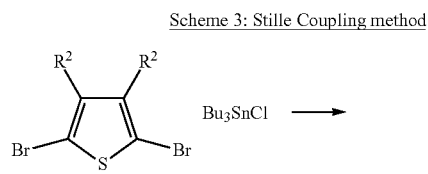

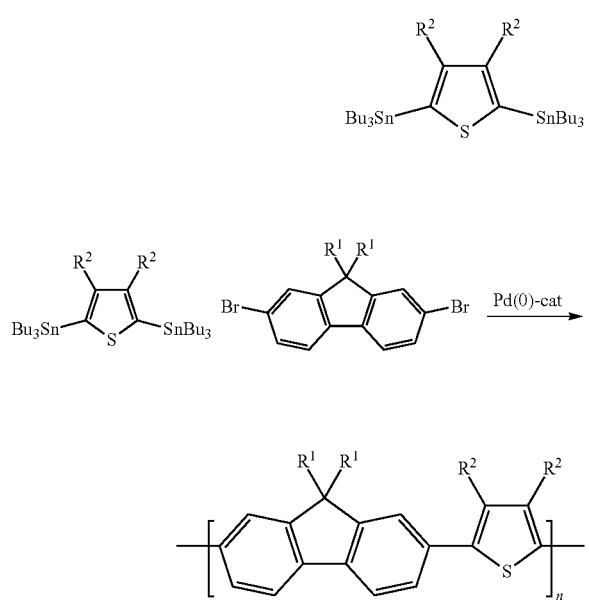

Notwithstanding the appended claims, the disclosure set forth herein is also defined by the following clauses:

Clause 1. A water solvated polymeric dye having a blue excitation spectrum.

Clause 2. The polymeric dye according to clause 1, wherein the polymeric dye comprises a thiophene containing co-monomer.

Clause 3. The polymeric dye according to any one of clauses 1-2, wherein the polymeric dye has no yellow-green absorption at 562 nm.

Clause 4. The polymeric dye according to any one of clauses 1-3, wherein the excitation spectrum of the polymeric dye has a full width at half maximum (FWHM) that is 100 nm or less in width.

Clause 5. The polymeric dye according to any one of clauses 1-4, wherein the polymeric dye has an absorption maximum wavelength of 488 nm±20 nm.

Clause 6. The polymeric dye according to any one of clauses 1-5, wherein the polymeric dye has an extinction coefficient of $1\times10^6$ $M^{-1}$ $cm^{-1}$ or more.

Clause 7. The polymeric dye according to any one of clauses 1-6, wherein the polymeric dye is substituted with non-ionic side groups capable of imparting solubility in water in excess of 10 mg/mL.

Clause 8. The polymeric dye according to any one of clauses 1-7, wherein the polymeric dye comprises a conjugated segment having the structure of formula (I):

(I)

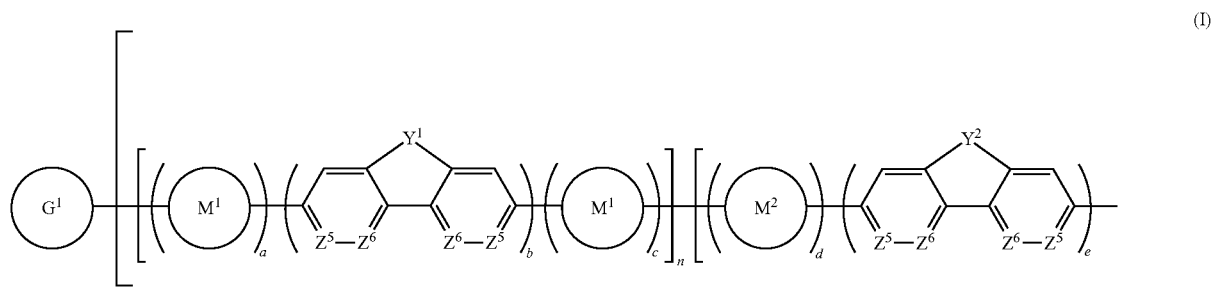

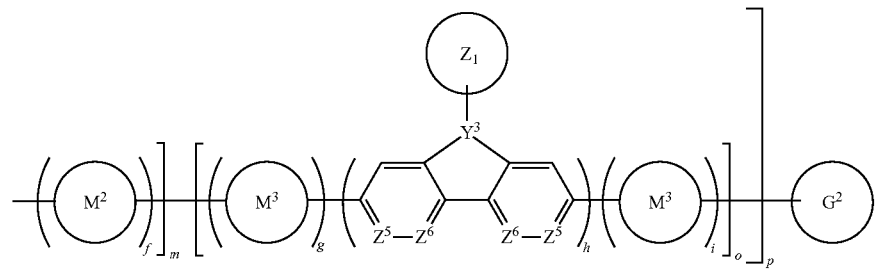

wherein:
- each $M^1$, $M^2$ and $M^3$ is independently an aryl or heterocyclic co-monomer wherein at least one of $M^1$, $M^2$ and $M^3$ is a thiophene containing co-monomer;
- $Z^1$ is a chemoselective functional group or a linked acceptor chromophore;
- $Z^5$ and $Z^6$ are independently CR or N where R is H, halogen, alkoxy, substituted alkoxy, alkyl and substituted alkyl;
- $G^1$ and $G^2$ are each independently selected from a terminal group, a π conjugated segment, a linker and a linked specific binding member;
- $Y^1$, $Y^2$ and $Y^3$ are independently $C(R^3)_2$, $-C(R^3)_2C(R^3)_2-$, $NR^3$, $Si(R^3)_2$ or Se;
- each $R^3$ is independently selected from H, alkyl, substituted alkyl, aryl, substituted aryl, heteroaryl, substituted heteroaryl, acyl, substituted acyl, alkoxy, substituted alkoxy, amido, substituted amido and a WSG (e.g., water soluble group);
- a-i are independently 0 or 1;
- each n, m and o are independently 0 or an integer from 1 to 10,000; and
- p is an integer from 1 to 100,000.

Clause 9. The polymeric dye according to clause 8, wherein $M^1$, $M^2$ and $M^3$ are each independently a thiophene containing co-monomer.

Clause 10. The polymeric dye according to any one of clauses 8-9, wherein:
- a+c≤1;
- d+f≤1;
- g+i≤1;
- b+e+h≥1; and
- n+m+o≥1.

Clause 11. The polymeric dye according to any one of clauses 8-10, wherein the polymeric dye has the structure of one of formula (Ib)-(Ic):

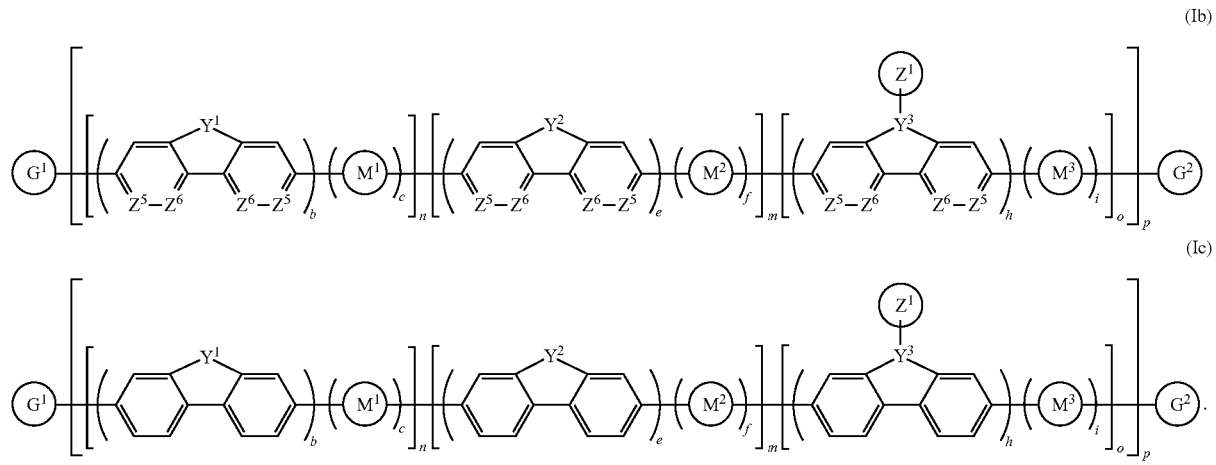

Clause 12. The polymeric dye according to any one of clauses 8-11, wherein the polymeric dye has the structure of one of formula (IIa)-(IIb):

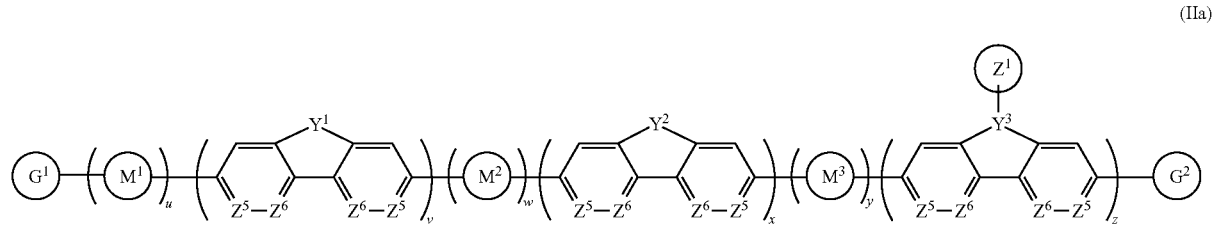

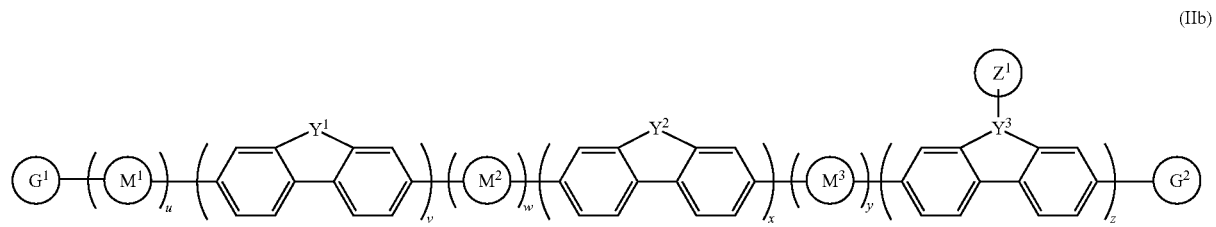

wherein u, v, w, x, y and z represent mol % values for each co-monomer in the multichromophore.

Clause 13. The polymeric dye according to any one of clauses 8-12, wherein the polymeric dye has the structure of one of formula (IIIa)-(IIIb):

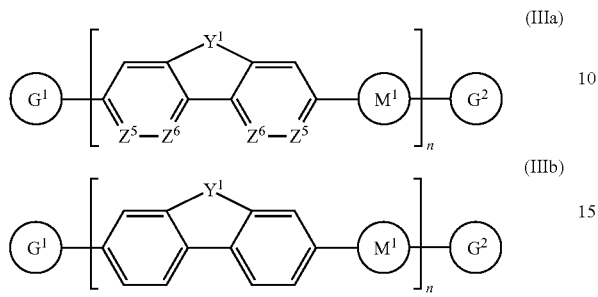

(IIIa)

(IIIb)

wherein n is an integer from 1 to 100,000.

Clause 14. The polymeric dye according to clause 13, wherein $Y^1$ is $C(R^3)_2$.

Clause 15. The polymeric dye according to clause 13, wherein $Y^1$ is $NR^3$.

Clause 16. The polymeric dye according to any one of clauses 8-12, wherein the polymeric dye has the structure of one of formula (IVa)-(IVb):

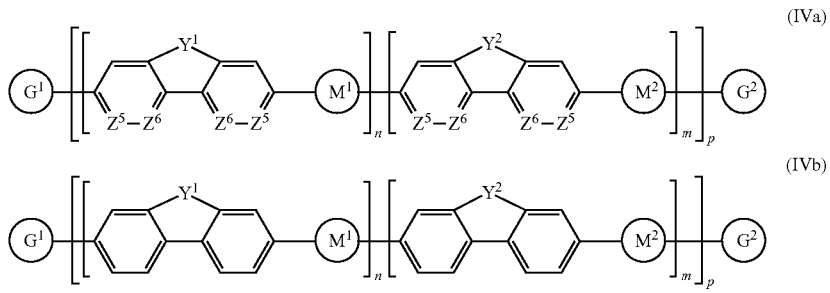

(IVa)

(IVb)

wherein:
  $M^1$ and $M^2$ are each independently a thiophene containing co-monomer;
  each n and m are independently an integer from 1 to 10,000;
  p is an integer from 1 to 100,000.

Clause 17. The polymeric dye according to clause 16, wherein: either
  $Y^1$ is $NR^3$; $Y^2$ is $C(R^3)_2$; and $M^1$ and $M^2$ are the same thiophene containing co-monomer; or
  $Y^1$ is $C(R^3)_2$; $Y^2$ is $NR^3$; and $M^1$ and $M^2$ are the same thiophene containing co-monomer.

Clause 18. The polymeric dye according to clause 16, wherein: $Y^1$ and $Y^2$ are each independently $C(R^3)_2$; and $M^1$ and $M^2$ are the same thiophene containing co-monomer.

Clause 19. The polymeric dye according to clause 8 or 11, wherein the polymeric dye has the structure of one of formula (Va)-(Vb):

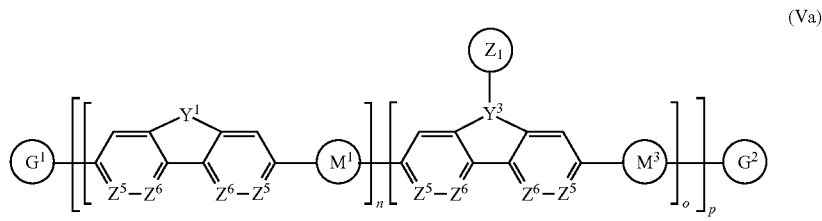

(Va)

(Vb)

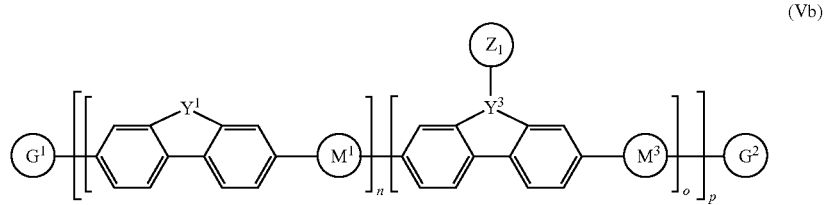

wherein:
$M^1$ and $M^3$ are each independently a thiophene containing co-monomer;
each n and each o are independently an integer from 1 to 10,000; and
p is an integer from 1 to 100,000.

Clause 20. The polymeric dye according to clause 19, wherein $Y^3$—$Z^1$ is $C(R^3)(T^1$-$Z^1)$, wherein $Z^1$ is a linked signaling chromophore and $T^1$ is a linker.

Clause 21. The polymeric dye according to clause 19, wherein $Y^3$—$Z^1$ is N-$T^1$-$Z^1$, wherein $Z^1$ is a linked signaling chromophore and $T^1$ is a linker.

Clause 22. The polymeric dye according to any one of clauses 19-21, wherein: $Y^1$ is $NR^3$; and $M^1$ and $M^3$ are the same thiophene containing co-monomer.

Clause 23. The polymeric dye according to any one of clauses 19-21, wherein: $Y^1$ is $C(R^3)_2$; and $M^1$ and $M^3$ are the same thiophene containing co-monomer.

Clause 24. The polymeric dye according to clause 8 or 11, wherein the polymeric dye has the structure of one of formula (VIa)-(VIb):

(VIa)

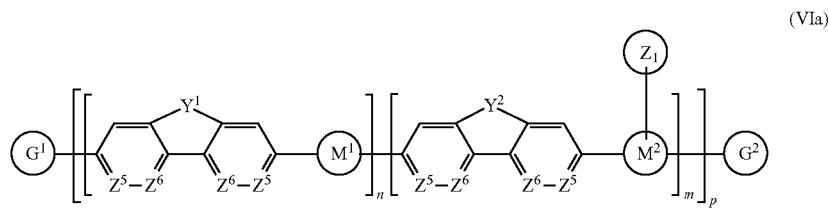

(VIb)

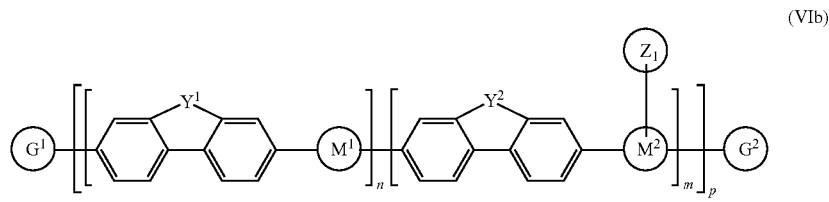

wherein:

M¹ and M² are each independently a thiophene containing co-monomer;

each n and each m are independently an integer from 1 to 10,000;

$Z^1$ is a linked chemoselective functional group or a linked signaling chromophore;

and p is an integer from 1 to 100,000.

Clause 25. The polymeric dye according to clause 24, wherein $Y^1$ and $Y^2$ are $NR^3$.

Clause 26. The polymeric dye according to clause 24, wherein $Y^1$ and $Y^2$ are $C(R^3)_2$.

Clause 27. The polymeric dye according to clause 24, wherein either $Y^1$ is $NR^3$ and $Y^2$ is $C(R^3)_2$, or $Y^1$ is $C(R^3)_2$ and $Y^2$ is $NR^3$.

Clause 28. The polymeric dye according to any one of clauses 2-27, wherein the thiophene-containing co-monomer is described by formula (VII), (VIII) or (IX):

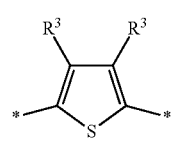

(VII)

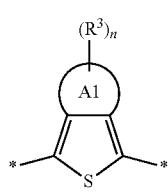

(VIII)

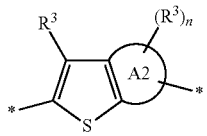

(IX)

wherein:

A1 and A2 are each a fused monocyclic or bicyclic group each $R^3$ is independently selected from H, amino, substituted amino, halogen, cyano, alkyl, substituted alkyl, aryl, substituted aryl, heteroaryl, substituted heteroaryl, acyl, substituted acyl, amido, substituted amido, sulfonic acid, cyano, alkoxy, substituted alkoxy, WSG and -T²-Z², wherein $Z^2$ is a chemoselective functional group or a linked signaling chromophore, and $T^2$ is a linker;

n is 0, 1, 2, 3 or 4; and each * is a site for covalent attachment to the unsaturated backbone of a conjugated polymer.

Clause 29. The polymeric dye according to clause 28, wherein A1 and A2 are selected from a fused monocyclic heterocycle, a fused monocyclic heteroaryl and a fused bicyclic heteroaryl.

Clause 30. The polymeric dye according to any one of clauses 28-29, wherein the thiophene-containing co-monomer is described by one of formula (X)-(XVII):

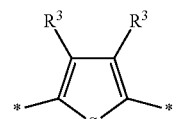

(X)

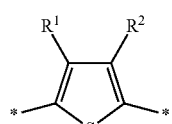

(XI)

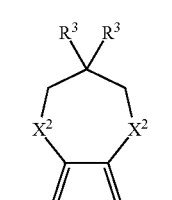

(XII)

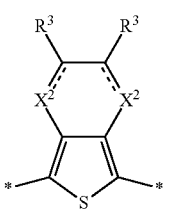

(XIII)

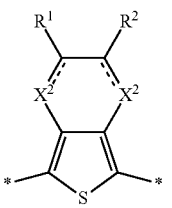

(XIV)

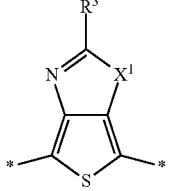

(XV)

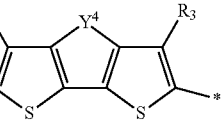

(XVI)

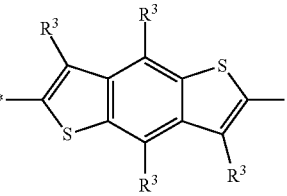

(XVII)

wherein:

$X^1$ is $CR^3$, $NR^3$, O or S;

$X^2$ is N, O or S, wherein when $X^2$ is N, each ==== is a double bond and when $X^2$ is O or S, each ==== is a single bond;

R[1] and R[2] together form a 5- or 6-membered fused aryl or heteroaryl ring which is optionally substituted with one or more R[3] groups; and
Y[4] is NR[3], C(R[3])$_2$ or Si(R[3])$_2$.
Clause 31. The polymeric dye according to clause 30, wherein the thiophene-containing co-monomer is described by one of the following structures (a) to (q):
(a)
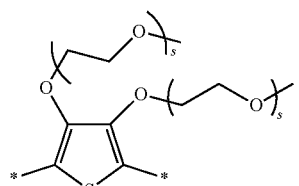
(b)
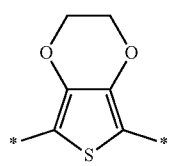
(c)
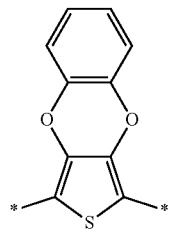
(d)
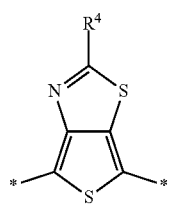
(e)
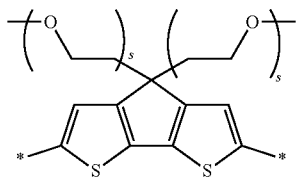
(f)
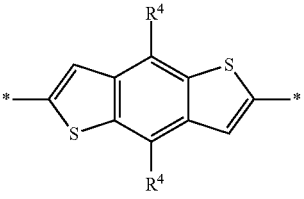
(g)
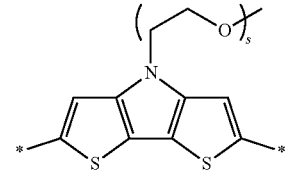
-continued
(h)
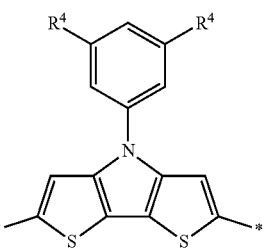
(i)
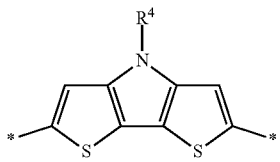
(j)
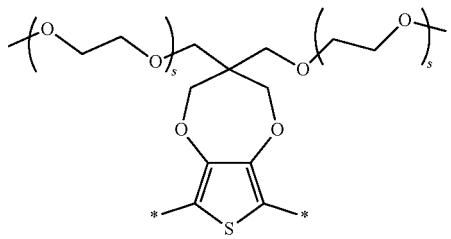
(k)
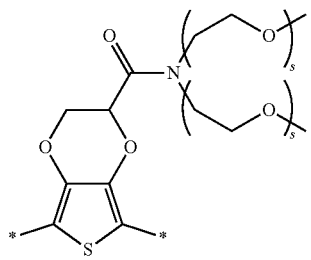
(l)
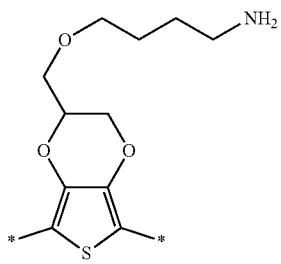
(m)
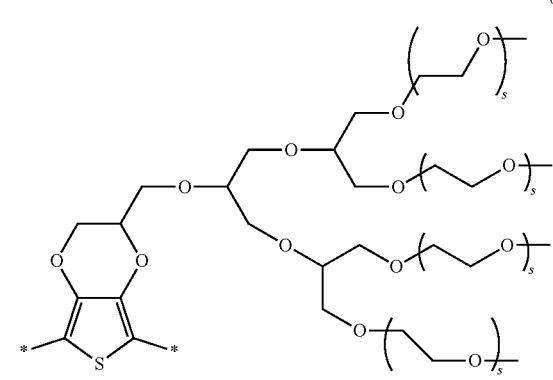

-continued (n)
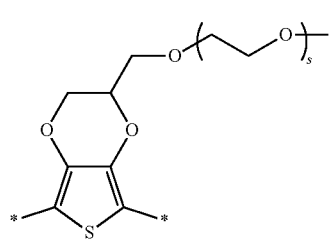

(o)
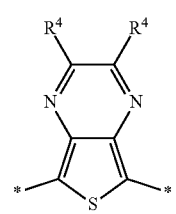

(p)
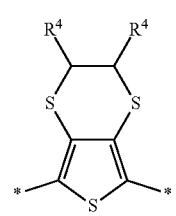

(q)
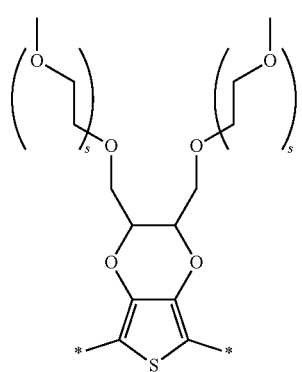

wherein:
  each $R^4$ is independently selected from H, amino, substituted amino, halogen, cyano, alkyl, substituted alkyl, aryl, substituted aryl, heteroaryl, substituted heteroaryl, acyl, substituted acyl, amido, substituted amido, sulfonic acid, cyano, alkoxy, substituted alkoxy and $-T^2-Z^2$, wherein $Z^2$ is a chemoselective functional group or a linked acceptor chromophore, and $T^2$ is a linker; and
  each s is 0 or an integer from 1 to 50.

Clause 32. The polymeric dye according to any one of clauses 8-31, wherein each $R^3$ and each $R^4$ is independently selected from H, substituted aryl, alkyl and the following structures:

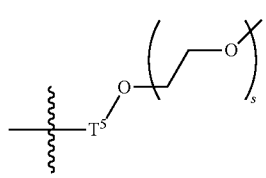

-continued

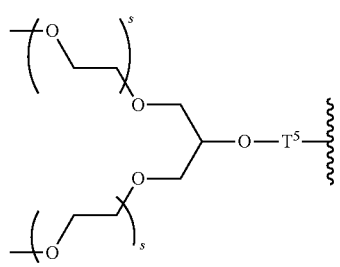

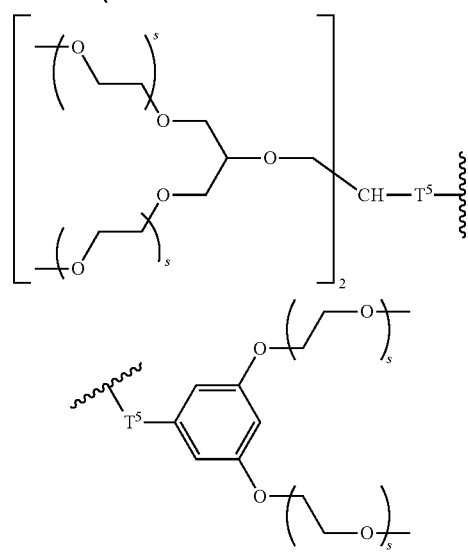

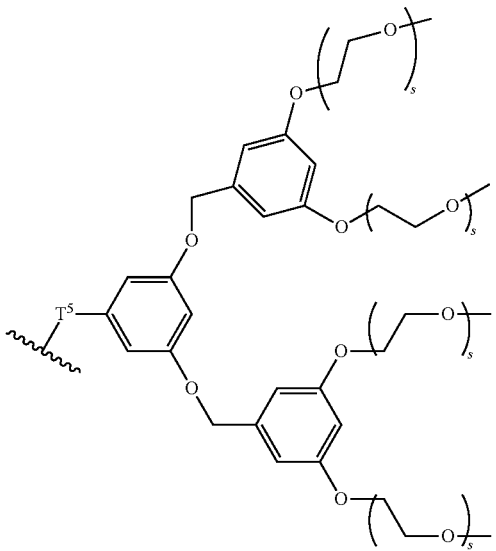

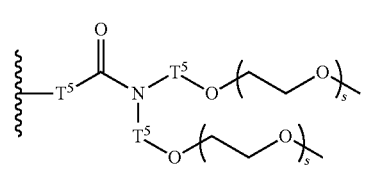

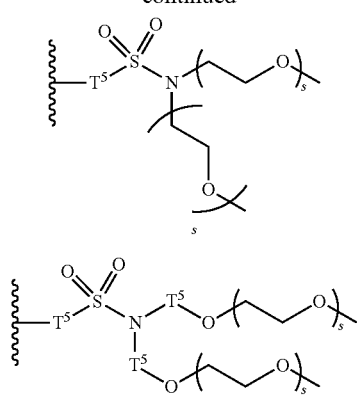
wherein: each $T^5$ is independently an optional linker; and each s is 0 or an integer from 1 to 50.
Clause 33. The polymeric dye according to any one of clauses 28-32, wherein the thiophene-containing co-monomer is described by one of the following structures (ba) to (bu):
(ba)
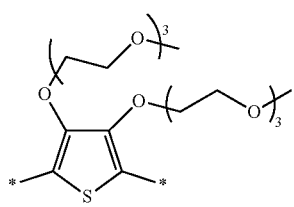
(bb)
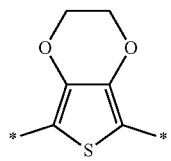
(bc)
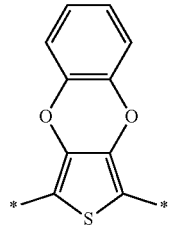
(bd)
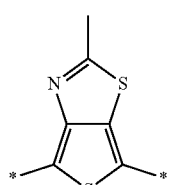
(be)
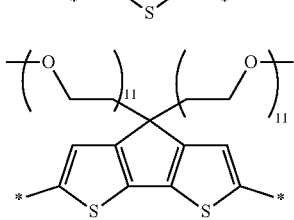
(bf)
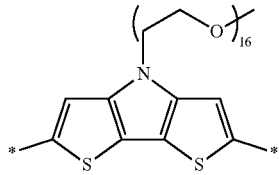
(bg)
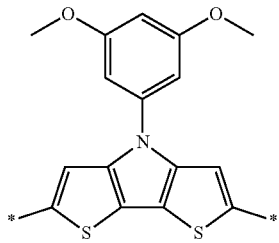
(bh)
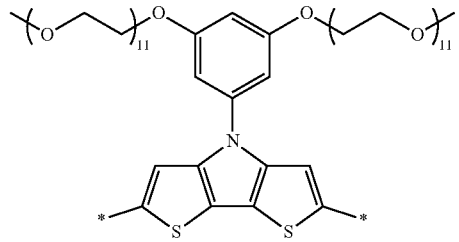
(bi)
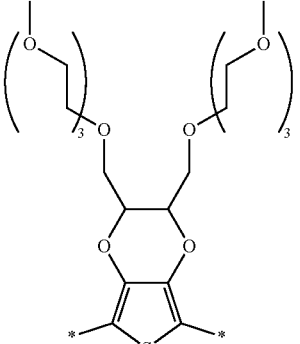
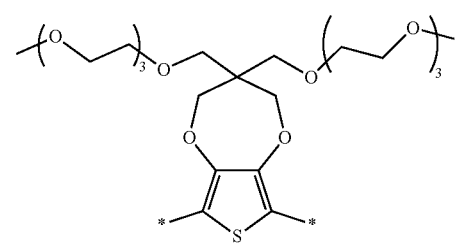
(bk)
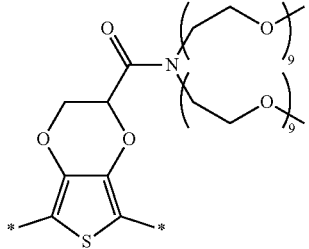

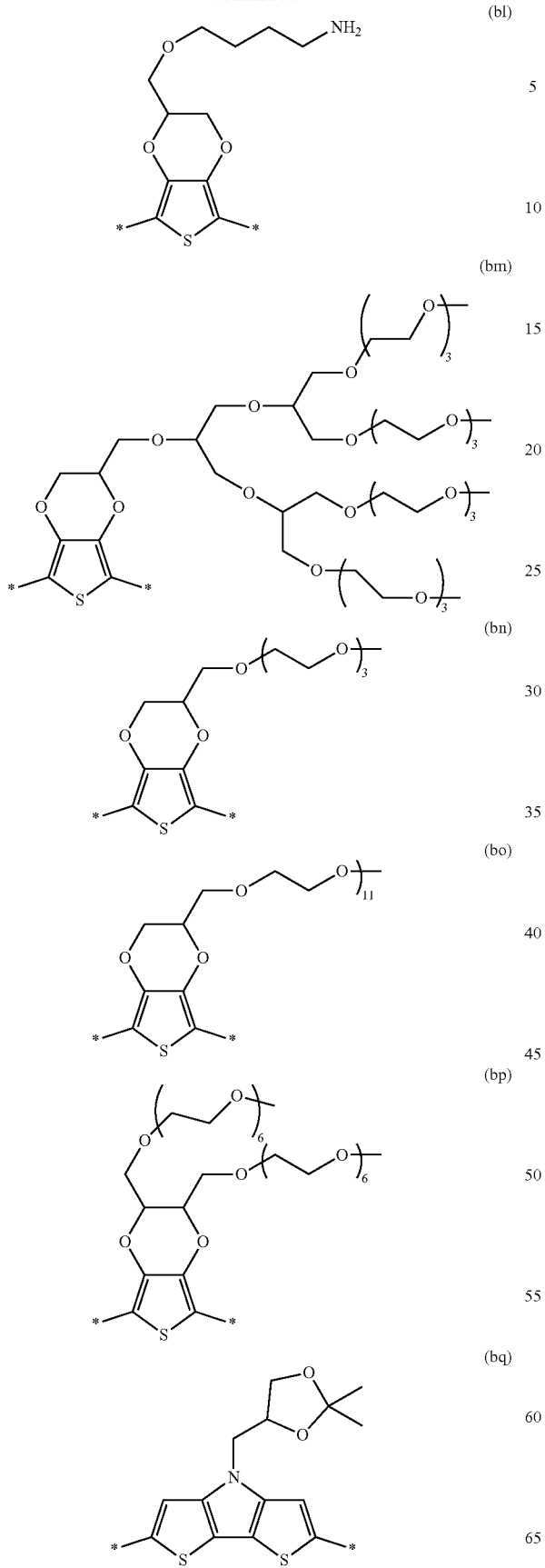

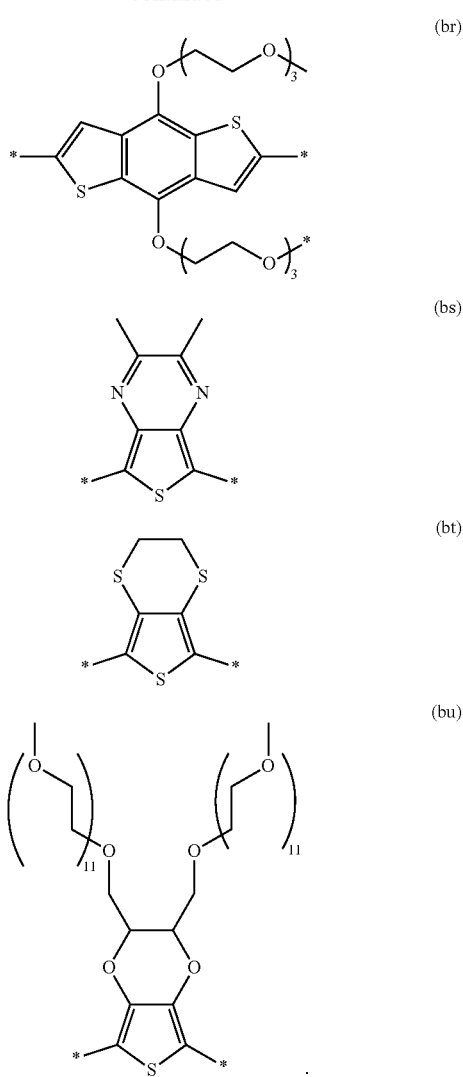

Clause 34. The polymeric dye according to any one of clauses 8-33, wherein the polymeric dye comprises a co-monomer linked to a signaling chromophore having the structure of formula (XVI):

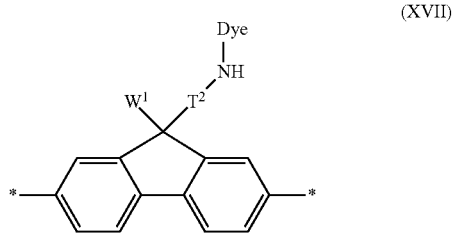

wherein: W is an alkyl, a substituted alkyl or a WSG; and Dye is a signaling chromophore.

Clause 35. The polymeric dye according to clause 34, wherein the polymeric dye comprises a co-monomer linked to a signaling chromophore having one of the following structures:

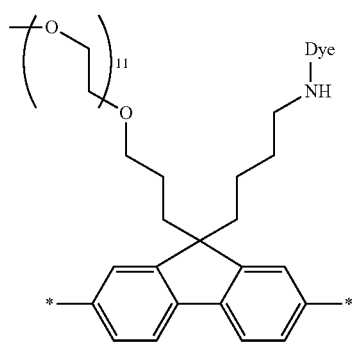

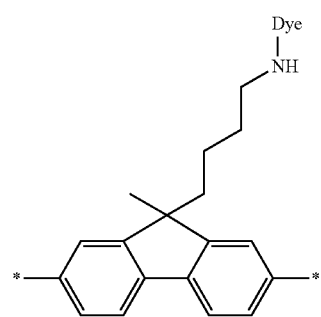

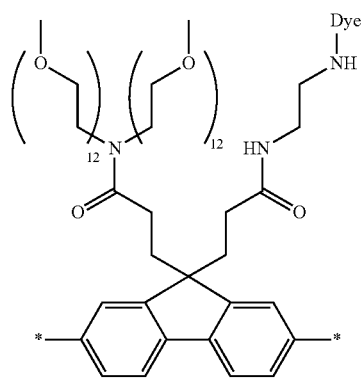

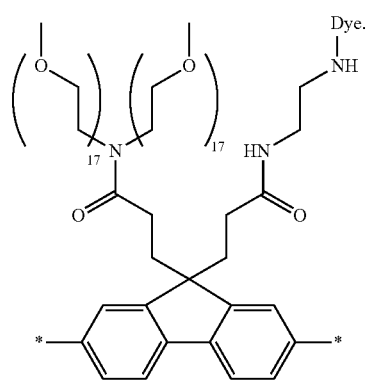

Clause 36. The polymeric dye according to any one of clauses 8-30, wherein co-monomers $M^1$-$M^3$ are independently selected from formulae (XVIII) and (XIX):

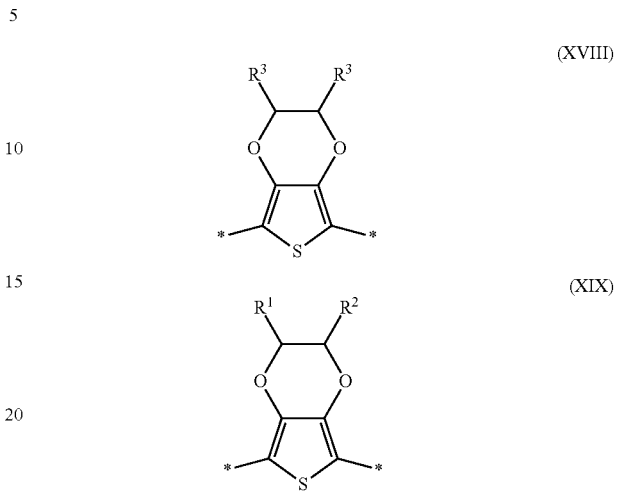

wherein:

$R^1$ and $R^2$ together form a 5- or 6-membered fused aryl or heteroaryl ring which is optionally substituted with one or more $R^3$ groups; and each $R^3$ is independently selected from H, amino, substituted amino, halogen, cyano, alkyl, substituted alkyl, aryl, substituted aryl, heteroaryl, substituted heteroaryl, acyl, substituted acyl, amido, substituted amido, sulfonic acid, cyano, alkoxy, substituted alkoxy and -$T^2$-$Z^2$, wherein $Z^2$ is a chemoselective functional group or a linked acceptor chromophore, and $T^2$ is a linker.

Clause 37. The polymeric dye according to any one of clauses 8-30, wherein co-monomers $M^1$-$M^3$ are independently selected from formulae (e)-(i):

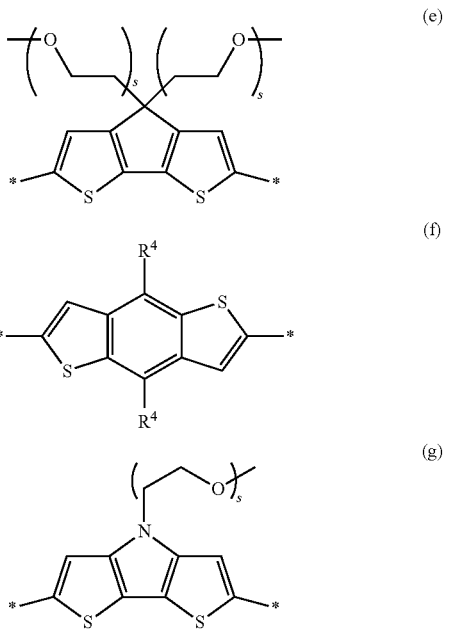

-continued

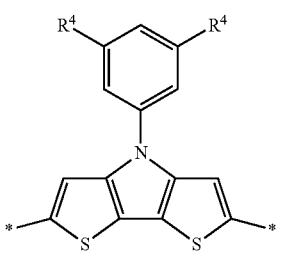
(h)

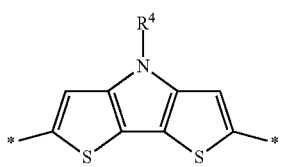
(i)

wherein:
  each R⁴ is independently selected from H, amino, substituted amino, halogen, cyano, alkyl, substituted alkyl, aryl, substituted aryl, heteroaryl, substituted heteroaryl, acyl, substituted acyl, amido, substituted amido, sulfonic acid, cyano, alkoxy, substituted alkoxy and -T²-Z², wherein Z² is a chemoselective functional group or a linked acceptor chromophore, and T² is a linker; and
  each s is 0 or an integer from 1 to 50.

Clause 38. The polymeric dye according to any one of clauses 36-37, wherein each R³ and each R⁴ is independently selected from H, substituted aryl, alkyl and the following structures:

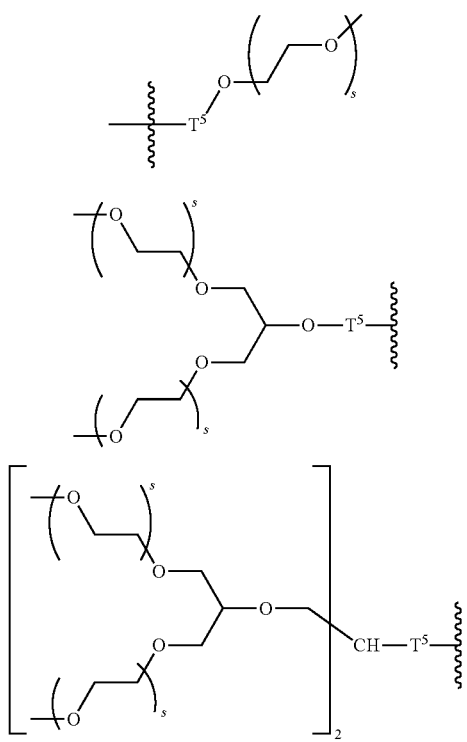

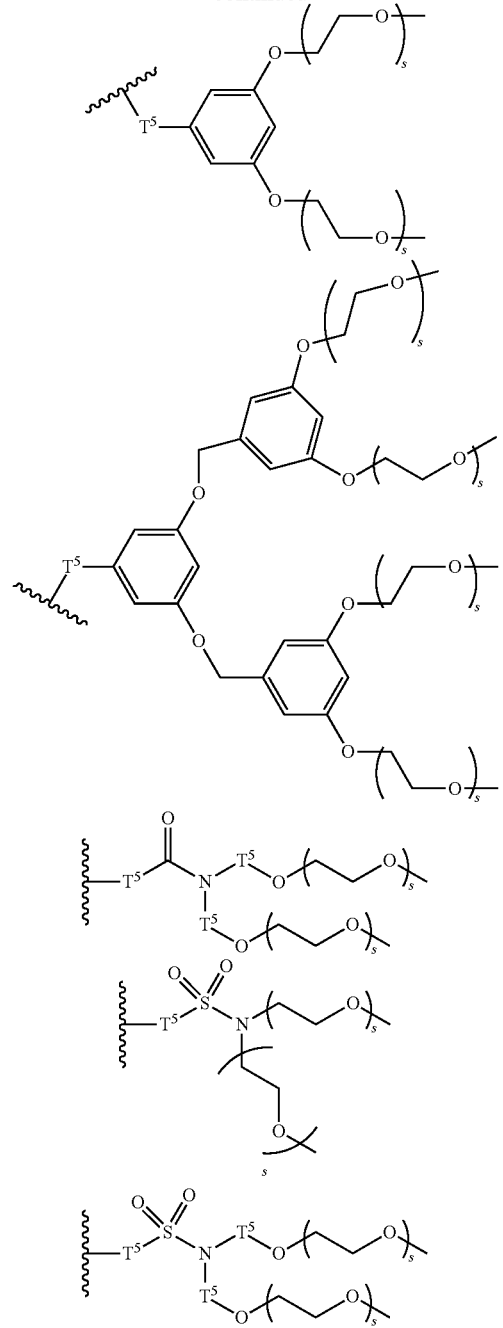

wherein:
  each T⁵ is independently an optional linker; and
  each s is 0 or an integer from 1 to 50.

Clause 39. A polymeric tandem dye comprising:
  a polymeric dye having a blue excitation spectrum according to any one of clauses 1-38; and
  a signaling chromophore covalently linked to the polymeric dye in energy-receiving proximity therewith.

Clause 40. The polymeric tandem dye according to clause 39, wherein the polymeric dye comprises a thiophene containing co-monomer.

Clause 41. The polymeric tandem dye according to clause 39, wherein the polymeric dye has an absorption maximum wavelength from 440 nm to 530 nm.

Clause 42. The polymeric tandem dye according to clause 39, wherein the signaling chromophore emission has a quantum yield of 0.1 or more.

Clause 43. The polymeric tandem dye according to clause 39, wherein the polymeric dye has an extinction coefficient of $1\times10^6$ $M^{-1}$ $cm^{-1}$ or more.

Clause 44. The polymeric tandem dye according to any one of clauses 39-43, wherein the multichromophore is substituted with non-ionic side groups capable of imparting solubility in water in excess of 10 mg/mL.

Clause 45. The polymeric tandem dye according to any one of clauses 39-44, wherein the signaling chromophore is a fluorophore.

Clause 46. The polymeric tandem dye according to any one of clauses 39-44, wherein the signaling chromophore is a quencher.

Clause 47. The polymeric tandem dye according to any one of clauses 39-46, wherein the signaling chromophore is selected from a rhodamine, a coumarin, a xanthene, a cyanine, a polymethine, a pyrene, a dipyrromethene borondifluoride, a napthalimide, a phycobiliprotein, a peridinum chlorophyll protein, conjugates thereof, and combinations thereof.

Clause 48. The polymeric tandem dye according to any one of clauses 39-45 and 47, wherein the signaling chromophore is selected from fluorescein, 6-FAM, rhodamine, Texas Red, California Red, iFluor594, tetramethylrhodamine, a carboxyrhodamine, carboxyrhodamine 6G, carboxyrhodol, carboxyrhodamine 110, Cascade Blue, Cascade Yellow, coumarin, Cy2®, Cy3®, Cy3.5®, Cy5®, Cy5.5®, Cy7®, Cy-Chrome, DyLight 350, DyLight 405, DyLight 488, DyLight 549, DyLight 594, DyLight 633, DyLight 649, DyLight 680, DyLight 750, DyLight 800, phycoerythrin, PerCP (peridinin chlorophyll-a Protein), PerCP-Cy5.5, JOE (6-carboxy-4',5'-dichloro-2',7'-dimethoxyfluorescein), NED, ROX (5-(and -6)-carboxy-X-rhodamine), HEX, Lucifer Yellow, Marina Blue, Oregon Green 488, Oregon Green 500, Oregon Green 514, Alexa Fluor® 350, Alexa Fluor® 430, Alexa Fluor® 488, Alexa Fluor® 532, Alexa Fluor® 546, Alexa Fluor® 568, Alexa Fluor® 594, Alexa Fluor® 633, Alexa Fluor® 647, Alexa Fluor® 660, Alexa Fluor® 680, 7-amino-4-methylcoumarin-3-acetic acid, BODIPY® FL, BODIPY® FL-Br2, BODIPY® 530/550, BODIPY® 558/568, BODIPY® 564/570, BODIPY® 576/589, BODIPY® 581/591, BODIPY® 630/650, BODIPY® 650/665, BODIPY® R6G, BODIPY® TMR, BODIPY® TR, conjugates thereof and combinations thereof.

Clause 49. The polymeric tandem dye according to any one of clauses 39 to 49, wherein:
the signaling chromophore is linked to a co-monomer comprising 1% to 20% by molarity of the multichromophore; and
the polymeric dye is a conjugated polymer comprising 5 or more repeat units.

Clause 50. The polymeric tandem dye according to any one of clauses 39 to 45 and 47-49, wherein the signaling chromophore emission is 1.5-fold greater or more when excited by the polymeric dye as compared to direct excitation of the acceptor chromophore with incident light.

Clause 51. The polymeric tandem dye according to any one of clauses 39-50, wherein the polymeric dye comprises a terminal group -$L^3$-Z where $L^3$ is a linker and Z is a specific binding member.

Clause 52. The polymeric tandem dye according to clause 51, wherein the linker is selected from the group consisting of an alkyl, a substituted alkyl, an alkyl-amido, an alkyl-amido-alkyl and a PEG moiety.

Clause 53. The polymeric tandem dye according to clause 51, wherein -$L^3$-Z is described by the following structure:

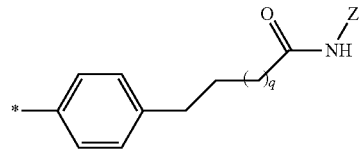

wherein: q is 0 or an integer from 1-12; and Z is the specific binding member.

Clause 54. The polymeric tandem dye according to any one of clauses 51-53, wherein Z is a biomolecule.

Clause 55. The polymeric tandem dye according to any one of clauses 51-54, wherein Z is an antibody.

Clause 56. The polymeric tandem dye according to any one of clauses 51-54, wherein Z is an antibody fragment or binding derivative thereof.

Clause 57. The polymeric tandem dye according to clause 56, wherein the antibody fragment or binding derivative thereof is selected from the group consisting of a Fab fragment, a $F(ab')_2$ fragment, a scFv, a diabody and a triabody.

Clause 58. A labelled specific binding member, comprising:
a polymeric dye having a blue excitation spectrum according to any one of clauses 1-38; and
a specific binding member covalently linked to the polymeric dye.

Clause 59. The labelled specific binding member according to clause 58, wherein the polymeric dye comprises a thiophene containing co-monomer.

Clause 60. The labelled specific binding member according to any one of clauses 58-59, wherein the polymeric dye comprises a signaling chromophore covalently linked to the polymeric dye in energy-receiving proximity therewith.

Clause 61. The labelled specific binding member according to any one of clauses 59-60, wherein the specific binding member is an antibody.

Clause 62. The labelled specific binding member according to any one of clauses 59-60, wherein the specific binding member is an antibody fragment or binding derivative thereof.

Clause 63. The labelled specific binding member according to clause 62, wherein the antibody fragment or binding derivative thereof is selected from the group consisting of a Fab fragment, a $F(ab')_2$ fragment, a scFv, a diabody and a triabody.

Clause 64. The labelled specific binding member according to clause 60, wherein the signaling chromophore is selected from a rhodamine, a coumarin, a xanthene, a cyanine, a polymethine, a pyrene, a dipyrromethene borondifluoride, a napthalimide, a phycobiliprotein, a peridinum chlorophyll protein, conjugates thereof, and combinations thereof.

Clause 65. A method of evaluating a sample for the presence of a target analyte, the method comprising:
(a) contacting the sample with a polymeric dye conjugate that specifically binds the target analyte to produce a labelling composition contacted sample, wherein the polymeric dye conjugate comprises:
(i) a polymeric dye having a blue excitation spectrum according to any one of clauses 1-38; and
(ii) a specific binding member covalently linked to the polymeric dye; and (b) assaying the labelling composition contacted sample for the presence of a polymeric dye conjugate-target analyte binding complex to evaluate whether the target analyte is present in the sample.

Clause 66. The method according to clause 65, wherein the polymeric dye comprises a thiophene containing co-monomer.

Clause 67. The method according to any one of clauses 65-66, wherein the polymeric dye comprises a signaling chromophore covalently linked to the multichromophore in energy-receiving proximity therewith.

Clause 68. The method according to any one of clauses 65-67, further comprising contacting the sample with a second specific binding member that is support bound and specifically binds the target analyte.

Clause 69. The method according to clause 68, wherein the support comprises a magnetic particle.

Clause 70. The method according to any one of clauses 65-69, wherein the target analyte is associated with a cell.

Clause 71. The method according to clause 70, wherein the target analyte is a cell surface marker of the cell.

Clause 72. The method according to clause 71, wherein the cell surface marker is selected from the group consisting of a cell receptor and a cell surface antigen.

Clause 73. The method according to clause 70, wherein the target analyte is an intracellular target, and the method further comprises lysing the cell.

Clause 74. The method according to any one of clauses 65-73, wherein the method further comprises flow cytometrically analyzing the fluorescently labelled target analyte.

Clause 75. A method of labelling a target molecule, the method comprising: contacting the target molecule with a polymeric dye to produce a labelled target molecule, wherein the polymeric dye has a blue excitation spectrum and comprises a conjugation tag that covalently links to the target molecule.

Clause 76. The method according to clause 75, wherein the polymeric dye comprises a thiophene containing co-monomer.

Clause 77. The method according to any one of clauses 75-76, wherein the polymeric dye comprises a signaling chromophore covalently linked to the polymeric dye in energy-receiving proximity therewith.

Clause 78. The method according to any one of clauses 75-77, further comprising fluorescently detecting the labelled target molecule.

Clause 79. The method according to any one of clauses 75-78, wherein the conjugation tag comprises a terminal functional group selected from an amino, a thiol, a hydroxyl, a hydrazine, a hydrazide, an azide, an alkyne, maleimide, iodoacetyl, amine, an active ester and a protein reactive group.

Clause 80. The method according to any one of clauses 75-79, wherein the target molecule is a specific binding member.

Clause 81. The method according to clause 80, wherein the specific binding member is an antibody.

Clause 82. The method according to clause 80, wherein the specific binding member is an antibody fragment or binding derivative thereof.

Clause 83. The method according to clause 82, wherein the antibody fragment or binding derivative thereof is selected from the group consisting of a Fab fragment, a F(ab')$_2$ fragment, a scFv, a diabody and a triabody.

Clause 84. A flow cytometric system, comprising:
a flow cytometer comprising a flow path;
a composition in the flow path, wherein the composition comprises:
a sample; and
a labelled specific binding member comprising:
a polymeric dye having a blue excitation spectrum according to any one of clauses 1-38; and
a specific binding member that specifically binds a target analyte and is covalently linked to the polymeric dye.

Clause 85. The system according to clause 84, wherein the polymeric dye comprises a thiophene containing co-monomer.

Clause 86. The system according to any one of clauses 84-85, wherein the labelled specific binding member further comprises a signaling chromophore covalently linked to the polymeric dye in energy-receiving proximity therewith.

Clause 87. The system according to any one of clauses 84-86, wherein the composition further comprises a second specific binding member that is support bound and specifically binds the target analyte.

Clause 88. The system according to clause 85, wherein the support comprises a magnetic particle.

Clause 89. The system according to any one of clauses 84-88, wherein the sample comprises a cell.

Clause 90. The system according to clause 89, wherein the target analyte is a cell surface marker of the cell.

Clause 91. The system according to clause 90, wherein the cell surface marker is selected from the group consisting of a cell receptor and a cell surface antigen.

Clause 92. A kit comprising: a polymeric dye having a blue excitation spectrum; and a container.

Clause 93. The kit according to clause 92, wherein the polymeric dye comprises a thiophene containing co-monomer.

Clause 94. The kit according to any one of clauses 92-93, further comprising one or more components selected from the group consisting of a polymeric tandem dye, a fluorophore, a specific binding member, a specific binding member conjugate, a cell, a support, a biocompatible aqueous elution buffer and instructions for use.

Clause 95. The kit according to any one of clauses 92-94, wherein the polymeric dye is described by any one of clauses 2-53.

Clause 96. The kit according to any one of clauses 92-95, wherein the polymeric dye is covalently linked to a specific binding member.

Clause 97. The kit according to clause 96, wherein the specific binding member is an antibody.

Clause 98. The kit according to clause 96, wherein the specific binding member is an antibody fragment or binding derivative thereof.

Clause 99. The kit according to clause 98, wherein the antibody fragment or binding derivative thereof is selected from the group consisting of a Fab fragment, a F(ab')$_2$ fragment, a scFv, a diabody and a triabody.

Clause 100. The kit according to any one of clauses 92-99, wherein polymeric dye further comprises an acceptor signaling chromophore covalently linked to the polymeric due in energy-receiving proximity therewith.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the following.

What is claimed is:

1. A method of evaluating a sample for the presence of a target analyte, the method comprising:
   (a) contacting the sample with a polymeric dye conjugate that specifically binds the target analyte to produce a labelling composition contacted sample, wherein the polymeric dye conjugate comprises:
      (i) a polymeric dye comprising a thiophene-containing co-monomer; and
      (ii) a specific binding member covalently linked to the polymeric dye; and
   (b) assaying the labelling composition contacted sample for the presence of a polymeric dye conjugate-target analyte binding complex to evaluate whether the target analyte is present in the sample, wherein the assaying comprises contacting the labelling composition contacted sample with excitation radiation with a blue wavelength.

2. The method according to claim 1, wherein the polymeric dye comprises a signaling chromophore covalently linked to the multichromophore in energy-receiving proximity therewith.

3. The method according to claim 1, further comprising contacting the sample with a second specific binding member that is support bound and specifically binds the target analyte.

4. The method according to claim 3, wherein the support comprises a magnetic particle.

5. The method according to claim 1, wherein the target analyte is associated with a cell.

6. The method according to claim 5, wherein the target analyte is a cell surface marker of the cell.

7. The method according to claim 6, wherein the cell surface marker is selected from the group consisting of a cell receptor and a cell surface antigen.

8. The method according to claim 5, wherein the target analyte is an intracellular target, and the method further comprises lysing the cell.

9. The method according to claim 1, wherein the method further comprises flow cytometrically analyzing the fluorescently labelled target analyte.

* * * * *